(12) United States Patent
Serhan

(10) Patent No.: US 7,741,369 B2
(45) Date of Patent: *Jun. 22, 2010

(54) LIPOXIN COMPOUNDS AND THEIR USE IN TREATING CELL PROLIFERATIVE DISORDERS

(75) Inventor: Charles N. Serhan, Needham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 407 days.

This patent is subject to a terminal disclaimer.

(21) Appl. No.: 11/743,022

(22) Filed: May 1, 2007

(65) Prior Publication Data

US 2009/0258945 A1    Oct. 15, 2009

Related U.S. Application Data

(60) Division of application No. 11/222,172, filed on Sep. 8, 2005, now Pat. No. 7,294,728, which is a continuation of application No. 11/040,605, filed on Jan. 21, 2005, now Pat. No. 7,288,569, which is a division of application No. 10/391,228, filed on Mar. 18, 2003, now Pat. No. 6,887,901, which is a continuation of application No. 09/968,445, filed on Oct. 1, 2001, now Pat. No. 6,569,075, which is a continuation of application No. 09/309,423, filed on May 11, 1999, now Pat. No. 6,316,648, which is a continuation of application No. 08/712,610, filed on Sep. 13, 1996, now Pat. No. 6,048,897, which is a continuation-in-part of application No. 08/453,125, filed on May 31, 1995, now Pat. No. 5,648,512, which is a division of application No. 08/260,030, filed on Jun. 15, 1994, now Pat. No. 5,441,951, which is a continuation-in-part of application No. 08/077,300, filed on Jun. 15, 1993, now abandoned.

(51) Int. Cl.
   *A01N 37/00* (2006.01)
(52) U.S. Cl. ...................................................... 514/560
(58) Field of Classification Search .................. 514/560
   See application file for complete search history.

(56) References Cited

U.S. PATENT DOCUMENTS 4,560,514 A    12/1985  Samuelsson et al.

(Continued)

FOREIGN PATENT DOCUMENTS

JP           62-198677           9/1987

(Continued)

OTHER PUBLICATIONS

Corey, et al., "On the Synthesis and Structure of Lipoxin B", Tetrahedron Letters, vol. 26, No. 16, (1985) pp. 1919-1922.

(Continued)

*Primary Examiner*—Deborah D Carr
(74) *Attorney, Agent, or Firm*—Scott D. Rothenberger; Colin L. Fairman; Fulbright & Jaworski

(57) ABSTRACT

Compounds having the active site of natural lipoxins, but a longer tissue half-life are disclosed. In particular, 15-epi-lipoxins and their use in ameliorating undesired cell proliferation, which characterizes diseases such as cancer, are also disclosed.

10 Claims, 8 Drawing Sheets

U.S. PATENT DOCUMENTS

| | | | |
|---|---|---|---|
| 4,576,758 | A | 3/1986 | Morris |
| 4,780,281 | A | 10/1988 | Marnett et al. |
| 5,049,681 | A | 9/1991 | Sato |
| 5,079,261 | A | 1/1992 | Serhan et al. |
| 5,322,699 | A | 6/1994 | Wright et al. |
| 5,441,951 | A * | 8/1995 | Serhan ............. 514/513 |
| 5,648,512 | A | 7/1997 | Serhan |
| 5,650,435 | A | 7/1997 | Madara et al. |
| 5,998,487 | A | 12/1999 | Brahms et al. |
| 6,048,897 | A | 4/2000 | Serhan |
| 6,316,648 | B1 | 11/2001 | Serhan |
| 6,569,075 | B2 * | 5/2003 | Serhan ............. 514/560 |
| 6,620,919 | B2 | 9/2003 | Serhan |
| 6,635,776 | B2 | 10/2003 | Serhan |
| 6,653,493 | B2 | 11/2003 | Serhan |
| 6,750,360 | B2 | 6/2004 | Serhan |
| 6,887,901 | B1 | 5/2005 | Serhan |
| 7,288,569 | B2 * | 10/2007 | Serhan ............. 514/560 |
| 7,294,728 | B2 | 11/2007 | Serhan |
| 2006/0069158 | A1 | 3/2006 | Serhan |

FOREIGN PATENT DOCUMENTS

| | | |
|---|---|---|
| JP | 63-88153 | 4/1988 |
| JP | 3-227922 | 10/1991 |
| JP | 1-228994 | 9/2001 |
| WO | WO 90/13292 | 12/1994 |
| WO | WO 94/29262 | 12/1994 |
| WO | WO 95/01179 | 1/1995 |
| WO | WO 98/11049 | 3/1998 |
| WO | WO 00/13685 | 3/2000 |
| WO | WO 01/70664 | 9/2001 |

OTHER PUBLICATIONS

Takano et al., "Neutrophil-mediated changes in Vascular Permeability Are Inhibited by Topical Application of Aspiring triggered 15-epi-lipoxin A4 and Novel Lipoxin B4," J. Clin. Invest. The American Society for Clinical Investigations, Inc. vol. 101, No. 4, 1998, pp. 819-826.

Nguyen, et al. "Nonsteroidal anti-inflammatory drug use in dentistry: Gastrointestinal Implications", Pharmacology, Nov. 1999, pp. 590-596.

Maddox, et al., "Lipoxin B4 Regulates Human Monocyte/Neutrophil Adherence and Motility: Design of Stable Lipoxin B4 Analogs with Increased Biologic Activity", The FASEB Journal, vol. 12, Apr. 1998, pp. 487-494.

Pouliot M., et al, "Lipoxin A4 and Aspirin-Triggered 15-EPI-LXA4 Inhibit Tumor Necrosis factor-1 Alpha-Initiated Neutrophil Responses and Trafficking: Novel Regulators of a Cytokine-Chemokine Axis Relevant to Periodontal Diseases", Journal of Periodontal Research, vol. 34, No. 7, Oct. 1999, pp. 370-373.

Fiore et al., "Lipoxin Recognition Sites", The Journal of Biological Chemistry, vol. 267, No. 23, 1992, pp. 16168-16176.

Claria, J. et al., Aspirin Triggers Previously Undescribed Bioactive Eicosanoids by Human Endothelial Cell-Leukocyte Interactions:, Proc, Nat'l Acad. Sci., vol. 92, 1995, pp. 9475-9479.

Serhan, "Lipoxins: Eicosanoids Carrying Intra- and Intercellular Messages", Journal of Bioenergetics and Biomembranes, vol. 23, No. 1, 1991, pp. 105-122.

Mizukami, et al., "ω-Hydroxylation of Lipoxin $B_4$ by Human Neutrophil Microsomes: Identification of ω-Hydroxy Metabolite of Lipoxin $B_4$ and Catalysis by Leukotriene $B_4$ ω-Hydroxylase (cytochrome P-450LTBω)", Biochimica et Biophysica Acta, No. 1168, 1993, pp. 87-93.

Popov, et al., "Effect of Lipoxin B on Colony-Forming Ability of Human Peripheral Blood Mononuclears in a Diffusion Chamber", Translated from Byulleten' Eksperimental' noi Biologii i Meditsiny, vol. 107, No. 1, 1989, pp. 80-83 and 93-98.

Katoh, et al., "Renal Hemodynamic Actions of Lipoxin in Rats: A Comparative Physiological Study", American Journal Physiology, vol. 263, 1992, pp. F436-F442.

Lee, et al., "Inhibition of Leukotriene $B_4$—Induced Neutrophil Migration by Lipoxin $A_4$: Structure-Function Relationships", Biochemical and Biophysical Research Communications, vol. 180, No. 3, 1991, pp. 1416-1421.

Nicolaou, et al., "Lipoxins and Related Eicosanoids: Biosynthesis, Biological Properties, and Chemical Synthesis", Angew. Chem. Int. Ed. Engl., vol. 30, 1991, pp. 1100-1116.

Nicolaou, et al., "Total Synthesis of Novel Geometric Isomers of Lipoxin $A_4$ and Lipoxin $B_4$", Reprint from The Journal of Organic Chemistry, vol. 54, No. 23, 1989, pp. 5527-5535.

Brady, et al., "Leukotrienes Stimulate Neutrophil Adhesion to Mesangial Cells: Modulation with Lipoxins", American Journal Physiology, vol. 259, 1990, pp. F809-F815.

Nicolaou et al., "Identification of a novel 7-cis-11-trans-lipoxin $A_4$ generated by human neutrophils: total synthesis, spasmogenic activities and comparison with other geometric isomers of lipoxins $A_4$ and $B_4$", Biochimica et Biophisica Acta, 1003, 1989, pp. 44-53.

Serhan et al., "Design of Lipoxin A4 Stable Analogs That Block Transmigration and Adhesion of Human Neutrophils", Biochemistry, vol. 34, No. 44, 1995, pp. 14609-14615.

Maddox, et al., "Lipoxin A4 Stable Analogs Are Potent Mimetics That Stimulate Human Monocytes and THP-1 Cells via a G-protein-linked Lipoxin A4 Receptor", The Journal of Biological Chemistry, vol. 272, No. 11, 1997, pp. 6972-6978.

Claria, J. "Aspirin-Triggered Lipoxins (15-epi-LX) Are Generated by the Human Lung Adenocarcinoma Cell Line (A549)- Neutrophil Interactions and Are Potent Inhibitors of Cell Proliferation", Molecular Medicine, vol. 2, No. 5, Sep. 1996, pp. 583-596.

Badr, K.F. "15-Lipoxygenase Products as Leukotriene Antagonists: Therapeutic Potential in Glomerulonephritis", Kidney International, vol. 42, Supp. 38, 1992, pp. S101-S108.

Dahlen, S.E. "Lipoxins and other Lipoxygenase Products with Relevance to Inflammatory Reactions in the Lung", Annals of the New York Academy of Sciences, Advances in the Understanding and Treatment of Astham, (no. date available), pp. 262-273.

Fiore, S. "The Lipoxin Biosynthetic Circuit and their Actions with Human Neutrophils", Advances in Experimental Medicine and Biology, vol. 314, 1991, pp. 109-132.

Fiore, S, et al. "Induction of Functional Lipoxin A4 Receptors in HL-60 Cells", Blood, vol. 81, No. 12, 1993, pp. 3395-3403.

Lederman, S. et al. "Identification of a Novel Surface Protein on Activated CD4+ T Cells that Induces Contact-Dependent B Cell Differentiation (Help)", J. Exp. Med., vol. 175, 1992, pp. 1091-1101.

Madara, J.L. et al. "A Simple Approach to Measurement of Electrical Parameters of Cultured Epithelial Monolayers: Use in Assessing Neutrophil-Epithelial Interactions", J. Tiss. Cult. Meth., vol. 14, 1992, pp. 209-216.

Madara, J.L. et al. "5'-Adenosine Monophosphate is the Neutrophil-derived Paracrine Factor that Elicits Chloride Secretion from T84 Intestinal Epithelial Cell Monolayers", J. Clin. Invest., Vol. 91, 1993, pp. 2320-2325.

Nash, S. et al. "Effects of Polymorphonuclear Leukocyte Transmigration on the Barrier Function of Cultured Intestinal Epithelial Monolayers", J. Clin. Invest., vol. 80, 1987, pp. 1104-1113.

Noelle, R.J. et al., "A 39-kDa Protein on Activated Helper T Cells Binds CD40 and Transduces the Signal for Cognate Activation of B Cells ", Proc. Natl Acad. Sci. USA, vol. 89, 1992, pp. 6550-6554.

Parkos, C.A. et al. "Neutrophil Migration Across a Cultured Intestinal Epithelium", J. Clin. Invest., vol. 88, 1991, pp. 1605-1612.

Parkos, C.A. et al. "Neutrophil Migration Across a Cultured Epithelial Monolayer Elicits a Biphasic Resistance Response Representing Sequential Effects on Transcellular and Paracellular Pathways", The Journal of Cell Biology, vol. 117, No. 4, 1992, pp. 757-764.

Pettitt, T.R. et al., "Synthesis of Lipoxins and Other Lipoxygenase Products by Macrophages form the Rainbow Trout, Oncorhynchus Mykiss", The Journal of Biological Chemistry, vol. 266, No. 14, 1991, pp. 8720-8726.

Samuelsson, B., "An Elucidation of the Arachidonic Acid Cascade Discovery of prostaglandins, Thromboxane and Leukotrienes", Drugs, vol. 33, Supp. 1, 1987, pp. 209.

Leff, A.R. "Role of Leukotrienes in Bronchial Hyperresponsiveness and Cellular Responses in Airways", *Amer. Journal of Respiratory and Critical Care Medicine*, vol. 161, 2000, pp. S125-S132.

Bousquet, J. et al. "Asthma. From bronchoconstriction to Airways Inflammation and Remodeling", *Amer. Journal of Respiratory and Critical Care Medicine*, vol. 161, 2000, pp. 1720-1745.

Robinson, D.S. et al. "Predominant TH2-like Bronchoalveolar T-lymphocyte Population in Atopic Asthma", *New England Journal of Medicine*, vol. 326, 1992, pp. 298-304.

Broide, D.H. et al. "Cytokines in Symptomatic Asthma Airways", *J. Allergy Clin. Immunol.*, vol. 89, 1992, pp. 958-967.

Samuelsson, B. "From Studies of Biochemical Mechanisms to Novel Biological Mediators: Prostaglandin Endoperoxides, Thromboxanes and Leukotrienes", *In Les Prix Nobel: Nobel Prizes, Presentations, Biographies and Lectures*, 1982, pp. 153-174.

Drazen, J.M. et al. "Treatment of Asthma with Drugs Modifying the Leukotriene Pathway", *New England Journal of Medicine*, vol. 340, 1999, pp. 197-206.

Serhan, C.N. et al. "Lipid Mediator Networks in Cell Signaling: Update and Impact of Cytokines", *FASEB Journal*, vol. 10, 1996, pp. 1147-1158.

McMahon, B. et al. "Lipoxins: Revelations on Resolution", *Trends in Pharmacological Sciences*, vol. 22, 2001, pp. 391-395.

Levy, B.D. et al. "Lipid Mediator Class Switching During Acute Inflammation: Signals in Resolution", *Nature Immunology*, vol. 2, 2001, pp. 612-619.

Lee, T.H. et al. "Identification of Lipoxin A4 and its Relationship to Sulfidopeptide Leukotrienes C4, D4, and E4 in the Bronchoalveolar Lavage Fluids obtained from patients with Selected Pulmonary Diseases", *Amer. Review of Respiratory Disease*, vol. 141, 1990, pp. 1453-1458.

Badr, K.F. et al., "Lipoxin A4 Antagonizes Cellular and in Vivo Actions of Leukotriene D4 in rat glomerular mesangial cells: Evidence for Competition at a Common Receptor", *Proc. Nat'l. Acad. Sci. USA*, vol. 86, 1989, pp. 3438-3442.

Gronert, K. et al. "Selectivity of Recombinant Human Leukotriene D4 Leukotriene B4 and Lipoxin A4 Receptors with Aspirin- Triggered 15-epi-LXA4 and Regulation of Vascular and Inflammatory Responses", *Amer. J. Path*, vol. 158, 2001, pp. 3-9.

Takano, T. et al. "Aspirin-Triggered 15-epi-lipoxin A4 (LXA4) and LXA4 Stable Analogues are Potent Inhibitor of Acute Inflammation: Evidence for Anti-Inflammatory Receptors", *Journal of Experimental Medicine*, vol. 185, 1997, pp. 1693-1704.

De Sanctis, G.T. et al. "Interleukin-8 Receptor Modulates IgE Production and B-cell Expansion and Trafficking in Allergen-Induced Pulmonary Inflammation", *J. Clin. Invest.*, vol. 103, 1999, pp. 507-515. De Sanctis, G.T. et al. "Contribution of Nitric Oxide Synthases 1, 2, and 3 to Airway Hyperresponsiveness and Inflammation in a Murine Model of Asthma", *Journal of Experimental Medicine*, vol. 189, 1999, pp. 1621-1630.

Clish, C.B. et al. "Local and Systemic Delivery of a Stable Aspirin-Triggered Lipoxin Prevents Neutrophil Recruitment in Vivo", *Proc. Natl. Acad. Sci. USA*, vol. 96, 1999, pp. 8247-8452.

Holgate, S.T. "The Epidemic of Allergy and Asthma", *Nature*, vol. 402, 1999, pp. B2-B4.

Drazen, J.M. et al. "Heterogeneity of Therapeutic Responses in Asthma", *British Medical Bulletin*, vol. 56, 2000, pp. 1054-1070.

Bryan, S.A. et al. "Effects of Recombinant Human Interleukin-12 on Eosinophils, Airway Hyper-Responsiveness, and the late Asthmatic Response", *Lancet*, vol. 356, 2000, pp. 2149-2153.

Leckie, M.J. et al. "Effects of an Interleukin-5 Blocking Monoclonal Antibody on Eosinophils, Airway Hyper-Responsiveness, and the late Asthmatic Response", *Lancet*, vol. 356, 2000, pp. 2144-2148.

Christie, P.E. et al. "The Effects of Lipoxin A4 on Airway Responses in Asthmatic Subjects", *Amer. Review of Respiratory Disease*, vol. 145, 1992, pp. 1281-1284.

Dahlen, S.E. et al. "Actions of Lipoxin A4 and Related Compounds in Smooth Muscle Preparations and on the Microcirculation in Vivo", *Advances in Experimental Medicine & Biology*, vol. 229, 1988, pp. 107-130.

Venkayya, R. et al. "The Th2 Lymphocyte Products IL-4 and IL-13 Rapidly Induce Airway Hyperresponsiveness Through Direct Effects on Resident Airway Cells", *Amer. Journal of Respiratory Cell & Molecular Biology*, vol. 26, 2002, pp. 202-208.

Laporte, J.C. et al. "Direct Effects of Interleukin-13 on Signaling Pathways for Physiological Responses in Cultured Human Airway Smooth Muscle Cells", *Amer. Journal of Respiratory & Critical Care Medicine*, vol. 164, 2001, pp. 141-148.

Cowburn, A.S. et al. "IL-5 Increases Expression of 5-Lipoxygenase-activating Protein and Translocates 5-Lipoxygenase to the Nucleus in Human Blood Eosinophils", *J. Immun.*, vol. 163, 1999, pp. 456-465.

Hisada, T. et al. "Cysteinyl-leukotrienes Partly Mediate Eotaxin-Induced Bronchial Hyperresponsiveness and Eosinophilia in IL-5 Transgenic Mice", *Amer. Journal of Respiratory & Critical Care Medicine*, vol. 160, 1999, pp. 571-575.

Drazen, J.M. "Leukotrienes as Mediators of Airway Obstruction", *Amer. Journal of Respiratory & Critical Care Medicine*, vol. 158, 1998, pp. S193-S200.

Resnati, M. et al. "The Fibrinolytic Receptor for Urokinase Activates the G-protein-coupled Chemotactic Receptor FPRL1/LXA4R", *Proc. Natl. Acad. Sci.*, vol. 99, 2002, pp. 1359-1364.

Soyombo, O. et al. "Effects of Lipoxin A4 on Chemotaxis and Degranulation of Human Eosinophils Stimulated by Platelet- Activating Factor and N-formly-L-methionyl-L-leucyl-L-phenylalanine", *Allergy*, vol. 49, 1994, pp. 230-234.

Bandeira-Melo, C. et al. "Cutting Edge: Lipoxin (LX) A4 and Aspirin-Triggered 15-epi-LXA4 Block Allergen-Induced Eosinophil Trafficking", *J. Immun.*, vol. 164, 2000, pp. 2267-2271.

Bandeira-Melo, C. et al. "Cyclooxygenase-2-dervied Prostaglandin E2 and Lipoxin A4 Accelerate Resolution of Allergic Edema in Angiostrongylus Costaricensis-infected Rats: Relationship with Concurrent Eosinophilia", *J. Immun.*, vol. 164, 2000, pp. 1029-1036.

Aliberti, J. et al. "Lipoxin-Mediated Inhibition of IL-12 Production by DCs: A Mechanisn for Regulation of Microbial Immunity", Nature Immunology, vol. 3, 2002, pp. 76-82.

Sanak, M. et al. "Aspirin-tolerant Asthmatics Generate More Lipoxins than Aspirin-intolerant Asthmatics", *European Respiratory Journal*, vol. 16, 2000, pp. 44-49.

Godson, C. et al. "Cutting Edge: Lipoxins Rapidly Stimulate Nonphologistic Phagocytosis of Apoptotic Neutrophils by Monocyte-derived Macrophages", *J. Immun.*, vol. 164, 2000, pp. 1663-1667.

Chiang N. et al. "Leukotriene B4 Receptor Transgenic Mice Reveal Novel Protective Roles for Lipoxins and Aspirin-Triggered Lipoxins in Reperfusion", *J. Clin. Invest.*, vol. 164, 1999, pp. 309-316.

Wu, W. et al. "Eosinophils Generate Brominating Oxidants in Allergen-induced Asthma", *J. Clin. Invest.*, vol. 105, 2000, pp. 1455-1463.

Serhan, C.N. , "Lipoxin biosynthesis and its impact in inflammatory and vascular events", *Biochimica et Biophysica Acta*, 1994, pp. 1-25.

Serhan, C.N., et al., "Unorthodox routes to prostanoid formation: new twists in cyclooxygenase-initiated pathways", *J. Clin. Invest.* ,vol. 107, No. 12, 2001, pp. 1481-1489.

Elsbach, P. et al., "Role of the bactericidal/permeability-increasing protein in host defence", *Current Opinion in Immunlogy*, vol. 10, No. 1, 1998, pp. 45-49.

Ganz, T. et al., "Antimicrobial peptides of phagocytes and epithelia", *Seminars in Hematology*, vol. 34, No. 4, 1997, pp. 343-354.

Levy, O., "A neutrophil-derived anti-infective molecule: bactericidal/permeability-increasing protein", *Antimicrobial Agents and Chemotherapy*, vol. 44, No. 11, 2000, pp. 2925-2931.

Levy, O., "Antimicrobial proteins and peptides of blood: templates for novel antimicrobial agents", *Blood*, vol. 96, No. 8, 2000, pp. 2664-2672.

Beamer, L.J. et al., "Crystal structure of human BPI and two bound phospholipids at 2.4 angstrom resolution", *Science*, vol. 276, 1997, pp. 1861-1864.

Dharmsathaphorn, K. et al., "Established intestinal cell lines as model systems for electrolyte transport studies", *Methods in Enzymology*, vol. 192, 1990, pp. 354-389.

Madianos, P.N. et al., "*Porphyromonas gingivalis* infection of oral epithelium inhibits neutrophil transepithelial migration", *Infection and Immunity*, vol. 65, No. 10, 1997, pp. 3983-3990.

Lennon, P.F., et al., "Neutrophil-dervied 5'-adenosine monophosphate promotes endothelial barrier function via CD73- mediated conversaion to adenosine and endothelial $A_{2B}$ receptor activation", *J. Exp. Med.*, vol. 188, No. 8, 1998, pp. 1433-1443.

Dickson, M.A. et al., "Human keratinocytes that express hTERT and also bypass a p16 $^{INK4a}$-enforced mechanism that limited life span become immortal yet retain normal growth and differentiation characteristics", *MCB*, vol. 20, No. 4, 2000, pp. 1436-1447.

Lockhart, D.J. et al., "Expression monitoring by hybridization to high-density oligonucleotide arrays", *Nature Biotechnology*, vol. 14, No. 13, 1996, pp. 1675-1680.

Taylor, C.T. et al., "Critical role of cAMP response element binding protein expression in hypoxia-elicited induction of epithelial tumor necrosis factor-a",*J. Biolog. Chem.*, vol. 274. No. 27, 1999, pp. 19447-19454.

Parkos, C.A. et al., "CD47 mediates post-adhesive events required for neutrophil migration across polarized intestinal epithelia", *J. Cell Biology*, vol. 132, 1996, pp. 437-450.

Bevilacqua, M.P. et al., "Identification of an inducible endothelial-leukocyte adhesion molecule", *Proc. Natl. Acad. Sci. USA*,vol. 84, 1987, pp. 9238-9242.

Dittel, B.N. et al., "Regulation of human B-cell precursor adhiesion to bone marrow stromal cells by cyokines that exert opposing effects on the expression of vascular cell adhesion molecule-1 (VCAM-1)", *Blood*, vol. 81, No. 9, 1993, pp. 2272-2282.

Weinrauch, Y. et al., "Extracellular accumulation of potently microbicidal bactericidal/permeability-increasing protein and p15s in an evolving sterile rabbit peritoneal inflammatory exudates", *J. Clin. Invest.*, vol. 95, 1995, pp. 1916-1924.

McCormick, B.A. et al., "*Salmonella typhimurium* attachment to human intestinal epithelial monolayers: transcellular signaling to subepithelial neurophils", *J. Cell Biology*, vol. 123, No. 4, 1993, pp. 895-907.

Colgan, S.P. et al., "Defective invitro motility of polymorphonuclear leukocytes of homozygotte and heterozygote Chediak-Higashi cats", *Vet. Immunol. Immunopathology*, 1992, pp. 205-227.

Colgan, S.P. et al, "Lipoxin A4 modulates transmigration of human neutrophils across intestinal epithelial monolayers", *J. Clin. Invest.*, vol. 92, 1993, pp. 75-82.

Weersink, A., et al., "Human granulocytes express a 550-kDa lipopolysaccharide-binding protein on the cell surface that is identical to the bactericidal/permeability-incresing protein", *J. Immunology*, vol. 150, No. 1, 1993, pp. 253-263.

Weiss, J. et al., "Purification and characterization of a potent bactericidal and membrane active protein from the granules of human polymorphonuclear leukocytes", *J. Biol. Chem.*, vol. 253, No. 8, 1978, pp. 2664-2672.

Gottardi, C.J. et al., "Cell surface biotinylation in the determination of epithelial membrane polarity", *J. Tiss. Cult. Meth.*, vol. 14, No. 4, 1992, pp. 173-180.

Pugin, J. et al., "Lipopolysaccharide activation of human endothelial and epithelial cells is mediated by lipopolysaccharide-binding protein and soluble CD14", *Proc. Nat. Acad. Sci. USA*, vol. 90, 1993, pp. 2744-2748.

Cotran, R.S. et al., "Endothelial adhesion molecules in health and disease", *Pathologie Biologie*, vol. 46, No. 3, 1998, pp. 164-170.

Ouellette, A.J., "Mucosal immunity and inflammation IV. paneth cell antimicrobial peptides and the biology of the mucosal barrier", *Am. J. Physiol*, vol. 40, No. 2, 1999, pp. G257-G261.

Harwig, S. et al., Bactericidal properties of murine intestinal phospholipase $A_2$, *J. Clin. Invest.*, vol. 95, 1995, pp. 603-610.

Imler, J.L. et al., "Toll receptors in innate immunity", *Trends in Cell Biology*, vol. 11, No. 7, 2001, pp. 304-311.

Cario, E. et al., "Differential alteration in intestinal epithelial cell expression of toll-like receptor # (TLR3) and TLR4 in inflammatory bowel disease", *Infection and Immunity*, vol. 68, No. 12, 2000, pp. 7010-7017.

Wong, P.K. et al., "Lipoxins inhibit microvascular inflammatory actions of leukotriene $B_4$", *Cell-Cell Interactions in the Release of Inflammatory Mediatiors*, 1991, pp. 185-192.

Pouliot, M. et al., "Lipoxin A4 analogues inhibit leukocyte recruitment to *Porphromonas gingivalis*: a role for cycloosygenase-2 and lipoxins in periodontal disease", *Biochemistry*, vol. 39, No. 16, 2000, pp. 4761-4768.

Dubois, R.N. et al., "Cyclooxygenase in biology and disease", *FASEB Journal*, vol. 12, 1998, pp. 1063-1073.

Nisengard, R.J. et al., "Peridontal disease", *Oral Microbiology and Immunology*, vol. 2, 1994, pp. 360-384.

Sartor, R.B., "Microbial factors in the pathogenesis of Crohn's disease, ulcerative colitis, and experimental intestinal inflammation", *Inflammatory Bowel Disease*, Fourth Edition, 1995, pp. 96-124.

Monajemi, H. et al., "Inflammatory bowel disease is associated with increased mucosal levels of bactericidal/permeability-increasing protein", *Gastroenterology*, vol. 110. No. 3, 1996, pp. 733-739.

Haapamaki M.M., et al., "Bactericidal/permeability-increasing protein in colonic mucosa in ulcerative colitis", *Hepato-Gastroenterology*, vol. 46, 1999, pp. 2273-2277.

Stoffel, M.P. et al., "Anti-neutrophil cytoplasmic antibodies (ANCA) directed against bactericidal/permeability increasing protein (BPI): a new seromarker for inflammatory bowel disease and associated disorders", *Clin. Exp. Immunology*, vol. 104, 1996, pp. 54-59.

Levin, M. et al., "Recominant bactericidal/permeability-increasing protein ($rBPI_{21}$) as adjunctive treatment for children with severe meningococcal spsis: a randomised trial", *Lancet*, vol. 356, No. 9234, 2000, pp. 961-967.

Levy, O. et al., "Bactericidal/permeability-increasing protein in host defense and its efficacy in the treatment of bacterial sepsis", *Curr. Infect. Dis. Reports*, vol. 3, 2001, pp. 407-412.

* cited by examiner

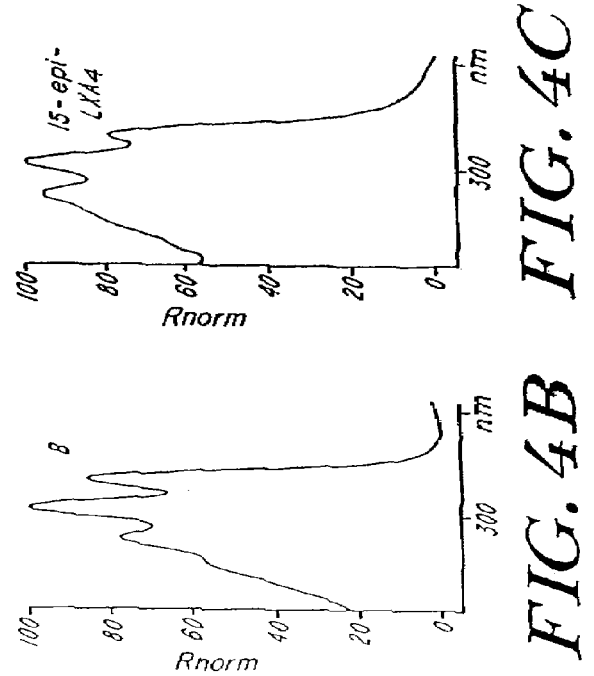
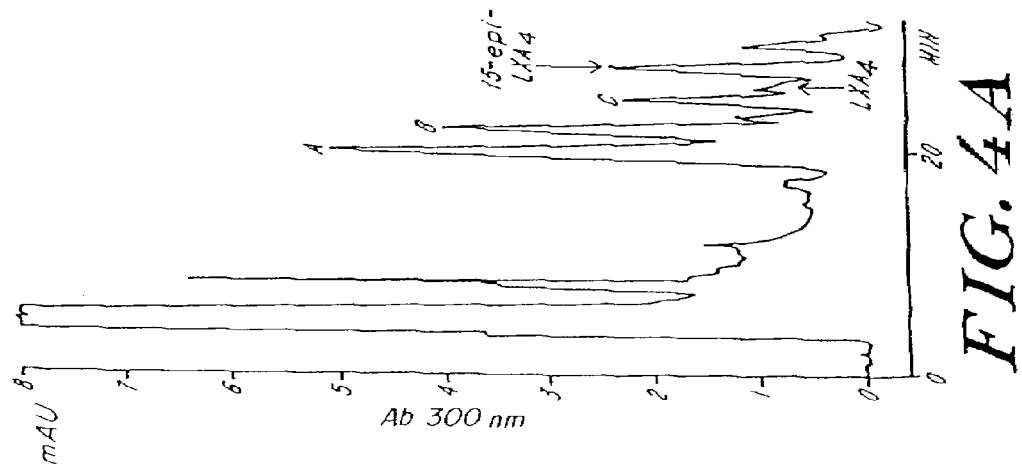

```
                         SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iv) ANTI-SENSE: NO (xi) SEQUENCE DESCRIPTION: SEQ ID NO: 1:

TGCCCAGCTC CTGGCCCGCC GCTT                                              24

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 2:

GTGCATCAAC ACAGGCGCCT CTTC                                              24

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (iv) ANTI-SENSE: NO (xi) SEQUENCE DESCRIPTION: SEQ ID NO: 3:

TTCAAATGAG ATTGTGGGAA AATTGCT                                           27

(2) INFORMATION FOR SEQ ID NO: 4:

(i) SEQUENCE CHARACTERISTICS:
        (A) LENGTH: 24 base pairs
```

```
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 4:

AGATCATCTC TGCCTGAGTA TCTT                                           24

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iv) ANTI-SENSE: NO (xi) SEQUENCE DESCRIPTION: SEQ ID NO: 5:

ATGGGTCTCT ACCGCATCCG CGTGTCCACT                                     30

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 6:

CACCCAGCGG TAACAAGGGA ACCTGACCTC                                     30

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: NO (xi) SEQUENCE DESCRIPTION: SEQ ID NO: 7:

AGTTCCTCAA TGGTGCCAAC                                                20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 8:

ACAGTGTTGG GGTTGGAGAG                                                20
```

```
(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iv) ANTI-SENSE: NO (xi) SEQUENCE DESCRIPTION: SEQ ID NO: 9:

GAAGACCTGA TGTTTGGCTA CC                                              22

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 10:

AGGGTTCTCA TCTCCCGG                                                   18

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iv) ANTI-SENSE: NO (xi) SEQUENCE DESCRIPTION: SEQ ID NO: 11:

CCACCCATGG CAAATTCCAT GGCA                                            24

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO: 12:

TCTAGACGGC AGGTCAGGTC CACC                                            24
```

LIPOXIN COMPOUNDS AND THEIR USE IN TREATING CELL PROLIFERATIVE DISORDERS

CROSS REFERENCE TO RELATED APPLICATION(S)

This application is a Divisional application of Continuation application Ser. No. 11/222,172, filed Sep. 8, 2005, which is a Continuation of application Ser. No. 11/040,605, filed Jan. 21, 2005, which claims benefit of Divisional application Ser. No. 10/391,228, filed Mar. 18, 2003, now U.S. Pat. No. 6,887,901, which is a commonly owned U.S. Ser. No. 09/968,445, filed Oct. 1, 2001, now U.S. Pat. No. 6,569,075, which is a continuation application of and claims the benefit of commonly owned U.S. Ser. No. 09/309,423, filed May 11, 1999, now U.S. Pat. No. 6,316,648 which is a divisional application of and claims the benefit of commonly owned U.S. Ser. No. 08/712,610, filed on Sep. 13, 1996, now U.S. Pat. No. 6,048,897 which is a continuation-in-part application of and claims the benefit of commonly owned Ser. No. 08/453,125, filed on May 31, 1995, now U.S. Pat. No. 5,648,512 which in turn is a divisional application of commonly owned Ser. No. 08/260,030, filed on Jun. 15, 1994, now U.S. Pat. No. 5,441,951 which in turn is a continuation-in-part application of commonly owned Ser. No. 08/077,300, filed on Jun. 15, 1993. The contents of all of the aforementioned application(s) are hereby incorporated by reference.

GOVERNMENT SUPPORT

The work leading to this invention was supported in part by one or more grants from the U.S. Government. The U.S. Government therefore may have certain rights in the invention.

BACKGROUND

Lipoxins are a group of biologically active mediators derived from arachidonic acid through the action of lipoxygenase (LO) enzyme systems. (Serhan, C. N. and Samuelsson, B. (1984) Proc. Natl. Acad. Sci. USA 81:5335). Formulation in human cell types is initiated by 5-LO or 15-LO. (Serhan, C. N. (1991) J. Bioenerg. Biomembr. 23:105). Single-cell types generate lipoxins at nanogram levels during human neutrophil-platelet and eosinophil transcellular biosynthesis of eicosanoids. (Serhan, C. N. and Sheppard, K.-A. (1990) J. Clin. Invest. 85:772). LXs are conjugated tetraene-containing eicosanoids that modulate cellular events in several organ systems.

Lipoxin $A_4$ ($LXA_4$) and lipoxin $B_4$ ($LXB_4$) are the two major lipoxins. Each enhances protein kinase C (PKC) activity in nuclei of erythroleukemia cells at 10 nM (Beckman, B. S. et al. (1992) Proc. Soc. Exp. Biol. Med. 201:169). Each elicits prompt vasodilation at nM levels (Busija, D. W. et al. (1989) Am. J. Physiol. 256:H468; Katoh, T. et al. (1992) Am. J. Physiol. 263 (Renal Fluid Electrolyte Physiol. 32):F436). The vasodilatory effects of lipoxins are well-documented. For example, administration of $LXA_4$ in micromolar amounts via inhalation blocks bronchoconstriction in asthmatic patients. (Christie, P. E. et al. (1992) Am. Rev. Respir. Dis. 145:1281).

In the $10^{-10}$ M range, $LXA_4$ also stimulates cell proliferation in combination with suboptimal concentrations of granulocyte-macrophage colony stimulating factor (GM-CSF) to induce myeloid bone marrow colony formation (Stenke, L. et al. (1991) Biochem. Biophys. Res. Commun. 180:255). $LXA_4$ also stimulates human mononuclear cell colony formation (Popov, G. K. et al. (1989) Bull. Exp. Biol. Med. 107:93).

$LXA_4$ inhibits chemotaxis of polymorphonuclear leukocytes (Lee, T. H. et al. (1991) Biochem. Biophys. Res. Commun. 180:1416). An equimolar combination of lipoxins has been found to modulate the polymorphonuclear neutrophil-mesangial cell interaction in glomerular inflammation (Brady, H. R. et al (1990) Am. J. Physiol. 809). Activation of the polymorphonuclear neutrophils (PMN) includes the release of mediators of structural and functional abnormalities associated with the early stages of glomerular inflammation. (Wilson, C. B. and Dixon, F. J. (1986) In: The Kidney, edited by B. M. Brenner and F. C. Rector. Philadelphia, Pa.: Saunders, p. 800-891).

Lipoxins act as antagonists to leukotrienes (LT), which are mediators of inflammation. $LXA_4$ modulates $LTC_4$-induced obstruction of airways in asthmatic patients. (Christie, P. E. et al. (1992) Am. Rev. Respir. Dis. 145:1281). $LXA_4$ inhibits $LTD_4$- and $LTB_4$-mediated inflammation in animal in vivo models. (Badr, K. F. et al. (1989) Proc. Natl. Acad. Sci. 86:3438; Hedqvist, P. et al. (1989) Acta Physiol. Scand. 137:571). Prior exposure to $LXA_4$ (nM) blocks renal vasoconstrictor actions of $LTD_4$ (Katoh, T. et al (1992) Am. J. Physiol. 263 (Renal Fluid Electrolyte Physiol. 32) F436). Leukotriene-induced inflammation occurs, for example, in arthritis, asthma, various types of shock, hypertension, renal diseases, allergic reactions, and circulatory diseases including myocardial infarction.

Although lipoxins are potent small molecules that could be administered in vivo to treat a number of diseases and conditions, these molecules are short-lived in vivo. Compounds having the same bio-activities as natural lipoxins, but a longer in vivo half-life would be valuable pharmaceuticals.

SUMMARY OF THE INVENTION

This invention features substantially purified 15-epi-lipoxin compounds. In one embodiment, the 15-epi-lipoxin compound is 15R-5,6,15-trihydroxy-7,9,13-trans-11-cis-eicosatetraenoic acid and in another embodiment, this acid has a 5S,6R, configuration (15-epi-$LXA_4$). In other embodiments, the 15-epi-lipoxin compound is 15R-5,14,15-trihydroxy-6,10,12-trans-8-cis-eicosatetraenoic acid, and this acid has a 5S,14R configuration (15-epi-$LXB_4$). In still other embodiments, the 15-epi-lipoxin compound is 15-hydroxyeicosatetraenoic acid (15-HETE), and this acid has a 15R configuration.

This invention also features lipoxin analogs, which have an active region that is the same or similar to natural lipoxin, but a metabolic transformation region which is more resistant to in vivo catabolism. The instant disclosed lipoxin analogs therefore have the biological activity of natural lipoxins, but a longer metabolic half-life. Certain of the instant disclosed lipoxin analogs may additionally have an increased in vivo potency, higher binding affinity to lipoxin receptors or enhanced bio-activity as compared to natural lipoxins.

Like natural lipoxins, the instant disclosed small molecules are highly potent and biocompatible (i.e. non-toxic). However, unlike natural lipoxins, lipoxins analogs inhibit, resist, or more slowly undergo metabolism and therefore have a longer pharmacological activity. Further, the instant disclosed compounds are more lipophilic than natural lipoxins and therefore are more readily taken up by biological membranes.

In addition, the invention features methods of ameliorating an undesired proliferation of certain cells based on contacting the cells with an effective amount of a substantially purified 15-epi-lipoxin compound. In preferred embodiments, the cells are undergoing cancerous or tumorous growth. Also in preferred embodiments, the cells are selected from the group consisting of: an epithelial cell, a leukocyte, an endothelial cell, and/or a fibroblast. In certain preferred embodiments of the invention, cells are contacted in vivo. In another embodiment, cells are contacted ex vivo.

The invention also features methods for ameliorating a cell proliferative disorder in a subject by administering an effective amount of a substantially purified 15-epi-lipoxin compound.

In another aspect, the invention features pharmaceutical compositions having the substantially purified 15-epi-lipoxin compound of the present invention and a pharmaceutically acceptable carrier. In a preferred embodiment, the 15-epi-lipoxin compound is in an amount effective to prevent an undesired proliferation of cells in a subject. In another embodiment, the pharmaceutical composition includes an effective amount of acetylsalicylic acid (ASA).

The invention further relates to diagnostic and research uses of the lipoxin compounds. Additional features and advantages of the invention will become more apparent from the following detailed description and claims.

BRIEF DESCRIPTION OF THE DRAWINGS

FIG. 4A is a graph showing a RP-HPLC chromatogram of products from epithelial cell-polymorphonuclear neutrophils (PMN) costimulation. Confluent A549 cells were exposed to IL-$1_β$ (1 ng/ml) for 24 h, treated with ASA (20 min) and arachidonic acid (20 µM, 60 s) and each incubated with freshly isolated PMN (A549 cell:PMN cell ratio of 1:8) followed by stimulation with ionophore $A_{23187}$ (5 µM) in 4 ml of Hank's balanced salt solution (HBSS) for 30 min at 37° C. Products were extracted and taken to RP-HPLC as described in the Methods section of Example 5. The chromatogram was plotted at 300 nm and is representative of n=6 experiments.

FIG. 4B is a graph showing on-line ultra-violet (UV) spectra of products from the epithelial cell-PMN costimulation described in FIG. 4A. Material eluting beneath peak B was identified as predominantly 15-epi-$LXB_4$.

FIG. 4C is a graph showing on-line UV spectra of products from the epithelial cell-PMN costimulation described in FIG. 4A. Material eluting beneath the illustrated peaks was identified as predominantly 15-epi-$LXA_4$.

DETAILED DESCRIPTION OF THE INVENTION

Figure 1A:
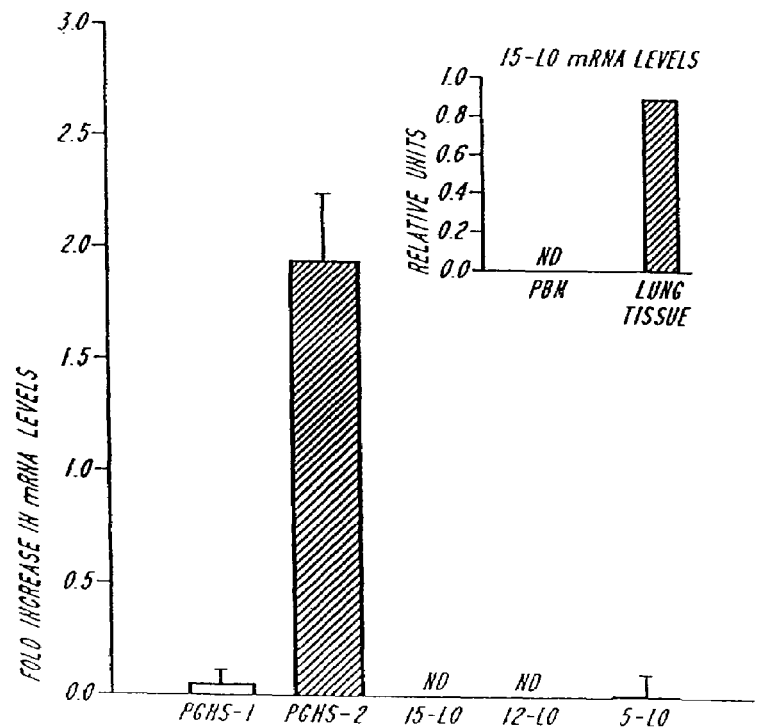
FIG. 1A is a graph showing prostaglandin endoperoxide synthase (PGHS) and lipoxygenase (LO) expression in human tumor cell line (A549 cells) alveolar type II epithelial cells. Cells were grown for 24 h at 37° C. in T-75 $cm^2$ flasks in the presence or absence of Interleukin-1β (IL-$1_β$) (1 ng/ml). Extracted total RNA (1 µg) was taken for Reverse Transcription (RT) and PCR using specific oligonucleotides for PGHS-1 and -2, 15-, 12- and 5-LO and glyceraldehyde-3-phosphate dehydrogenase (GAPDH). Radioactive bands were quantified directly by phosphorimager analysis, normalized to the expression of GAPDH and expressed as fold increase in mRNA levels after exposure to IL-$1_β$. The inset of FIG. 1A shows 15-LO mRNA expression in human lung tissue and peripheral blood monocytes (PBM) with ND meaning 15-LO mRNA expression not detected.

As used herein, the following phrases and terms are defined as follows:

A "lipoxin compound" shall mean a natural lipoxin compound (lipoxin A4 or lipoxin $B_4$) and/or a lipoxin analog.

A "lipoxin analog" shall mean a compound which has an "active region" that functions like the active region of a "natural lipoxin", but which has a "metabolic transformation region" that differs from natural lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the skilled artisan. The present invention is intended to include the possible diastereisomers as well as the racemic and optically resolved isomers.

A preferred lipoxin compound for use in the subject invention is a "15-epi-lipoxin compound". As used herein, "15-epi-lipoxin compound" is a lipoxin compound in which the absolute configuration at the 15 Carbon is R.

The term "15-epi-lipoxin compound" is intended to encompass precursors. The term "precursor" is intended to refer to chemical intermediates that can be converted in vivo, ex vivo and/or in vitro to form the 15-epi-lipoxin compounds of the invention. The term "precursor" also contemplates prodrugs which are converted in vivo to the 15-epi-lipoxin compounds of the invention (see, e.g., R. B. Silverman, 1992, "The Organic Chemistry of Drug Design and Drug Action", Academic Press, Chp. 8). Examples of such prodrugs include, but are not limited to esters of hydroxyls and/or carboxyl groups and/or compounds which can be hydrolyzed or otherwise converted in vivo or, ex vivo and/or in vitro into the 15-epi-lipoxin compounds of the present invention.

The terms "corresponding lipoxin" and "natural lipoxin" refer to a naturally-occurring lipoxin or lipoxin metabolite. Where an analog has activity for a lipoxin-specific receptor, the corresponding or natural lipoxin is the normal ligand for that receptor. For example, where an analog is a $LXA_4$ analog having specific activity for a $LXA_4$ specific receptor on differentiated HL-60 cells, the corresponding lipoxin is $LXA_4$. Where an analog has activity as an antagonist to another compound (such as a leukotriene), which is antagonized by a naturally-occurring lipoxin, that natural lipoxin is the corresponding lipoxin.

The term "active region" shall mean the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. Preferred lipoxin $A_4$ analogs have an active region comprising $C_5$-$C_{15}$ of natural lipoxin $A_4$. Preferred lipoxin $B_4$ analogs have an active region comprising C5-C14 of natural lipoxin B4.

The term "recognition site" or receptor is art-recognized and is intended to refer generally to a functional macromolecule or complex of macromolecules with which certain groups of cellular messengers, such as hormones, leukotrienes, and lipoxins, must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. A nonlimiting example of a metabolic transformation region of a lipoxin is a portion of $LXA_4$ that includes the C-13,14 double bond or the C-15 hydroxyl group, or both.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled lipoxin analog" is further understood to encompass compounds which are labeled with radioactive isotopes, such as but not limited to tritium ($^3H$), deuterium ($^2H$), carbon ($^{14}C$), or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes a native lipoxin. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite.

The term "resists metabolism" is meant to include failing to undergo one or more of the metabolic degradative transformations by at least one of the enzymes which metabolize lipoxins. Two nonlimiting examples of $LXA_4$ analog that resists metabolism are 1) a structure which can not be oxidized to the 15-oxo form, and 2) a structure which may be oxidized to the 15-oxo form, but is not susceptible to enzymatic reduction to the 13,14-dihydro form.

The term "more slowly undergoes metabolism" means having slower reaction kinetics, or requiring more time for the completion of the series of metabolic transformations by one or more of the enzymes which metabolize lipoxin. A nonlimiting example of a $LXA_4$ analog which more slowly undergoes metabolism is a structure which has a higher transition state energy for C-15 dehydrogenation than does $LXA_4$ because the analog is sterically hindered at the C-16.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo.

The term "pharmaceutically acceptable salt" is intended to include art-recognized pharmaceutically acceptable salts. These non-toxic salts are usually hydrolyzed under physiological conditions, and include organic and inorganic bases Examples of salts include sodium, potassium, calcium, ammonium, copper, and aluminum as well as primary, secondary, and tertiary amines, basic ion exchange resins, purines, piperazine, and the like. The term is further intended to include esters of lower hydrocarbon groups, such as methyl, ethyl, and propyl.

The term "pharmaceutical composition" comprises one or more lipoxin analogs as active ingredient(s), or a pharmaceutically acceptable salt(s) thereof, and may also contain a pharmaceutically acceptable carrier and optionally other therapeutic ingredients. The compositions include compositions suitable for oral, rectal, ophthalmic, pulmonary, nasal, dermal, topical, parenteral (including subcutaneous, intramuscular and intravenous) or inhalation administration. The most suitable route in any particular case will depend on the nature and severity of the conditions being treated and the nature of the active ingredient(s). The compositions may be presented in unit dosage form and prepared by any of the methods well-known in the art of pharmacy. Dosage regimes may be adjusted for the purpose to improving the therapeutic response. For example, several divided dosages may be administered daily or the dose may be proportionally reduced over time. A person skilled in the art normally may determine the effective dosage amount and the appropriate regime. A lipoxin analog pharmaceutic composition can also refer to a combination comprising lipoxins, lipoxin analogs, and/or lipoxin metabolites, including metabolites of lipoxin analogs. A nonlimiting example of a combination is a mixture comprising a lipoxin analog x which inhibits one enzyme which metabolizes lipoxins and which optionally has specific activity with a lipoxin receptor recognition site, and a second lipoxin analogy which has specific activity with a lipoxin receptor recognition site and which optionally inhibits or resists lipoxin metabolism. This combination results in a longer tissue half-life for at least y since x inhibits one of the enzymes which metabolize lipoxins. Thus, the lipoxin action mediated or antagonized by y is enhanced.

The term "substantially pure or purified" lipoxin compounds are defined as encompassing natural or synthetic compounds of lipoxins having less than about 20% (by dry weight) of other biological macromolecules, and preferably having less than about 5% other biological macromolecules (but water, buffers, and other small molecules, especially molecules having a molecular weight of less than 5000, can be present. The term "purified" as used herein preferably means at least 80% by dry weight, more preferably in the range of 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

The term "subject" is intended to include living organisms susceptible to conditions or diseases caused or contributed to by inflammation, inflammatory responses, vasoconstriction, myeloid suppression and/or undesired cell proliferation. Examples of subjects include humans, dogs, cats, cows, goats, and mice. The term subject is further intended to include transgenic species.

The term "cell proliferative disorder" includes disorders involving the undesired proliferation of a cell. Non-limiting examples of such disorders include tumors, (e.g., brain, lung (small cell and non-small cell), ovary, prostate, breast or colon) or other carcinomas or sarcomas (e.g., leukemia, lymphoma).

The term "ameliorated" in intended to include treatment for, prevention of, limiting of and/or inhibition of undesired cell proliferation and/or a cell proliferative disorder.

Lipoxin Compounds

The instant invention is based on the surprising finding that substantially pure 15-epi-lipoxin compounds ameliorate undesired cell proliferation in a subject. The 15-epi-lipoxin compounds of the present invention include 15R-5,6,15-trihydroxy-7,9,13-trans-11-cis-eicosatetraenoic acid, in a 5S,6R configuration (15-epi-$LXA_4$). The 15-epi-lipoxin compounds of the present invention also include 15R-5,14,15-trihydroxy-6,10,12-trans-8-cis-eicosatetraenoic acid, in a 5S,14R configuration (15-epi-$LXB_4$). The 15-epi-lipoxins of the present invention further include 15-hydroxyeicosatetraenoic acid, particularly in a 15R configuration.

The instant invention is based on the surprising finding that lipoxins are rapidly metabolized in a unique fashion by certain cells in vivo. Although other LO-derived products (e.g. leukotrienes) are metabolized by ω-oxidation followed by β-oxidation (Huwyler et al., (1992) *Eur. J. Biochem.* 206, 869-879), the instant invention is based on the unexpected finding that lipoxins are metabolized by a series of oxidation and reduction reactions acting on certain sites of the lipoxin molecule. For example, LXA$_4$ metabolism has been found to occur, at least in part, via oxidation of the C-15 hydroxyl to generate 15-oxo-LXA$_4$, reduction of the C-13,14 double bond to yield 13,14-dihydro-15-oxo-LXA$_4$ and further reduction to yield 13,14-dihydro-LXA$_4$. In LXB$_4$ and its natural isomers the analogous oxidation occurs at the C-5 hydroxyl and reduction occurs at the C-6,7 double bond.

Thus, the instant invention features lipoxin analogs having lipoxin activity, but which are chemically modified to prevent dehydrogenation and therefore subsequent degradation in vivo. In these analogs, the C-1 to C-13 portion of the natural lipoxin may or may not be conserved. Variations of the C-1 to C-13 portion include different cis or trans geometry as well as substitutions. The disclosed compounds is represented below by a structural genus, which is further divided into subgenuses. Subgenuses included in each of the following two R groups is denoted by a Roman numeral on the left of the page.

The instant lipoxins comprising an "active region" and a "metabolic transformation region" as both terms are defined herein are generally of the following structure:

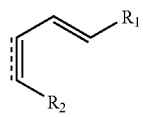

wherein R$_1$ can be

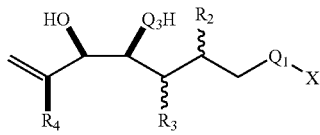

I, II, III, VI

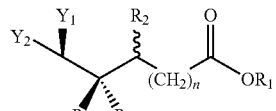

V

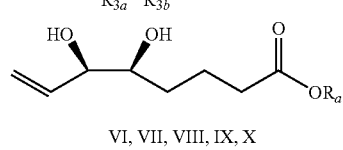

VI, VII, VIII, IX, X

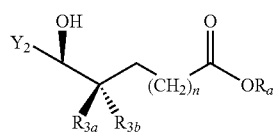

XI and R$_2$ can be

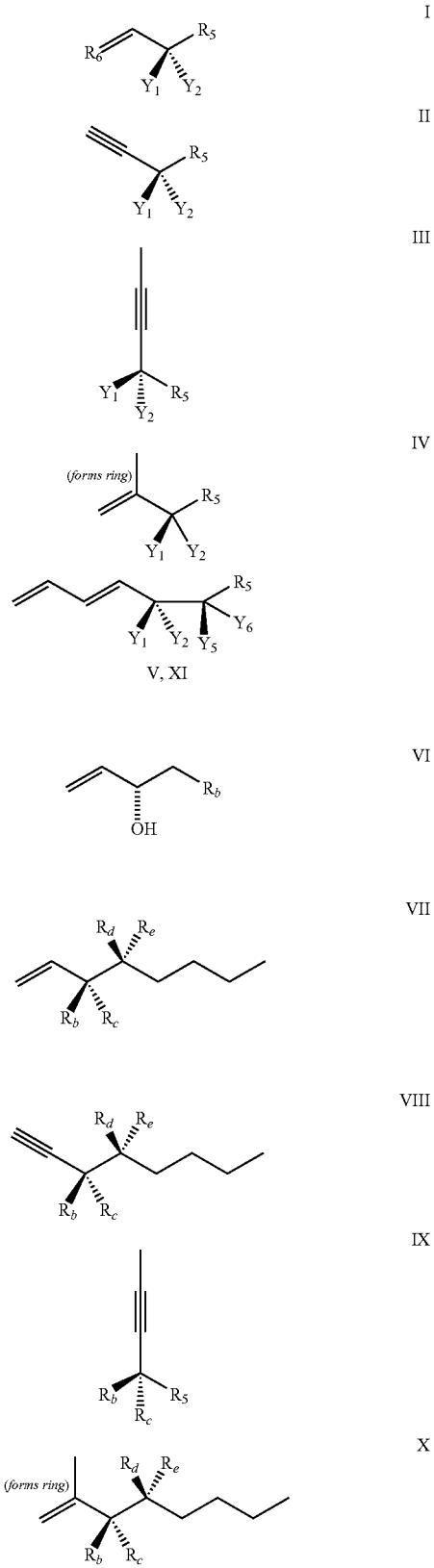

In one embodiment, the lipoxin analogs of this invention have the following structural formula I:

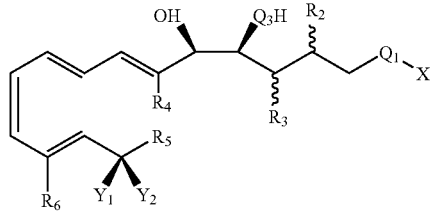

wherein X is $R_1$, $OR_1$, or $SR_1$;
wherein $R_1$ is
(i) hydrogen;
(ii) alkyl of 1 to 8 carbons atoms, inclusive, which may be straight chain or branched;
(iii) cycloalkyl of 3 to 10 carbon atoms, inclusive;
(iv) aralkyl of 7 to 12 carbon atoms;
(v) phenyl;
(vi) substituted phenyl

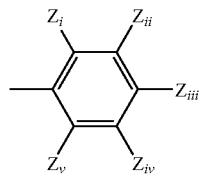

wherein $Z_i$, $Z_{iii}$, and $Z_v$ are each independently selected from the group consisting of $-NO_2$, $-CN$, $-C(=O)-R_1$, $-SO_3H$, and hydrogen;
wherein $Z_{ii}$ and $Z_{iv}$ are each independently selected from the group consisting of halogen, methyl, hydrogen, and hydroxyl;
(vii) detectable label molecule; or
(viii) straight or branched chain alkenyl of 2 to 8 carbon atoms, inclusive;
wherein $Q_1$ is (C=O), $SO_2$ or (CN);
wherein $Q_3$ is O, S or NH;
wherein one of $R_2$ and $R_3$ is hydrogen and the other is
(a) H;
(b) alkyl of 1 to 8 carbon atoms, inclusive, which may be straight chain or branched;
(c) cycloalkyl of 3 to 6 carbon atoms, inclusive;
(d) alkenyl of 2 to 8 carbon atoms, inclusive, which may be straight chain or branched; or
(e) $R_aQ_2R_b$
wherein $Q_2$ is $-O-$ or $-S-$;
wherein $R_a$ is alkylene of 0 to 6 carbons atoms, inclusive, which may be straight chain or branched; and
wherein $R_b$ is alkyl of 0 to 8 carbon atoms, inclusive, which may be straight chain or branched;
wherein $R_4$ is
(a) H;
(b) alkyl of 1 to 6 carbon atoms, inclusive, which may be straight chain or branched;
wherein $Y_1$ or $Y_2$ is $-OH$, methyl, or $-SH$ and wherein the other is
(a) H
(b) $CH_aZ_b$
where a+b=3, a 0 to 3, b=0 to 3; and
Z is cyano, nitro, or halogen;
(c) alkyl of 2 to 4 carbon atoms, inclusive, straight chain or branched; or
(d) alkoxy of 1 to 4 carbon atoms, inclusive;
or $Y_1$ and $Y_2$ taken together are
(a) =N; or
(b) =O;
wherein $R_5$ is
(a) alkyl of 1 to 9 carbon atoms which may be straight chain or branched;
(b) $-(CH_2)_n-R_i$
wherein n=0 to 4 and $R_i$ is
(i) cycloalkyl of 3 to 10 carbon atoms, inclusive;
(ii) phenyl; or
(iii) substituted phenyl

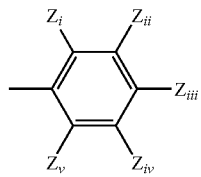

wherein $Z_i$, $Z_{iii}$, and $Z_v$ are each independently selected from the group consisting of hydrogen, $-NO_2$, $-CN$, $-C(=O)-R_1$, methoxy, and $-SO_3H$; and
wherein $Z_{ii}$ and $Z_{iv}$ are each independently selected from the group consisting of halogen, methyl, hydrogen, and hydroxyl;
(c) $-R_aQ_aR_b$
wherein $Q_a=-O-$ or $-S-$;
wherein $R_a$ is alkylene of 0 to 6 carbons atoms, inclusive, which may be straight chain or branched;
wherein $R_b$ is alkyl of 0 to 8 carbon atoms, inclusive, which may be straight chain or branched;
(d) $-C(R_{iii})(R_{iv})-R_i$
wherein $R_{iii}$ and $R_{iv}$ are selected independently from the group consisting of
(i) H;
(ii) $CH_aZ_b$ where a+b=3, a=0 to 3, b=0+3, and wherein any Z is independently selected from the group consisting of halogen;
(e) haloalkyl of 1 to 8 carbon atoms, inclusive, and 1 to 6 halogen atoms, inclusive, straight chain or branched; and
wherein $R_6$ is
(a) H;
(b) alkyl from 1 to 4 carbon atoms, inclusive, straight chain or branched;
(c) halogen; but excluding the C-1 position amides, C-1 position alkanoates, and pharmaceutically acceptable C-1 position salts of (5S, 6R, 15S)-trihydroxy-7E, 9E, 11Z, 13E-eicosatetraenoic acid ($LXA_4$); and excluding C-5, C-6, and C-15 position alkanoates of $LXA_4$.

In one embodiment of this invention, the lipoxin analogs have the following structure II:

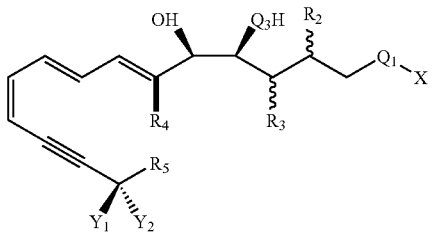

II wherein X is $R_1$, $OR_1$, or $SR_1$;
 wherein $R_1$ is
  (i) hydrogen;
  (ii) alkyl of 1 to 8 carbons atoms, inclusive, which may be straight chain or branched;
  (iii) cycloalkyl of 3 to 10 carbon atoms, inclusive;
  (iv) aralkyl of 7 to 12 carbon atoms;
  (v) phenyl;
  (vi) substituted phenyl

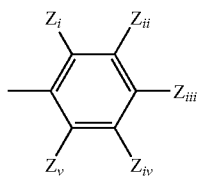

wherein $Z_i$, $Z_{iii}$ and $Z_v$ are each independently selected from the group consisting of —$NO_2$, —CN, —C(=O)—$R_1$, hydrogen, and —$SO_3H$;
   wherein $Z_{ii}$ and $Z_{iv}$ are each independently selected from the group consisting of halogen, methyl, hydrogen, and hydroxyl;
  (vii) detectable label molecule, such as but not limited to fluorescent labels; or
  (viii) alkenyl of 2 to 8 carbon atoms, inclusive, straight chain or branched;
wherein $Q_1$ is (C=O), $SO_2$ or (C=N);
wherein $Q_3$ is O, S or NH;
wherein one of $R_2$ and $R_3$ is hydrogen and the other is
 (a) H;
 (b) all of 1 to 8 carbon atoms, inclusive, which may be straight chain or branched;
 (c) cycloalkyl of 3 to 6 carbon atoms, inclusive;
 (d) alkenyl of 2 to 8 carbon atoms, inclusive, which may be straight chain or branched; or
 (e) $R_aQ_2R_b$
  wherein $Q_2$ is —O— or —S—;
  wherein $R_a$ is alkylene of 0 to 6 carbons atoms, inclusive, which may be straight chain or branched;
  wherein $R_b$ is alkyl of 0 to 8 carbon atoms, inclusive, which may be straight chain or branched;
wherein $R_4$ is
 (a) H;
 (b) alkyl of 1 to 6 carbon atoms, inclusive, which may be straight chain or branched;
wherein $Y_1$ or $Y_2$ is —OH, methyl, —H or —SH and wherein the other is
 (a) H;
 (b) $CH_aZ_b$
  where a+b=3, a 0 to 3, b=0 to 3
  Z is cyano, nitro, or halogen including F, Cl, Br, I;
 (c) alkyl of 2 to 4 carbon atoms, inclusive, straight chain or branched;
 (d) alkoxy of 1 to 4 carbon atoms, inclusive;
or $Y_1$ and $Y_2$ taken together are
 (a) =N; or
 (b) =O;
wherein $R_5$ is
 (a) alkyl of 1 to 9 carbon atoms which may be straight chain or branched;
 (b) —$(CH_2)_n$—$R_i$
  wherein n=0 to 4 and $R_i$ is
   (i) cycloalkyl of 3 to 10 carbon atoms, inclusive;
   (ii) phenyl; or
   (iii) substituted, phenyl

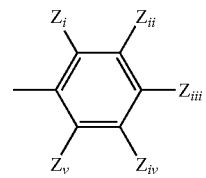

wherein $Z_i$, $Z_{iii}$, and $Z_v$ are each independently selected from the group consisting of hydrogen, —$NO_2$, —CN, —C(=O)—$R_1$, methoxy, and —$SO_3H$;
    wherein $Z_{ii}$ and $Z_{iv}$ are each independently selected from the group consisting of halogen, methyl, hydrogen, and hydroxyl;
 (c) —$R_aQ_aR_b$
  wherein $Q_a$=—O— or —S—; and
  wherein $R_a$ is alkylene of 0 to 6 carbons atoms, inclusive, which may be straight chain or branched;
  wherein $R_b$ is alkyl of 0 to 8 carbon atoms, inclusive, which may be straight chain or branched;
 (d) —C($R_{iii}$)($R_{iv}$)—$R_i$
  wherein $R_{iii}$ and $R_{iv}$ are selected independently from the group consisting of
   (i) H; and
   (ii) $CH_aZ_b$ where a+b=3, a=0 to 3, b=0+3 wherein any Z is selected from the group consisting of halogen.
 (e) haloalkyl of 1 to 8 carbon atoms, inclusive, and 1 to 6 halogen atoms, inclusive, straight chain or branched.

In one embodiment of this invention, the lipoxin analogs have the following structure III:

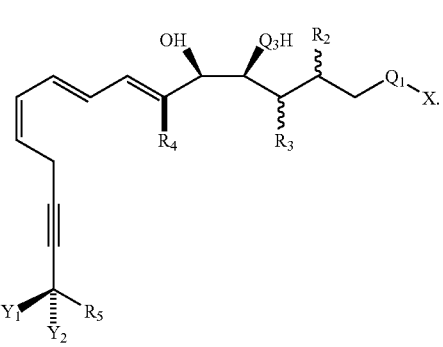

III wherein X is $R_1$, $OR_1$, or $SR_1$;
 wherein $R_1$ is (i) hydrogen;
(ii) alkyl of 1 to 8 carbons atoms, inclusive, which may be straight chain or branched;
(iii) cycloalkyl of 3 to 10 carbon atoms, inclusive;
(iv) aralkyl of 7 to 12 carbon atoms;
(v) phenyl;
(vi) substituted phenyl

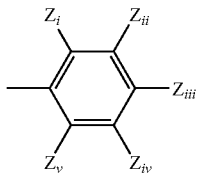

wherein $Z_i$, $Z_{iii}$, and $Z_v$ are each independently selected from the group consisting of —$NO_2$, —CN, —C(=O)—$R_1$, hydrogen, and —$SO_3H$;
wherein $Z_{ii}$ and $Z_{iv}$ are each independently selected from the group consisting of halogen, methyl, hydrogen, and hydroxyl;
(vii) detectable label molecule; or
(viii) alkenyl of 2 to 8 carbon atoms, inclusive, straight chain or branched;
wherein $Q_1$ is (C=O), $SO_2$ or (C=N);
wherein $Q_3$ is O, S or NH;
wherein one of $R_2$ and $R_3$ is hydrogen and the other is
(a) H;
(b) alkyl of 1 to 8 carbon atoms, inclusive, which may be straight chain or branched;
(c) cycloalkyl of 3 to 6 carbon atoms, inclusive;
(d) alkenyl of 2 to 8 carbon atoms, inclusive, which may be straight chain or branched; or
(e) $R_aQ_2R_b$
wherein $Q_2$ is —O— or —S—;
wherein $R_a$ is alkylene of 0 to 6 carbons atoms, inclusive, which may be straight chain or branched;
wherein $R_b$ is alkyl of 0 to 8 carbon atoms, inclusive, which may be straight chain or branched;
wherein $R_4$ is
(a) H; or
(b) alkyl of 1 to 6 carbon atoms, inclusive, which may be straight chain or branched;
wherein $Y_1$ or $Y_2$ is hydroxyl, methyl, hydrogen or thiol and wherein the other is
(a) H;
$CH_aZ_b$
where a+b=3, a=0 to 3, b=0 to 3
Z is cyano, nitro, or halogen [including F, Cl, Br, I];
(c) alkyl of 2 to 4 carbon atoms, inclusive, straight chain or branched;
(d) alkoxy of 1 to 4 carbon atoms, inclusive;
or $Y_1$ and $Y_2$ taken together are
(a) =N; or
(b) =O; and
wherein $R_5$ is
(a) alkyl of 1 to 9 carbon atoms which may be straight chain or branched;
(b) —$(CH_2)_n$—$R_i$
wherein n=0 to 4 and $R_i$ is
(i) cycloalkyl of 3 to 10 carbon atoms, inclusive;
(ii) phenyl;
(iii) substituted phenyl

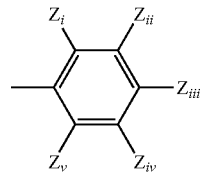

wherein $Z_i$, $Z_{iii}$, and $Z_v$ are each independently selected from the group consisting of hydrogen, —$NO_2$, —CN, —C(=O)—$R_1$, methoxy, and —$SO_3H$;
wherein $Z_{ii}$ and $Z_{iv}$ are each independently selected from the group consisting of halogen, methyl, hydrogen, and hydroxyl;
(c) —$R_aQ_aR_b$
wherein $Q_a$=—O— or —S—;
wherein $R_a$ is alkylene of 0 to 6 carbons atoms, inclusive, which may be straight chain or branched;
wherein $R_b$ is alkyl of 0 to 8 carbon atoms, inclusive, which may be straight chain or branched; or
(d) —C($R_{iii}$)($R_{iv}$)—$R_i$
wherein $R_{iii}$ and $R_{iv}$ are selected independently from the group consisting of
(i) H;
(ii) $CH_aZ_b$ where a+b=3, a=0 to 3, b=0+3 wherein any Z is selected from the group consisting of halogen.

In another embodiment of this invention, lipoxin analogs have the following structural formula IV:

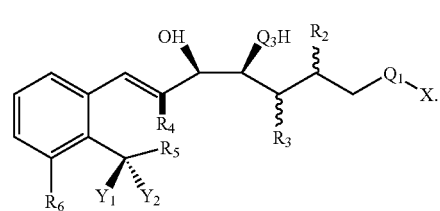

IV wherein X is $R_1$, $OR_1$, or $SR_1$;
wherein $R_1$ is
(i) hydrogen;
(ii) alkyl of 1 to 8 carbons atoms, inclusive, which may be straight chain or branched;
(iii) cycloalkyl of 3 to 10 carbon atoms, inclusive;
(iv) aralkyl of 7 to 12 carbon atoms;
(v) phenyl;
(vi) substituted phenyl

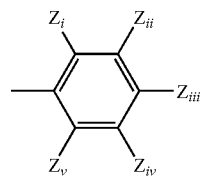

wherein $Z_i$, $Z_{iii}$, and $Z_v$ are each independently selected from the group consisting of —$NO_2$, —CN, —C(=O)—$R_1$, methoxy, hydrogen, and —$SO_3H$;

wherein $Z_{ii}$ and $Z_{iv}$ are each independently selected from the group consisting of halogen, methyl, hydrogen, and hydroxyl;
(vii) detectable label molecule; or
(viii) alkenyl of 2 to 8 carbon atoms, inclusive, straight chain or branched;

wherein $Q_1$ is (C=O), $SO_2$ or (CN);
wherein $Q_3$ is O, S or NH;
wherein one of $R_2$ and $R_3$ is hydrogen and the other is
(a) H;
(b) alkyl of 1 to 8 carbon atoms, inclusive, which may be straight chain or branched;
(c) cycloalkyl of 3 to 6 carbon atoms, inclusive;
(d) alkenyl of 2 to 8 carbon atoms, inclusive, which may be straight chain or branched; or
(e) $R_aQ_2R_b$
wherein $Q_2$ is —O— or —S—;
wherein $R_a$ is alkylene of 0 to 6 carbons atoms, inclusive, which may be straight chain or branched;
wherein $R_b$ is alkyl of 0 to 8 carbon atoms, inclusive, which may be straight chain or branched;

wherein $R_4$ is
(a) H; or
(b) alkyl of 1 to 6 carbon atoms, inclusive, which may be straight chain or branched;

wherein $Y_1$ or $Y_2$ is —OH, methyl, or —SH and wherein the other is
(a) H;
(b) $CH_aZ_b$
where a+b=3, a=0 to 3, b=0 to 3,
Z is cyano, nitro, or halogen;
(c) alkyl of 2 to 4 carbon atoms, inclusive, straight chain or branched; or
(d) alkoxy of 1 to 4 carbon atoms, inclusive;
or $Y_1$ and $Y_2$ taken together are
(a) =N; or
(b) =O;

wherein $R_5$ is
(a) alkyl of 1 to 9 carbon atoms which may be straight chain or branched;
(b) —$(CH_2)_n$—$R_i$
wherein n=0 to 4 and $R_i$ is
(i) cycloalkyl of 3 to 10 carbon atoms, inclusive;
(ii) phenyl; or
(iii) substituted phenyl

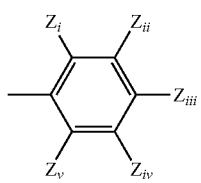

wherein $Z_i$, $Z_{iii}$ and $Z_v$ are each independently selected from the group consisting of hydrogen, —$NO_2$, —CN, —C(=O)—$R_1$, methoxy, and —$SO_3H$;
wherein $Z_{ii}$ and $Z_{iv}$ are each independently selected from the group consisting of halogen, methyl, hydrogen, and hydroxyl;
(c) $R_aQ_aR_b$
wherein $Q_a$=—O— or —S—;
wherein $R_a$ is alkylene of 0 to 6 carbons atoms, inclusive, which may be straight chain or branched;
wherein $R_b$ is alkyl of 0 to 8 carbon atoms, inclusive, which may be straight chain or branched;
(d) —C($R_{iii}$)($R_{iv}$)—$R_i$
wherein $R_{iii}$ and $R_{iv}$ are selected independently from the group consisting of
(i) H; or
(ii) $CH_aZ_b$ where a+b=3, a=0 to 3, b=0+3, and wherein any Z is selected from the group consisting of halogen; or
(e) haloalkyl of 1 to 8 carbon atoms, inclusive, and 1 to 6 halogen atoms, inclusive, straight chain or branched; and wherein $R_6$ is
(a) H;
(b) alkyl from 1 to 4 carbon atoms, inclusive, straight chain or branched; or
(c) halogen.

In another embodiment of this invention, lipoxin analogs have the following structural formula V:

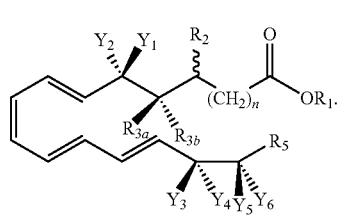

wherein $R_1$ is
(i) hydrogen;
(ii) alkyl of 1 to 8 carbons atoms, inclusive, which may be straight chain or branched;
(iii) cycloalkyl of 3 to 10 carbon atoms, inclusive;
(iv) aralkyl of 7 to 12 carbon atoms;
(v) phenyl;
(vi) substituted phenyl

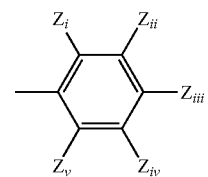

wherein $Z_i$, $Z_{iii}$, and $Z_v$ are each independently selected from the group consisting of —$NO_2$, —CN, —C(=O)—$R_1$, hydrogen, and —$SO_3H$;
wherein $Z_{ii}$ and $Z_{iv}$ are each independently selected from the group consisting of halogen, methyl, hydrogen, and hydroxyl;
(vii) detectable label molecule; or
(viii) alkenyl of 2 to 8 carbon atoms, inclusive, straight chain or branched;

wherein n=1 to 10, inclusive;
wherein $R_2$, $R_{3a}$, and $R_{3b}$ are independently selected from
(a) H;
(b) alkyl of 1 to 8 carbon atoms, inclusive, which may be straight chain or branched;
(c) cycloalkyl of 3 to 6 carbon atoms, inclusive;
(d) alkenyl of 2 to 8 carbon atoms, inclusive, which may be straight chain or branched; or
(e) $R_aQ_2R_b$ wherein $Q_2$ is —O— or —S—;
wherein $R_a$ is alkylene of 0 to 6 carbons atoms, inclusive, which may be straight chain or branched; and wherein Pb is alkyl of 0 to 8 carbon atoms, inclusive, which may be straight chain or branched;

wherein $Y_1$ or $Y_2$ is —OH, methyl, hydrogen, or —SH and wherein the other is
(a) H;
(b) $CH_aZ_b$
where a+b=3, a 0 to 3, b=0 to 3, and
Z is cyano, nitro, or halogen;
(c) alkyl of 2 to 4 carbon atoms, inclusive, straight chain or branched;
(d) alkoxy of 1 to 4 carbon atoms, inclusive, straight chain or branched;
or $Y_1$ and $Y_2$ taken together are
(a) =N; or
(b) =O; —
wherein $Y_3$ or $Y_4$ is —OH, methyl, hydrogen, or —SH and wherein the other is
(a) H;
(b) $CH_aZ_b$
wherein a+b=3, a=0 to 3, b=0 to 3,
and any Z is cyano, nitro, or halogen;
(c) alkyl of 2 to 4 carbon atoms, inclusive, straight chain or branched;
(d) alkoxy of 1 to 4 carbon atoms, inclusive, straight chain or branched;
or $Y_3$ and $Y_4$ taken together are
(a) =N; or
(b) =O;
wherein $Y_5$ or $Y_6$ is —OH, methyl, hydrogen, or —SH and wherein the other is
(a) H;
(b) $CH_aZ_b$
where a+b=3, a=0 to 3, b=0 to 3
Z is cyano, nitro, or halogen;
(c) alkyl of 2 to 4 carbon atoms, inclusive, straight chain or branched;
(d) alkoxy of 1 to 4 carbon atoms, inclusive, straight chain or branched;
or $Y_5$ and $Y_6$ taken together are
(a) =N; or
(b) =O;
wherein $R_5$ is
(a) alkyl of 1 to 9 carbon atoms which may be straight chain or branched;
(b) —$(CH_2)_n$—$R_i$
wherein n=0 to 4 and $R_i$ is
(i) cycloalkyl of 3 to 10 carbon atoms, inclusive;
(ii) phenyl; or
(iii) substituted phenyl

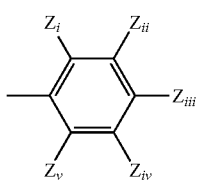

wherein $Z_i$, $Z_{iii}$, and $Z_v$ are each independently selected from the group consisting of hydrogen, —$NO_2$, —CN, —C(=O)—$R_1$, and —$SO_3H$;

wherein $Z_{ii}$ and $Z_{iv}$ are each independently selected from the group consisting of halogen, methyl, hydrogen, methoxy, and hydroxyl;
(c) —$R_aQ_aR_b$
wherein $Q_a$=—O— or —S—; and
wherein $R_a$ is alkylene of 0 to 6 carbons atoms, inclusive, which may be straight chain or branched;
wherein $R_b$ is either alkyl of 0 to 8 carbon atoms, inclusive, which may be straight chain or branched or substituted phenyl;
(d) —C($R_{iii}$)($R_{iv}$)—$R_i$
wherein $R_{iii}$ and $R_{iv}$ are selected independently from the group consisting of
(i) H; or
(ii) $CH_aZ_b$ where a+b=3, a=0 to 3, b=0+3, and
wherein any Z is selected from the group consisting of halogen; or
(e) haloalkyl of 1 to 8 carbon atoms, inclusive, and 1 to 6 halogen atoms, inclusive, straight chain or branched; but excluding the C-1 position amides, C-1 position alkanoates, and pharmaceutically acceptable C-1 position salts of (5S, 14R, 15S)-trihydroxy-6E, 8Z, 10E, 12E-eicosatetraenoic acid ($LXB_4$); C-5, C-6, and C-5 position alkanoates of $LXB_4$.

In another embodiment of this invention, lipoxin analogs have the structural formula VI:

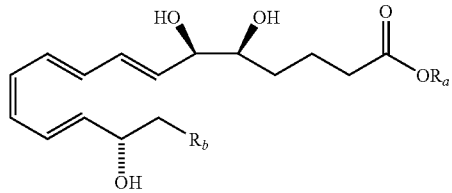

wherein $R_a$ is selected from the group
(a) H; or
(b) alkyl of 1 to 8 carbon atoms;
wherein $R_b$ selected from the group consisting of:

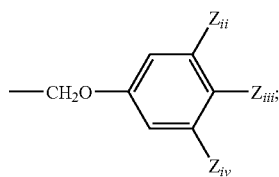

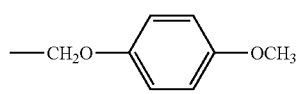

In another preferred embodiment of this invention, lipoxin analogs have the following structural formula VII:

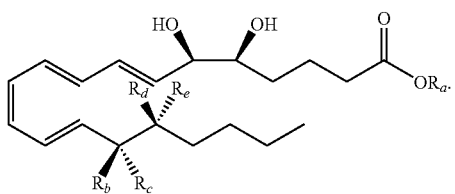

wherein $R_a$ is selected from the group
(a) H; or
(b) alkyl of 1 to 8 carbon atoms;
wherein $R_b$ and $R_c$ are independently selected from the group
(a) H;
(b) hydroxyl, or thiol;
(c) methyl or halomethyls including —$CF_3$ and —$CH_2F$;
(d) halogen;
(e) alkoxy of 1 to 3 carbon atoms, including methoxy;
wherein $R_d$ and $R_e$ are selected independently from the group
(a) H;
(b) hydroxyl, or thiol;
(c) methyl or halomethyl including —$CF_3$, and —$CH_2F$;
(d) halogen;
(e) alkoxy of 1 to 3 carbon atoms, inclusive, including methoxy; or
(f) alkyl or haloalkyl of 2 to 4 carbon atoms, inclusive, which may be straight chain or branched; but excluding the C-1 position amides, C-1 position alkanoates, and pharmaceutically acceptable C-1 position salts of (5S, 6R, 15S)-trihydroxy-7E, 9E, 11Z, 13E-eicosatetraenoic acid ($LXA_4$); C-5, C-6, and C-15 position alkanoates of $LXA_4$.

In another preferred embodiment of this invention, the lipoxin analogs have the structural formula VIII:

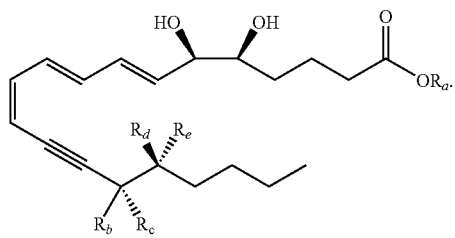

wherein $R_a$ is selected from the group
(a) H; or
(b) alkyl of 1 to 8 carbon atoms;
wherein $R_b$ and $R_c$ are independently selected from the group
(a) H;
(b) hydroxyl or thiol;
(c) halomethyl, including $CF_3$;
(d) halogen;
(e) alkyl of 1 to 3 carbon atoms, inclusive, straight chain or branched; or
(f) alkoxy of 1 to 3 carbon atoms, inclusive;
wherein $R_d$ and $R_e$ are selected independently from the group
(a) H;
(b) hydroxyl, or thiol;
(c) methyl or halomethyl including —$CF_3$ and —$CH_2F$;
(d) halogen;
(e) alkoxy of 1 to 3 carbon atoms, inclusive, including methoxy; or
(f) alkyl or haloalkyl of 2 to 4 carbon atoms, inclusive, which may be straight chain or branched.

In another preferred embodiment of this invention, the lipoxin analogs have the structural formula IX:

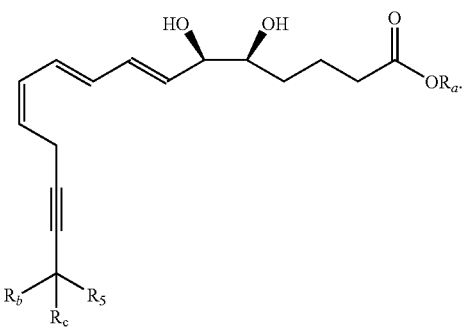

wherein $R_a$ is selected from the group
(a) H; or
(b) alkyl of 1 to 8 carbon atoms;
wherein $R_b$ and $R_c$ are independently selected from the group
(a) H;
(b) hydroxyl or thiol;
(c) halomethyl, including $CF_3$ and $CH_2F$;
(d) halogen;
(e) alkyl of 1 to 3 carbon atoms, inclusive, straight chain or branched;
(f) alkoxy of 1 to 3 carbon atoms, inclusive; and
wherein $R_5$ is
(a) alkyl of 1 to 9 carbon atoms which may be straight chain or branched;
(b) —$(CH_2)_n$—$R_i$
wherein n=0 to 4 and $R_i$ is
(i) cycloalkyl of 3 to 10 carbon atoms, inclusive;
(ii) phenyl; or
(iii) substituted phenyl

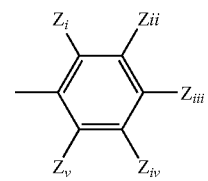

wherein $Z_i$, $Z_{iii}$, and $Z_v$ are each independently selected from the group consisting of hydrogen, —$NO_2$, —CN, —C(=O)—$R_1$, and —$SO_3H$;
wherein $Z_{ii}$ and $Z_{iv}$ are each independently selected from the group consisting of halogen, methyl, hydrogen, methoxy, and hydroxyl;
(c) —$R_a Q_a R_b$
wherein $Q_a$=—O— or —S—;
wherein $R_a$ is alkylene of 0 to 6 carbons atoms, inclusive, which may be straight chain or branched;

wherein $R_b$ is either alkyl of 0 to 8 carbon atoms, inclusive, which may be straight chain or branched or substituted phenyl;
(d) —C($R_{iii}$)($R_{iv}$)—$R_i$
wherein $R_{iii}$ and $R_{iv}$ are selected independently from the group consisting of
(i) H; or
(ii) $CH_aZ_b$ where a+b=3, a=0 to 3, b=0+3 wherein any Z is selected from the group consisting of halogen; or
(e) haloalkyl of 1 to 8 carbon atoms, inclusive, and 1 to 6 halogen atoms, inclusive, straight chain or branched.

In another preferred embodiment, the compounds have the structural formula X:

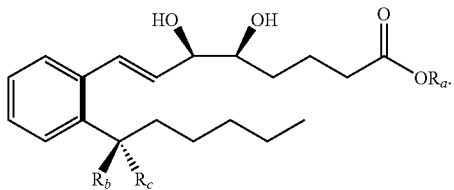

X wherein $R_a$ is selected from the group
(a) H; or
(b) alkyl of 1 to 8 carbon atoms, inclusive, straight chain or branched; and
wherein $R_b$ and $R_c$ are independently selected from the group
(a) H;
(b) hydroxyl or thiol;
(c) halomethyl, including, for example, $CF_3$;
(d) halogen;
(e) alkyl of 1 to 3 carbon atoms, inclusive, straight chain or branched;
(f) alkoxy of 1 to 3 carbon atoms, inclusive, including methoxy.

In another preferred embodiment, the compounds have the structural formula XI:

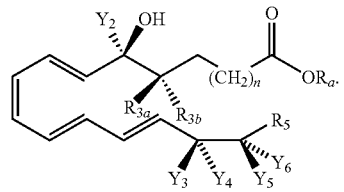

XI wherein $R_a$ is
(i) hydrogen;
(ii) alkyl of 1 to 8 carbons atoms, inclusive, which may be straight chain or branched; or
(iii) detectable label molecule;
wherein n=1 to 10, inclusive;
wherein $Y_2$, $R_{3a}$, and $R_{3b}$ are independently selected from
(a) H;
(b) alkyl of 1 to 8 carbon atoms, inclusive, which may be straight chain or branched;
(c) cycloalkyl of 3 to 6 carbon atoms, inclusive;
(d) alkenyl of 2 to 8 carbon atoms, inclusive, which may be straight chain or branched; or
(e) $R_aQ_2R_b$
wherein $Q_2$ is —O— or —S—;
wherein $R_a$ is alkylene of 0 to 6 carbons atoms, inclusive, which may be straight chain or branched; and
wherein $R_b$ is alkyl of 0 to 8 carbon atoms, inclusive, which may be straight chain or branched;
wherein $Y_1$ is —OH, methyl, or —SH;
wherein $Y_2$ is
(a) H;
(b) $CH_aZ_b$
where a+b=3, a=0 to 3, b=0 to 3
Z is halogen; or
(c) alkyl of 2 to 4 carbon atoms, inclusive, straight chain or branched;
wherein $Y_3$ and $Y_5$ are independently selected from the group consisting of:
(a) H;
(b) $CH_aZ_b$
wherein a+b=3, a=0 to 3, b=0 to 3
and any Z is cyano, nitro, or halogen; or
(c) alkyl of 2 to 4 carbon atoms, inclusive, straight chain or branched;
wherein $Y_4$ and $Y_6$ are independently selected from the group consisting of:
(a) H;
(b) alkyl of 2 to 4 carbon atoms, inclusive, straight chain or branched;
(c) alkoxy of 1 to 4 carbon atoms, inclusive, straight chain or branched; or
(d) hydroxyl or thiol; and
wherein $R_5$ is
(a) alkyl of 1 to 9 carbon atoms which may be straight chain or branched;
(b) —$(CH_2)_n$—$R_i$
wherein n=0 to 3 and $R_i$ is
(i) cycloalkyl of 3 to 10 carbon atoms, inclusive;
(ii) phenyl;
(iii) substituted phenyl

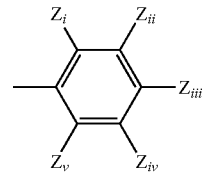

wherein $Z_{ii}$ and $Z_{iv}$ are each independently selected from the group consisting of halogen, methyl, hydrogen, methoxy, and hydroxyl;
(c) $R_aQ_aR_b$
wherein $Q_a$=—O— or —S—;
wherein $R_a$ is alkylene of 0 to 6 carbons atoms, inclusive, which may be straight chain or branched;
wherein $R_b$ is

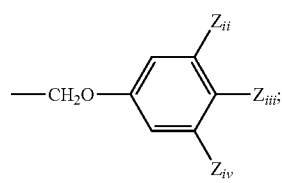

-continued

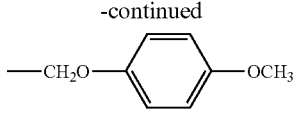

(d) haloalkyl of 1 to 8 carbon atoms, inclusive, and 1 to 6 halogen atoms, inclusive, straight chain or branched; or but excluding the C-1 position amides, C-1 position alkanoates, and pharmaceutically acceptable C-1 position salts of (5S, 14R, 15S)-trihydroxy-6E, 8Z, 10E, 12E-eicosatetraenoic acid (LXB$_4$); C-5, C-6, and C-5 position alkanoates (acetates) of LXB$_4$.

In the most preferred embodiment of this invention, the compounds of this invention have the following structural formulas:

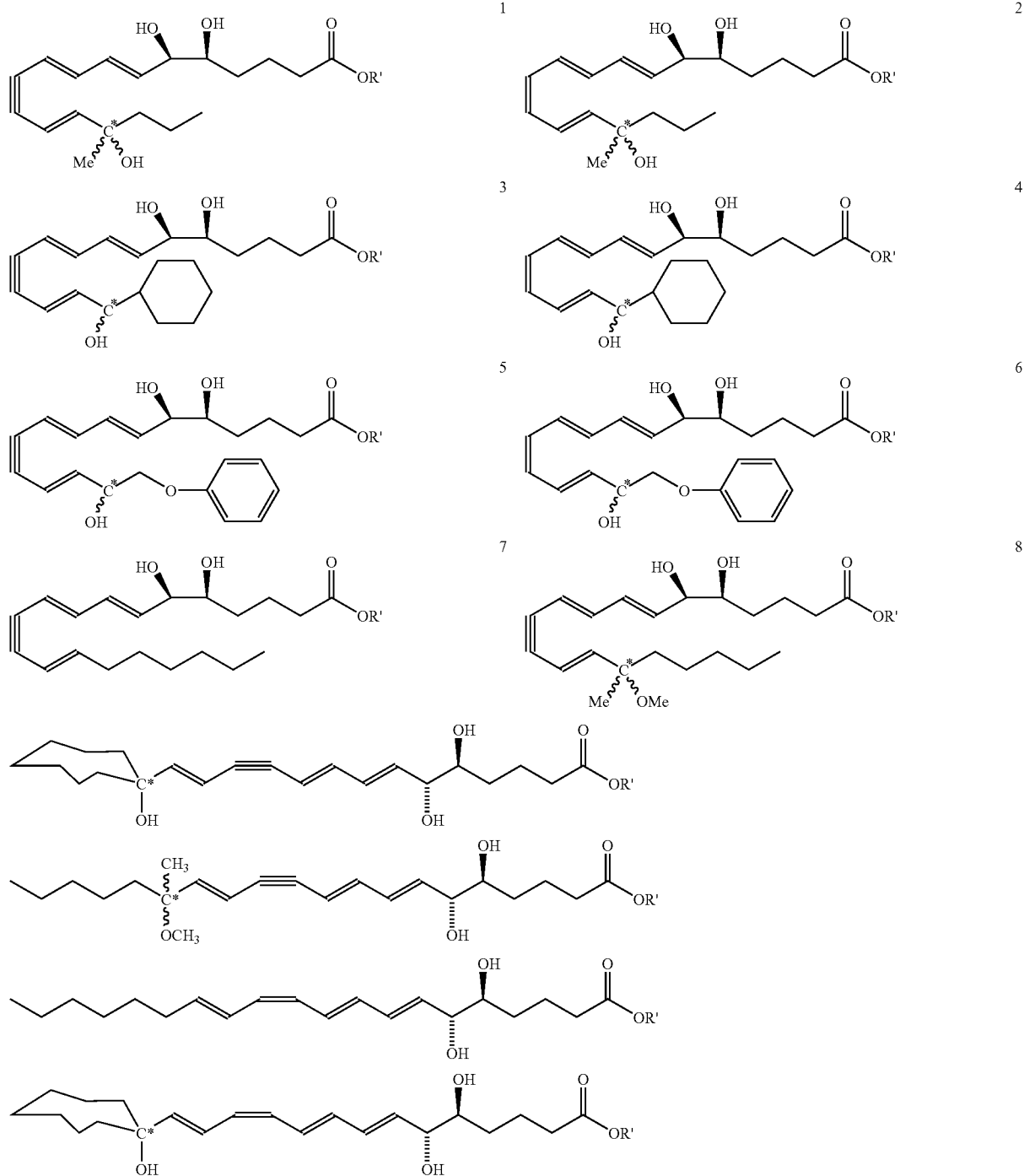

where R' is H or CH$_3$;

and where the substituents at C* are in the R configuration.

In other preferred embodiments of this invention, the compounds of this invention have the following structural formulas:

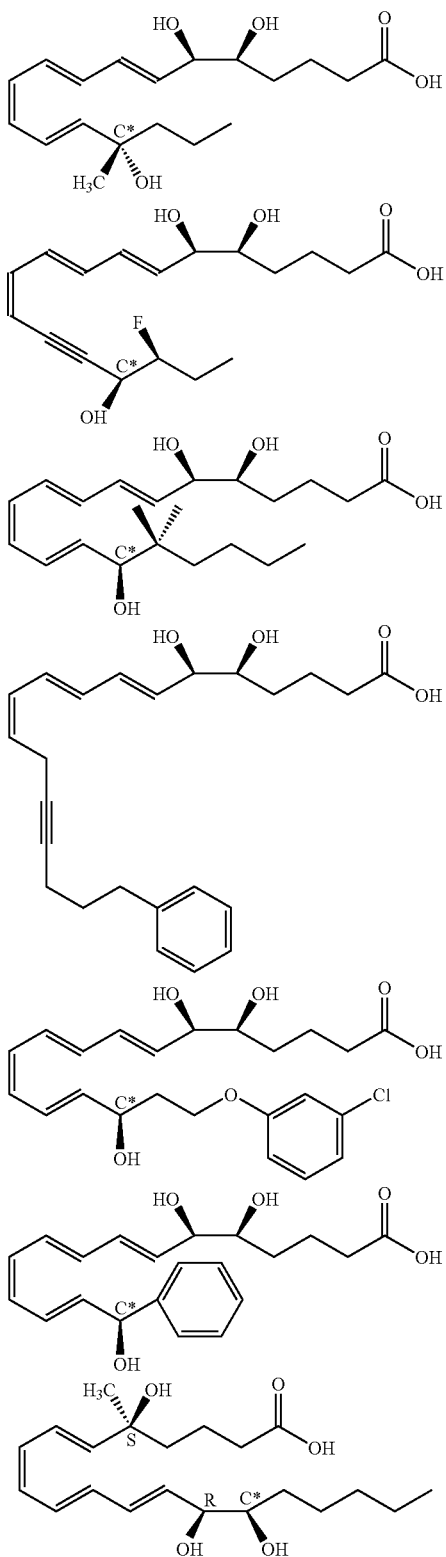

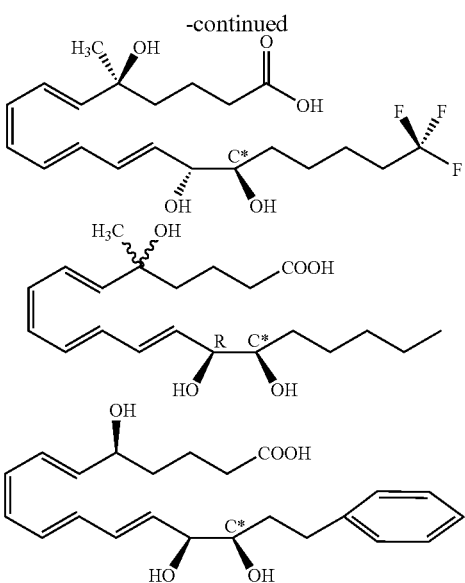

where the substituents at the C* are in the R configuration.

Method for Making Lipoxin Compounds

Preferred compounds can be made as specifically described in the following Example 1. Other compounds of this invention can be made by combined strategies for lipoxin (LX) and prostaglandin analog synthesis using standard chemical methods such as selective hydrogenation, Pd(0) Cu(I) coupling, Wittig-type coupling, Sharpless epoxidation, and asymmetric reductions following coupling of the major intermediates described below and in the literature to generate the stable LX analogs of this invention. (Webber, S. E. et al. (1988) Adv. Exp. Med. Biol. 229:61; Radüchel, B. and Vorbrüggen, H. (1985) Adv. Prostaglandin Thromboxane Leukotriene Res. 14:263; and Nicolaou, K. C. et al. (1991) Angew Chem. Int. Ed. Engl. 30:1100). Geometrical variations can be accomplished e.g. as described in U.S. Pat. No. 4,576,758 and Nicolaou, K. C. (1989) J. Org. Chem. 54: 5527.

As shown below, LX analog compounds comprising subgenus 1 in Scheme I can be prepared as three major fragments (A, B, and C), which can then be combined to form the total molecule.

Scheme I

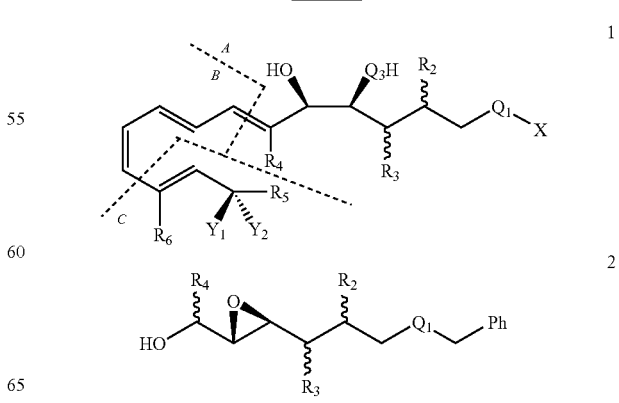

Synthesis of the epoxy-alcohol for precursor fragment 2 can be generated with substitutents $R_2$, $R_3$ and $R_4$ selected from hydrogen, phenyl, halogen or methyl. Each of these respective epoxy-alcohols may be transformed into phenyl urethane derivatives as 3.

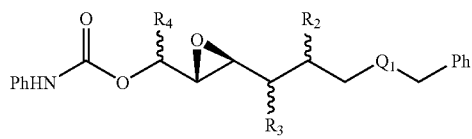

3 with PhNCO, pyrimidine and $CH_2Cl_2$ followed by Lewis acid catalysis by $SN^2$ opening to give a 1,2 cyclic carbonate that contains the vicinal diol at C-6 in the (R) configuration required for binding and C-5 in the (S) configuration also established for bioactivity and binding at a recognition site. These alcohols are next protected to generate the precursor A fragment as 4.

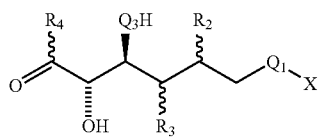

4

These A fragments can now be coupled to the fragment B intermediate, a phosphonium bromide 5 as in Webber, S. E. et al., (1988) Adv. Exp. Med. Biol. 229:61 in gram quantities to generate the combined A+B fragment products 6.

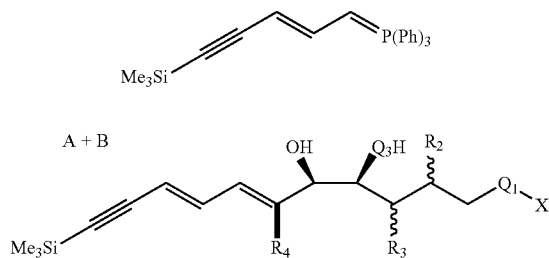

Fragment C intermediates from Scheme I are generated in parallel to preparation of A-B couplings. In these C fragments, substitutions at $Y_1$ and/or $Y_2$ are methyl, methoxy, hydrogen, cyano, nitro, or halogen; see specific example 3. Thus, carrying 15-methyl and/or, for example, 16-methyl or 16-phenoxy-derivatives permits these substituted-$LXA_4$ analogs to be not susceptible to dehydrogenation.

Thus, the C fragments carrying the preferred resistance to enzymatic oxidation and/or dehydrogenation may be converted by protection of key sites, followed by bromination to give vinyl bromide products of fragment C such as 6b that is coupled to 6 by using catalytic amounts of $P(Ph_3)_4$ and CuI to generate the complete backbone structure of the $LXA_4$ analogs of genus formula I. This scheme is further illustrated by the following Examples.

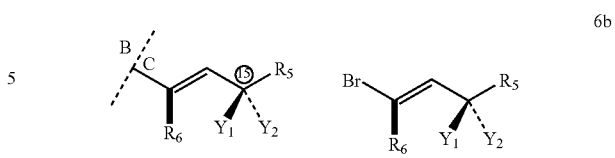

Scheme II.

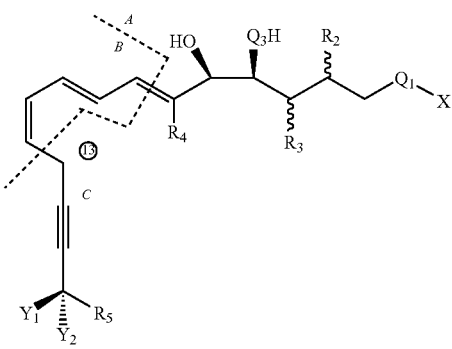

The compounds of this invention within subgenus formulas II and III may be made synthesized in a similar manner.

Compounds in genuses II and III are generated by first individually preparing substituted compounds of fragment A that are each coupled as in Scheme I to individually prepared fragment B to generate 7 or $A_1+B_1$ fragments possessing individual substitutions at X, $Q_1$, $R_2$, $R_3$, and $R_4$ as indicated.

7

$A_1 + B_1$

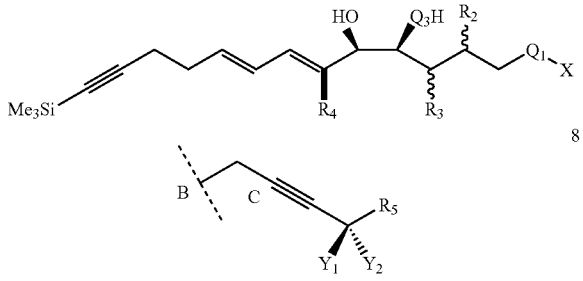

8

The $C_1$ fragment 8 carrying the acetylenic group C-14,15 and the ω-C-20 end substitutions will each be generated as shown above for structure 6 prostaglandin analogs and converted to their corresponding vinyl bromide products as in (KCN JAC 1985, Webber) to yield brominated products of each individual substituted fragment $C_1$ or 8 species that are suitable for coupling to 20 using catalytic amounts of $P(Ph_3)_4$ and CuI to generate the combined products of the acetylenic-$LXA_4$ analog class. Each of the final products may then be subject to gradient RP-HPLC using rapid diode array detection (as in Serhan, C. N., Methods in Enzymology) for purification. The presence of the modification at C-15 thru C-20 of $LXA_4$ can alter metabolism by dehydrogenases and oxidases by providing steric hindrance, stable prostaglandin analogs carrying C-15 to ω-end substitutions have been prepared and are not metabolized by dehydrogenases (Radüchel, B. and Vorbrüggen, H. (1985) Adv. Prostaglandin Thromboxane Leukotriene Res. 14:263 and Vorbrüggen, H. et al. In: Chemistry, Biochemistry, and Pharmacological Activity of Prostanoids (Roberts, S. M., Scheinmann, F. eds.). Oxford: Pergamon Press).

The cyclo-LXA$_4$ compounds of this invention within genus formula IV may be made in the following manner.

Scheme III.

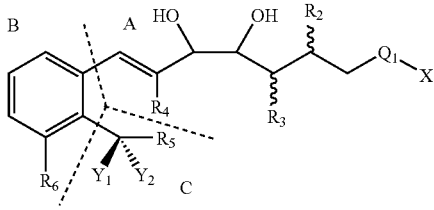

9

The parent compound of this class is also subject to a similar total synthesis strategy and is assigned three main fragments A, B, and C in structure 30. A precursor for fragment A may be prepared by routes used in Nicolaou, K. C. (1989) J. Org. Chem. 54:5527 to prepare 10 in the synthesis of 7-cis, 11-trans-LXA$_4$ methyl ester.

10

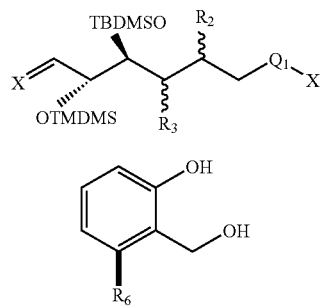

11

Fragment B in 30 can be obtained via the precursor 11 or saligenin-([O-hydroxybenzylalcohol) as generated in (Vorbrüggen et al., p. 353). The benzyl alcohol 11 is reacted with 10 (1:1) in the presence of NaH in DMF to give 12. This key intermediate is silylated in BSTFA followed by coupling with individual fragments designed for C precursors

12

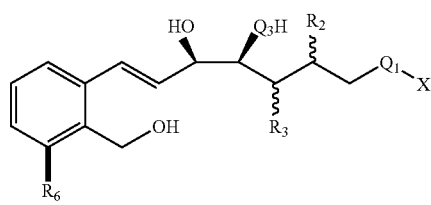

13 can then be coupled to vinyl brominate fragment C of given individual design by treating the bromite precursor with 4.0 equivalents of AgNO$_3$, then 7.0 equiv. of KCN, EtOH/THF/H$_2$O (1:1:1), 0⇒25° C., 2-4 h. the individual products are then subject to Lindlar cat. for selective catalytic mild hydrogenation in CH$_2$Cl$_2$ 2-3 h to give individual compounds belonging to the genus IV. Each can be saponified in LiOH/THF to give corresponding free acids after isolation by RP-HPLC.

13

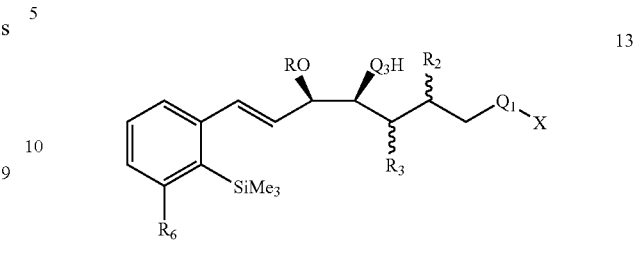

The invention of genus IV compounds is illustrated further below, the synthesis of 15(±)methyl-cyclo-LXA$_4$ methyl ester and corresponding free acid.

The compounds of this invention within genus formula V may be made in the following manner. Several systems studied with LXB$_4$ indicate that several sites within the natural compound are required for bioactivity (Serhan, C. N. (1991) J. Bioenerg and Biomembr. 23:105). These sites include the C-14 alcohol in the (R) configuration and the double bond at C-8,9 of the tetraene in the cis configuration. In addition, based on metabolic studies resulting in the instant invention, several key addition sites have been identified as being necessary to preserve LXB$_4$ bioactivity. These include preserving the C-15 alcohol from dehydrogenase activity (i.e., block 5-oxo-LXB$_4$ formation); maintaining both the Δ8 bond and 14(R) alcohol; and preventing reduction of Δ6-7 double bond and β/ω-oxidations of the resultant compounds.

Scheme IV

14

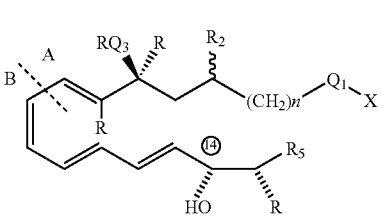

Thus, genus V (14) maintains the regions of LXB$_4$ which are necessary for its bioactivity, but modifies the regions available to metabolic degradation. Again, a retrosynthetic analysis gives priority to three key fragments A, B and C designated in 14. Coupling of key intermediates to generate members of the LXB$_4$ analog class uses standard techniques as outlined for LXA$_4$ and its analogs namely, selective hydrogenation (to generate 8-cis geometry); Pd(0)-Cn(I) coupling to join A & B fragments carrying unique substitutions; Wittig-type coupling to join C fragments that carry the required substitutions and Sharpless epoxidation to yield the 14(R) vicinal alcohol (see ref. Nicolaou, K. C. et al. (1991) Angew. Chem. Int. Ed. Engl. 30:1100.), ref.; Weber, S. E. et al. (1988) Adv. Exp. Med. Biol. 229:61 Ed. Wong, P. K. and Serhan, C. N.) and those cited within). Thus by using a similar strategy to LXA$_4$ analogs and the construction of native LXB$_4$ the specific analogs can be obtained.

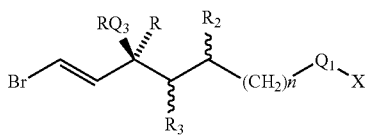

15

The A fragments of 15 that carry substitutions at $R_2$, $R_6$, $R_7$ that can be (H, $CH_3$, $OCH_3$, phenyl, halo-substituted phenyl are generated by standard methods from, for example 16 where =$CH_2$ of increasing chain length.

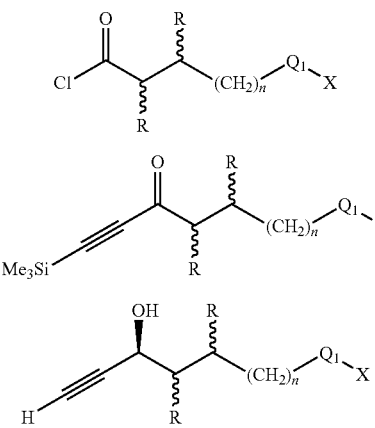

16

17

18

Compound 16 is converted to the vinyl bromide 15 as in (Nicolaou K. C. et al. (1991) Angew. Chem. Int. Ed. Engl. 30: 1100-16.) via a trimethylsilyl acetylenic intermediate 17 that is reduced by pinanyl-9BBN then n-$BuN_4NF$ in THF to yield 18 than is now submitted for bromination after protecting essential moieties such the alcohol to give 15 (fragment A).

The fragment C in 14 is generated from compound 19 with the $R_5$ substitutions as indicated.

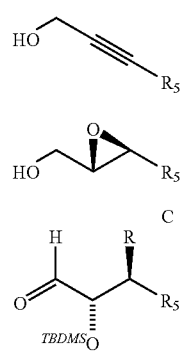

19

20

21

The acetylenic alcohol 19 is then reduced in LAH followed by Sharpless asymmetric epoxidation to generate 20 that is isolated by RP-HPLC to yield the (+) isomer that is used to generate the required C-14 alcohol of $LXB_4$ analogs in the (R) configuration compound 20 is transformed to the corresponding aldehyde 21 after protection of the substituted groups carried at $R_4$ and $R_5$ as well as the alcohol using PCC in methylene chloride. (Nicolaou, K. C. et al. (1991) Angew. Chem. Int. Ed. Engl. 30:1100).

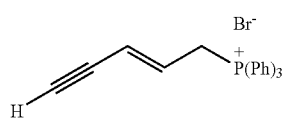

22

The phosphonium salt 22 can be prepared as in Ref.; (Weber, S. E. et al. (1988) Adv. Exp. Med. Biol. 229:61, Ed. Wong, P. K. and Serhan, C. N.) and used here to generate the B-C fragment coupling via a Wittig-type coupling to give 23 carrying the designated substitutions in the group of 23 where $R_4$ and $R_5$ carry substitutions. This cis double bond of 23 can be is isomerized to give the trans isomer using 12 as a catalyst to give the parent precursor form of 14 as 24.

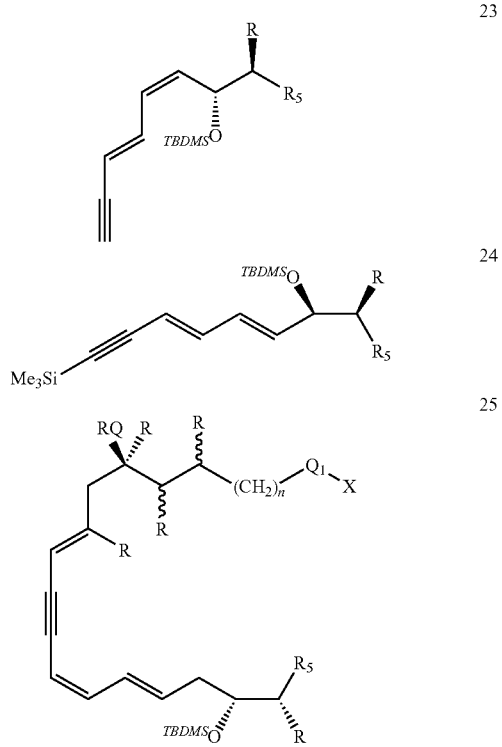

23

24

25

Then coupling of 24 to 15 is accomplished by Pd(O)—Cu(I) coupling to give the acetylenic precursor of 14 designated 25. Following selective Lindlar catalytic hydrogenation the individual $LXB_4$ analogs can be further purified via RP-HPLC used the tetraene skeleton as a convenient means to isolate individual products employing rapid diode array detection (Serhan, C. N. (1990) Meth. Enzymol. 187:167).

Utilities

The compounds of this invention have the biological activity of natural LXs, but are more resistant to degradation or alternatively inhibit the degradation of natural LXs. The disclosed compounds therefore have utility as pharmaceuticals for treating or preventing a number of diseases or conditions associated with inadequate or inappropriate LX mediated cellular response in a subject.

Based on the anti-proliferative effect of the disclosed 15-epi-lipoxin compounds, the invention provides methods for ameliorating undesired cell proliferation by contacting cells with a pharmaceutical composition including an effective amount of the substantially purified 15-epi-LX compound and a pharmaceutically acceptable carrier. The cell can be contacted in vivo and/or in vitro. Alternatively, cells can be removed from a subject; contacted with the substantially purified 15-epi-lipoxin compound of the present invention ex vivo and implanted in the subject. The invention also provides a method for ameliorating a cell proliferative disorder in a subject including administering an effective amount of a substantially purified 15-epi-LX compound.

The effective amount is ordinarily the amount which is required to assure sufficient exposure to a target cell population. Such an amount will ordinarily depend upon the nature of the 15-epi-LX compound, the mode of administration, the severity of the undesired cell proliferation or cell proliferative disorder and other factors considered by a person of ordinary skill when determining a dosage regimen.

Target cells to be contacted can be undergoing cancerous and/or tumorous growth. Alternatively, target cells can be undergoing abnormal cell proliferation in response to a stimulus, such as restenosis; and/or target cells can consist of transformed cells having a genetic makeup altered from that of the original cells.

Preferred target cells include epithelial cells, leukocytes, endothelial cells, and/or a fibroblasts.

Based on the stimulatory action of LXs on selected cells, the invention also provides methods for treating a subject with a myeloid suppressive disorder by administering to the subject an effective amount of a pharmaceutical composition comprising a LX analog. The effective amount is ordinarily that amount which is required to assure sufficient exposure to the target cell population. Such an amount will ordinarily depend upon the nature of the analog, the mode of administration, the severity of the myeloid suppression, and other factors considered by a person of ordinary skill when determining a dosage regimen.

Therapeutic use of a cell proliferative LX analog also includes removing cells from a subject, stimulating cell growth in vitro, and reintroducing the enhanced cell preparation, in whole or in part, into the subject. Additional therapeutic agents (e.g. cytokines such as GM-CSF) may be optionally used in conjunction with the LX during stimulation or in conjunction with the introduction of the cell preparation.

In another embodiment, the compounds of this invention are used to treat or prevent inflammation or an inflammatory response. $LXA_4$ inhibits the activation of leukocytes which are mediators of inflammation. The $LXA_4$-induced effect includes inhibition of leukocyte migration, generation of reactive oxygen species, and the formation of pro-inflammatory mediators involved in tissue swelling. (Raud, J. et al. (1991) Adv. Exp. Med. Biol. 314:185. Cell-Cell Interactions in the Release of Inflammation Mediators vol. 314) $LXB_4$ exhibits radioprotective actions, such as preventing diarrhea and ataxia, in an in vivo assay with mouse hematopoietic stem cells. (Walken, T. L. Jr., (1988) J. Radiat. Res. 29:255)

The leukocyte-mediated inflammation or inflammatory responses cause or contribute to a wide variety of diseases and conditions including various forms of asthma and arthritis. Included within the present invention are inflammatory responses to physical injury, such as physical trauma, radiation exposure, and otherwise.

In another embodiment, the compounds of this invention are used to treat or prevent inflammation by antagonizing the action of leukotrienes. $LXA_4$ inhibits $LTB_4$-induced inflammation, blocking both plasma leakage and leukocyte migration in an in vivo assay of the hamster cheek pouch. (Hedqvist, P. et al. (1989) Acta Physiol. Scand. 137 : 571.) Plasma leakage and leukocyte migration are key events in both wound healing and inflammation. $LXA_4$ also antagonizes $LTD_4$-induced renal hemodynamic actions and blocks the binding of $LTD_4$ to mesangial cells which are responsible, in part, for regulating hemodynamics in the kidney. (Badr. K. F. et al. (1989) Proc. Natl. Acad. Sci. USA 86:438.)

The compounds of this invention may be administered to antagonize the action of sulfidopeptide leukotrienes, such as $LTD_4$, $LTC_4$, and $LTB_4$. Leukotriene-mediated vasoconstrictive responses are associated with diseases such as: asthma, anaphylactic reactions, allergic reactions, shock, inflammation, rheumatoid arthritis, gout, psoriasis, allergic rhinitis, adult respiratory distress syndrome, Crohn's disease, endotoxin shock, traumatic shock, hemmorrhagic shock, bowl ischemic shock, renal glomerular disease, benign prostatic hypertrophy, inflammatory bowl disease, myocardial ischemia, myocardial infarction, circulatory shock, brain injury, systemic lupus erythematosus, chronic renal disease, cardiovascular disease, and hypertension.

In another embodiment, the compounds of this invention are used to treat or prevent a vasocontractive response or condition. LXs induce endothelium-dependent vasodilation ($LXA_4$) (Lefer, A. M. et al (1988) Proc. Natl. Acad. Sci. USA 85:8340) and dilation of cerebral arterioles in new born pigs in vivo ($LXA_4$ and $LXB_4$) (Busija, D. W. et al. (1989) Am. J. Physiol. 256:468.). Furthermore, $LXA_4$ induces rapid arteriolar dilation in hamster cheek pouch in vivo (Dahlen, S.-E. et al. (1987) Acta Physiol. Scand. 130:643) and in the renal hemodynamics of the rat. (Badr, K. F. et al. (1987) Biochem. Biophys. Res. Commun. 145: 408).

Vasocontractive responses or conditions cause, contribute, or are associated with diseases and conditions such as renal hemodynamic diseases, including glomerular diseases, cardiovascular diseases including hypertension, myocardial infarction, myocardial ischemia, and vascular diseases and gastrointestinal diseases.

Also encompassed by this invention is a method of screening LX analogs or other compounds to identify those having a longer tissue half-life than the corresponding natural LX. This method can be used to determine whether the compound inhibits, resists, or more slowly undergoes metabolism compared to the natural LX. This method is performed by preparing at least one enzyme which metabolizes LXs, contacting the compound with the enzyme preparation, and determining whether the compound inhibits, resists, or more slowly undergoes metabolism by the enzyme. Cells having a LX recognition site, such as polymorphonuclear neutrophils, peripheral blood monocytes, and differentiated HL-60 cells are among the appropriate sources for the enzyme preparation. The LX recognition site may exist naturally, or be induced artificially, by a disease state, or by an injury. A non-limiting example of artificially-induced $LXA_4$ recognition sites is the induction of such sites in differentiated HL-60 cells.

In one embodiment, preparation of the enzymes comprised harvesting cells and performing freeze-thaw lysis three times, followed by ultracentrifugation to yield a 100,000 g supernatant A cell-free 100,000 g pellet may also be used. In addition, an enzyme preparation may comprise any enzymes that do not participate in natural LX metabolism, but perform transformations upon LXs similar or equivalent to those transformations performed by the enzyme or enzymes which naturally metabolize LXs. Nonlimiting examples of appropriate enzymes are 15-hydroxyprostaglandin dehydrogenase, cytochrome P450 monogenases from human leukocytes, and rat and human liver microsomes.

Characterization of LX metabolites included standard techniques such as extraction, chromatography, and quantitative HPLC followed by trimethyl silyl derivatization, O-methoxime derivatization and gas chromatography/mass spectroscopy analysis. The experimental details of this embodiment are described below in Example 1.

LX analogs can also be screened for binding activity with a LX receptor recognition site, for example by contacting the compound with a receptor recognition site and determining whether and to what degree the compound binds. Examples of kinetic binding assays include homologous displacement, competitive binding, isotherm, and equilibrium binding assays.

The receptor recognition site may normally exist or it may be induced by a disease state, by an injury, or by artificial means. For example, retinoic acid, PMA, or DMSO may be used to induce differentiation in HL-60 cells. Differentiated HL-60 cells express $LXA_4$-specific receptor recognition sites. Examples of other cells which may be screened for LX specificity include PMN, epithelial cells, and peripheral blood monocytes.

Selection of competitive ligands will depend upon the nature of the recognition site, the structure of the natural substrate, any structural or functional analogs of the natural substrate known in the art, and other factors considered by a skilled artisan in making such a determination. Such ligands also include known receptor antagonists. The compounds of this invention may be radiolabelled with isotopes including $^2H$, $^3H$, $^{13}C$, and $^{14}C$ by standard techniques known in the art of radiochemistry or synthetic chemistry.

In one embodiment of this method, the structural specificity of induced $LXA_4$ recognition sites was assessed with $LXB_4$, $LTC_4$, $LTB_4$ and trihydroxyheptanoic methyl ester. The experimental details of this embodiment are described below in Example 2.

In addition, the compounds of this invention may be used to exert certain actions on specific cell types as developmental models for inflammation and injury. For example, $LXA_4$ stimulates the mobilization of intra-cellular $Ca^{2+}$, lipid remodeling, and chemotaxis without aggregation in human PMN (Palmblad, J. et al. Biochem. Biophys Res. Commun. (1987) 145: 168; Lee, T. H. et al. Clin. Sci. (1989) 77:195; Nigam, S. et al. J. Cell. Physiol. (1990) 143:512; Luscinskas, F. W. et al. (1990) Biochem. Pharmacol. 39:355). $LXA_4$ also blocks both $LTB_4$ and FMLP-induced responses, such as $IP_3$ generation. $LXB_4$ also stimulates lipid remodeling. $LXA_4$ activates isolated PKC, and is specific for the γ-subspecies of PKC which is found in the brain and spinal cord. (Hansson, A. et al. Biochem. Biophys. Res. Commun. (1986) 134: 1215; Shearman, M. S. et al. FEBS Lett. (1989) 245: 167); The publication Nicolaou, K. C. et al. Angew. Chem. Int. Ed. Engl. (1991) 30: 1100 and references cited within are expressly incorporated here by reference.

The present invention is further illustrated by the following examples which should in no way be construed as being further limiting. The contents of all references and issued patents cited throughout all portions of this application including the background are expressly incorporated by reference.

EXAMPLES

Example 1

Synthesis of Lipoxin Analog Compounds

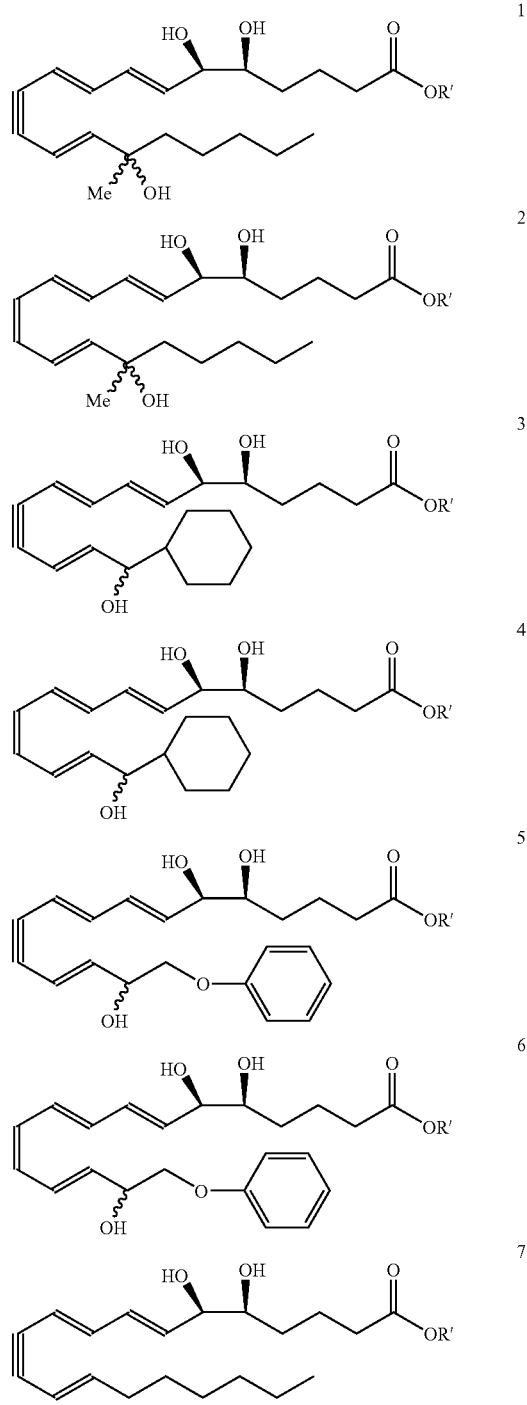

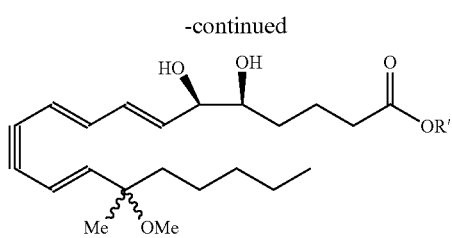

Preparation of the Methyl Ester Precursor of Compound 1:

To a solution of 3-methyl-3-trimethylsiloxy-1-bromo-1-octene (130 mg. 0.44 mmol) in benzene (15 mL) was added n-propylamine (0.05 mL, 0.61 mmol) and Pd(PPh$_3$)$_4$ (20 mg. 0.02 mmol) and the solution was protected from light. It was then degassed by the freeze-thaw method and stirred at rt for 45 min. (7E, 9E, 5S, 6R) Methyl 5,6-di(tert-butyldimethylsiloxy)-dodeca-7,9-diene-11-ynoate (183 mg. 0.44 mmol) (compound 12) and copper iodide (14 mg. 0.07 mmol) were added and the solution was one more time degassed by the freeze-thaw method. The mixture was stirred for 3 h at rt and quenched with saturated aqueous solution of NH$_4$Cl and extracted with ether. It was then washed with brine and dried over MgSO$_4$ and the solvent was evaporated. Flash column chromatography (silica, 3% ether hexanes) afforded pure compound as a colorless liquid (171 mg. 57% yield).

To a solution of the compound (171 mg. 0.25 mmol) in THF (0.5 mL) was added n-BuN$_4$F (0.9 mL. 0.90 mmol) and the mixture was stirred at rt. The reaction was completed in 2 h at which time it was poured into water and extracted with ether. The ether extracts were washed with brine, dried over Na$_2$SO$_4$ and the solvent was evaporated. Flash column chromatography (silica 4% MeOH/CH$_2$Cl$_2$) afforded the methyl ester (24 mg.) together with some of the corresponding lactone. HPLC retention time: 9:39 min (microsorb reverse phase, 4-6 mm×25 cm, C-18 column, MeOH/H$_2$O 70:30 flow rate 1 ml/min, UV detector at 300 nm). UV in MeOH: $\lambda_{max}$ 283, 294, 311 nm. $^1$H NMR (500 MHz CDCl$_3$) δ6.53 (dd. 15-210.9 Hz, 1 H), 6.32 (dd, J=15.1, 11.01 Hz, 1 H), 6.17 (d, J=15.9 Hz, 1 H) 5.83 (dd. J=17.5, 2.1 Hz, 1 H), 5.80 (dd. J=15.2, 6.7 Hz, 1 H), 5.72 (dd. J=17.0, 2.1 Hz, 1 H), 4.14 (m, 1 H), 3.68-3.64 (m, 4H), 2.35-2.31 (m, 2 H), 1.51-1.48 (m, 1 H), 1.43-1.42 (m, 2 H), 1.30-1.23 (m, 15 H) 0.85 (t, 3 H). $^{13}$C NMR (126 MHz, CDCl$_3$) δ150.01, 140.18, 132.95, 132.26, 112.43, 107.50, 75.23, 73.76, 42.49, 33.67, 32.17, 31.36, 27.96, 23.56, 22.58, 21.03, 14.03.

Preparation of the Methyl Ester Precursor of Compound 2:

A solution of the methyl ester precursor of compound 1 (3 mg. in CH$_2$Cl$_2$ (1 ml) was mixed with Lindlar's catalyst (1 mg.) and placed under a hydrogen atmosphere. The mixture was stirred at rt in the dark followed by HPLC until about 80% conversion (1 h). Filtration over celite evaporation of the solvent and separation by HPLC gave a pure methyl ester. HPLC retention time: 10:02 min (microsorb reverse phase. 10 mm X 25 cm C-18 column, MeOH/H$_2$O 70:30 flow rate 4 ml/min. UV detector at 300 nm). UV in MeOH: $\eta_{max}$ 287, 301, 315 nm.

Preparation of the Methyl Ester Precursor of Compound 3:

This compound was prepared similarly to the preparation of the methyl ester precursor of compound 1 (from 3-cyclohexyl-3-trimethylsiloxy-1-bromo-1-octene). Desilylation of this compound was also performed in a similar manner to afford the methyl ester. HPLC retention time 8:02 min (microsorb reverse phase, 4.6 mm×25 cm. C-18 column, MeOH/H$_2$O 70:30, flow rate 1 ml/min, UV detector at 300 nm). UV in MeOH: $\lambda_{max}$ 282, 293, 311 nm. $^1$H NMR (360 MHz, CDCl$_3$) δ6.56 (dd, 154, 10.9 Hz, 1 H), 6.33 (dd, J=15.2, 10.9 Hz, 1 H), 6.13 (dd, J=15.8, 6.5 Hz, 1 H), 5.81 (dd, J=15.2, 6.4 Hz, 1 H), 5.80 (d, J=15.6 Hz, 1 H), 5.73 (dd, J=15.4, 2.1 Hz, 1 H), 4.15 (br, 1 H), 3.93-3.90 (m, 1 H), 3.67 (br, 1 H), 3.65 (s, 3 H), 2-34 (t, 2 H), 1.82-1.65 (m, 10 H), 1.46-1.38 (m, 3 H), 1.26-1.01 (m, 5 H).

Preparation of the Methyl Ester Precursor of Compound 4:

Selective hydrogenation of the methyl ester precursor of compound 3, followed by HPLC purification gave the methyl ester precursor of compound 4. HPLC retention time: 9.72 min (microsorb reverse phase, 10 mm×25 cm C-18 column, MeOH/H$_2$O 70:30 flow rate 4 ml/min UV detector at 300 nm), UV in MeOH: max 288, 301, 315 nm. $^1$H NMR (250 MHz, C$_6$D$_6$) δ 6.66-6.89 (m, 2 H), 5.95-6.24 (m, 4 H), 5.55-5.66 (m, 2 H), 3.82 (m, 1 H), 3.73 (m, 1 H), 3.41 (m, 1 H), 3.31 (s, 3 H, OCH$_3$), 2.08 (t, 2H, CH$_2$COO), 1.00-1.81 (m, 18 H).

The methylesters can be converted to corresponding alcohols using standard techniques.

Synthesis of 15(R)-15-methyl-LXA$_4$ and 15(±)methyl-LXA$_4$

Approximately 1 gm acetylenic ketone a is prepared using Friedel-Crafts acylation of bis(trimethylsilyl) acetylene with hexanoyl chloride and is reduced using (−)-pinayl-9-BBN to give the (S) alcohol in CH$_3$N$_2$ as in Webber, S. E. et al. (1988) Adv. Exp. Med. Biol. 229:61; Nicolaou, K. C. et al. (1991) Angew. Chem. Int. Ed. Engl. 30:1100; and Vorbrüggen, H. et al.: In: Chemistry, Biochemistry, and Pharmacological Activity of Prostanoids (Roberts, S. M., Scheinmann, F. eds.). Oxford: Pergamon Press, to generate the methyl at C-15.

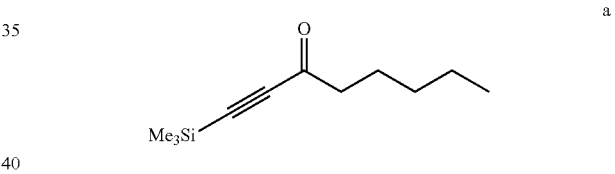

Alternatively, the keto group can be treated with CH$_3$MgBr (60⇒70° C.) as in Vorbrüggen, H. et al.: In: Chemistry, Biochemistry, and Pharmacological Activity of Prostanoids (Roberts, S. M., Scheinmann, F. eds.). Oxford: Pergamon Press to yield the 15(±)methyl of b (2-5 g) in dry CH$_2$Cl$_2$ (~20 ml) at 0° C. with sequential additions of 2,6-lutidine (5.2 ml) and tert-butyldimethylsilyl triflate (6.9 ml). This reaction is mixed for 1 h and then diluted with 100 ml ether for aqueous extraction and drying with MgSO$_4$.

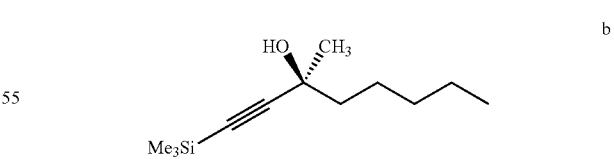

The product c is then coupled with d

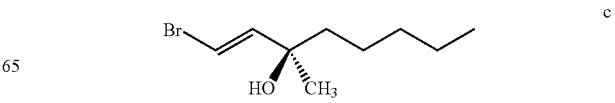

-continued

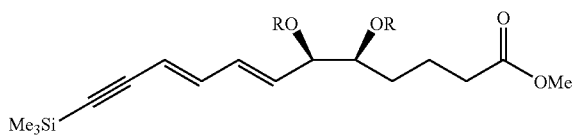
d that is generated as in Nicolaou, K. C. et al. (1991) Angew Chem. Int. Ed Engl. 30:1100; Nicolaou, K. C. et al. (1989) J. Org. Chem. 54:5527 and Webber, S. E. et al. (1988) Adv. Exp. Med. Biol. 229:61. Structure d from fragment A in Scheme I is suspended in 4.0 equiv. of $AgNO_3$, then 7.0 equiv. of KCN, containing $EtOH:THF:H_2O$ (1:1:1), 0-25° C. for 2 h to generate the C-methyl ester protected 15-methyl-$LXA_4$ analog that is concentrated and saponified in THF with LiOH (2 drops, 0.1 M) at 4° C. 12-24 h to give the corresponding free acid.

Synthesis of 16-dimethyl-$LXA_4$

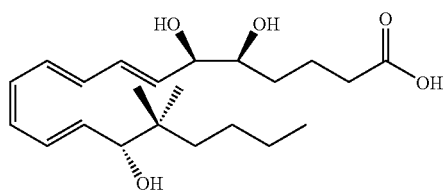

This compound is generated using the similar strategy by coupling d above with e vide supra, or f to generate the 15-phenyl-$LXA_4$ analog, or g to generate the 17-m-chlorophenoxy-$LXA_4$ analogs.

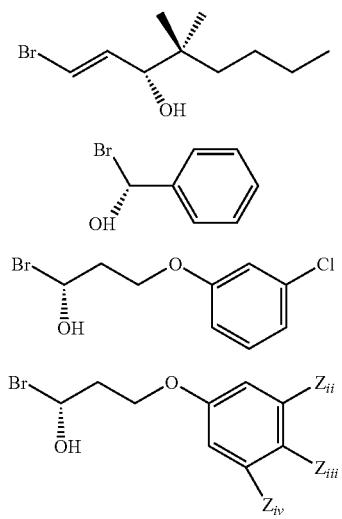

The appropriate C fragments in Scheme I (i.e. e, f, g, h) are each prepared as reviewed in Radüchel, B. and Vorbrüggen, H. (1985) Adv. Prostaglandin Thromboxane Leukotriene Res. 14:263 for the known corresponding prostaglandin analogues. In h, R=H; Cl, methoxy or halogen.

Synthesis of 13,14-acetylenic-$LXA_4$ and Halogen-Containing Analogs.

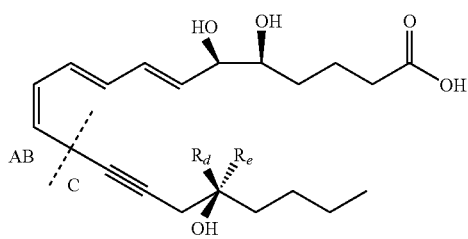

Using the $A_2B_2$ generated fragment from Scheme II, the corresponding $C_2$ fragments are prepared for coupling.

Structures j and k are generated as in Nicolaou, K. C. et al. (1989) J. Org. Chem. 54:5527 and methylated as in Radüchel, B. and Vorbrüggen, H. (1985) Adv. Prostaglandin Thromboxane Leukotriene Res. 14:263 are coupled to 7 to yield these LX analogues. The materials may be subject to RP-HPLC for purification vide supra.

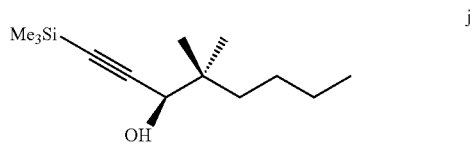
j

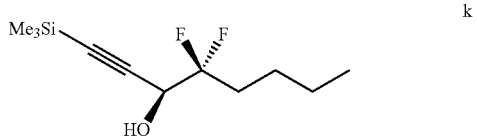
k

Synthesis of 14,15-acetylenic-$LXA_4$.

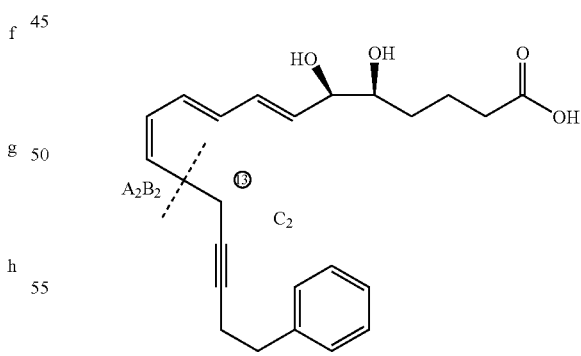

The designated combined $A_2B_2$ fragment can be prepared from couplings of fragments $A_1$ and $B_1$, illustrated in Route II to carry the structure of 7 or 4 vide supra for coupling to fragment $C_2$. The precursor for the $C_2$ fragment I can be prepared as in Radüchel, B. and Vorbrüggen, H. (1985) Adv. Prostaglandin Thromboxane Leukotriene Res. 14:263 for a prostaglandin analog.

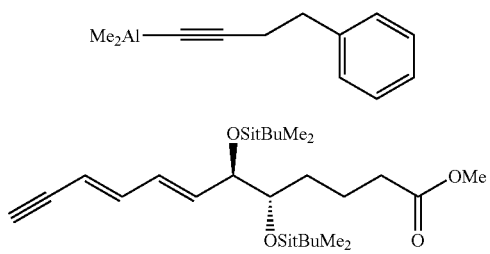

l m

Precursor m as prepared previously (Nicolaou, K. C. (1989) J. Org. Chem. 54:5527) is added at 1.2 equiv. to 0.05 equiv. of Pd(Ph$_3$)$_4$, 0.16 equiv. of CuI, n-PrNH$_2$, in benzene with Me$_2$Al-carrying 1, 2-3 h RT to yield n.

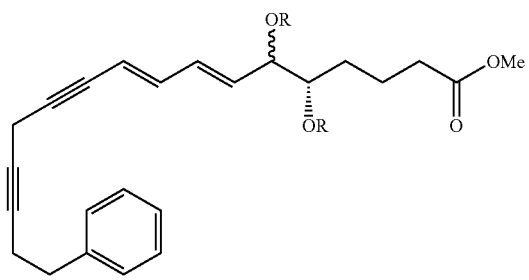

n

The alcohol protecting groups TBDMS=R are removed with 10 equiv. of HF-pyr, THF, 0-25° C. (4 h) followed by exposure to 3.0 equivalents of Et$_3$N, MeOH, 25° C. 15 min to open acid-induced δ-lactones that usually form between C-1 carboxy and C-5 alcohol in the LXs (Serhan, C. N. (1990) Meth. Enzymol. 187:167 and Nicolaou, K. C. (1989) J. Org. Chem. 54:5527). After mild treatment with Lindlar cat. 5% by weight, the extracted material may be subjected to LiOH saponification in THF to generate the free acid of the target molecule that can be subject to further purification by RP-HPLC gradient mobile phase as in (Serhan, C. N. et al. (1990) Meth Enzymol. 187:167).

Synthesis of 15(±)methyl-cyclo-LXA$_4$

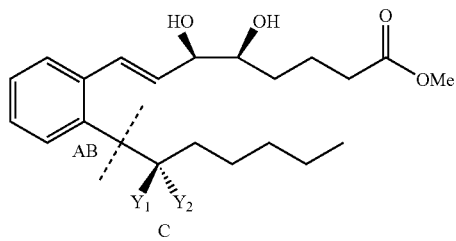

o

Compound o as the SiMe$_3$ derivative can be placed (~1 gm) in a round bottom 100 ml flask under an atmosphere enriched with argon in degassed benzene (20 ml). To this add 3.0 equivalents of a vinyl bromide fragment vide infra. This coupling reaction is carried out in catalytic amounts of Pd(PPh$_3$)$_4$ and CuI and can be monitored by injected aliquots of this suspension into RP-HPLC monitored by UV abundance with a rapid scanning diode. The progression line course 1-3 h at 23° C. after which the material is extracted with ethyl acetate: H$_2$O 4:1 v/v) and concentrated by rotoevaporation. The methyl ester can be saponified in LiOH/THF to give quantitative yields of the free carboxylic acid. Other derivatives can be prepared as above using fragment A with different fragment B moieties that have been substituted to give for example a dimethyl or other derivative. This can be obtained by taking the readily available ketone p and treating it with CH$_3$MgBr (60° C.) to generate q that can also be coupled to fragment A as above using conventional techniques such as Pd(O)—Cu(I) coupling. Increased chain length from C-15 can also be obtained.

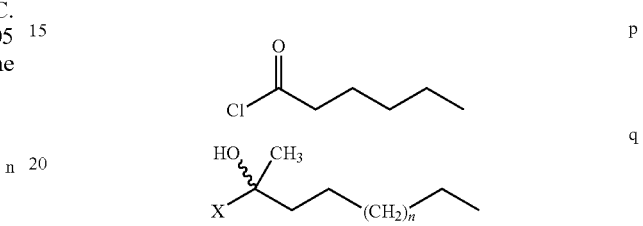

p q

Synthesis of 5-Methyl-LXB$_4$ and 4,4-Dimethyl-LXB$_4$.

The 5-methyl-LXB$_4$ hinders or retards 5-oxo-LXB$_4$ formation. Using the general scheme outlined above, the A fragment can be constructed to carry the 5-methyl in a vinyl bromide r precursor that is coupled to a joined B+C fragment by Pd(0)—Cu(I) coupling.

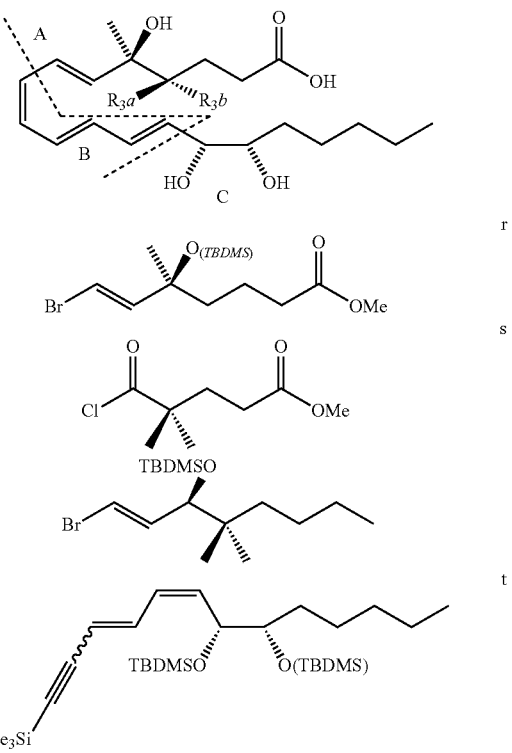

r s t

The vinyl bromide r can be obtained from the s that contains either dimethyl or hydrogen substituents at its CA position. The protected precursor t containing fragments B+C is generated as reported in reference (Nicolaou K. C. et al. (1991) Angew. Chem. Int. Ed. Engl. 30: 1100-16.). Compound t is converted to s or 28 by coupling with the indicated vinyl bromide. Thus the target molecule can be generated by adding r at 1.0 equv. (≈1 gm) to a round bottom flask degassed containing $Et_2NH$ as solvent with t injected in $Et_2NH$ at 1.2 equiv. $Pd(Ph_3P)_4$ is added at 0.02 equiv. to give the 8(9)-containing acetylenic precursor methyl ester of s.

The material is extracted and subject to rotoevaporation suspended in quinoline (0.5 eq) in $CH_2Cl_2$ and subject to hydrogenation using (10%; 25° C.) Lindlar catalyst and a steam of $H_2$ gas to selectively reduce the acetylenic double bond at position 8. The formation of the tetraene component of the methylester of 5-methyl-$LXB_4$ or 4 dimethyl-$LXB_4$ methyl ester can be monitored by RP-HPLC to assess completion of the reduction (i.e., 1-3 h). The methyl#esters are next saponified to their corresponding free acids by treating the products with LiOH in THF 25 μl $H_2O$ added at 0⇒24°, 8-24 h.

Example 2

Lipoxin $A_4$ Metabolism by Human Promyelocytic Leukemia Cells and Monocytes: Half-Life Assay HL-60 cells were purchased from American Type Culture Collection (Rockville, Md.), and other cell culture reagents were from GIBCO (Grand Island, N.Y.). Versene (EDTA) was from Whittaker Bioproducts (Walkersville, Md.). Synthetic 11,12-acetylenic $LXA_4$ methyl ester and LXs were from Cascade Biochemical (Reading, U.K.). 15(S)-15-m-$PGE_1$, $PGE_1$ and 5-HETE were from Cayman Chemical Co. (Ann Arbor, Mich.). [11,12-$^3$H]$LXA_4$ was prepared from 11,12-acetylenic $LXA_4$ using Lindlar catalyst as a custom tritiation (NET-259, lot 0 2793-275, New England Nuclear, Boston, Mass.). Tritiated products were isolated using RP-HPLC (Fiore et al. (1992) J. Biol. Chem. 267:16168; Serhan, C. N. (1990) Meth. Enzymol. 187:167). Methoxyamine and NAD were from Sigma Chemical Company (St Louis, Mo.). Manganese dioxide and Adams reagent were from Aldrich Chemical Co. (Milwaukee, Wis.).

Human PMN were obtained from healthy volunteers by gradient centrifugation of heparinized fresh venous blood (Böyum, A. (1986) Scand. J. Clin. Lab. Invest 21:77). HL-60 cells were seeded in RPMI supplemented with penicillin (100 U/ml), streptomycin (100 μ/ml), fetal bovine serum (10%) (Hyclone, Logan, Utah) and incubated (37-C with 5% $CO_2$ atmosphere) in plastic 250 ml flasks. Individual flasks containing $5\times10^{-7}$ HL40 cells/ml were incubated in the presence or absence of phorbol 12-myristate 13-acetate (PMA) (10 or 16 nM, 24-27 h) and adherence was monitored for induction of macrophage-like phenotype as in Collins, S. J. (1987) Blood 70:1233. Peripheral blood monocytes were obtained (Goldyne, M. E. et al. (1984) J. Biol. Chem. 259:8815 after plating fresh mononuclear cells onto plastic petri dishes containing PBS with glucose (1 mg/ml) for 1 h at 37° C. Non-adherent cells were removed and adherent mononuclear cells; were gently resuspended using Versene (7 ml/plate) and washed in PBS. PMN (>98%), adherent monocytes (>95%) and HL60 cells were enumerated by light microscopy, suspending in PBS for incubations, and <2-3% in each case were permeable to trypan blue. For some experiments, cell-free supernatants were prepared from HL-60 cells treated with PMA (16 nM) for 24-72 h. After harvesting, the differentiated cells were washed, then subject to freeze-thaw lysis (repeated 3 times) and ultracentrifugation (100,000 g, 1 h).

Incubations with eicosanoids were stopped with cold methanol containing either $PGB_2$ or 5-HETE as internal standards (5-HE was used when 15-oxo-ETE was quantified). Products were extracted using Sep-pak C18 and routinely chromatographed as in Serhan, C. N. (1990) Meth. Enzymol. 187:167. RP HPLC system consisted of an LKB gradient dual pump equipped with an Altex Ultrasphere-ODS (4.6 mm×25 cm) column, flow rate 1 ml/min eluted (0-20 min) with methanol/$H_2O$/acetic acid (65:35:0.01) and methanol/acetic acid (99.99/0.1) in a linear gradient (20-45 min) that was used to quantitate the ω-metabolites of $LTB_4$ (i.e. 20-COOH and 20-OH-$LTB_4$) as well as $LXA_4$. Recovery of internal standards was 82.2 7.9, mean S.D. (n=13). Compounds I-IV were separated using an Altex Ultrasphere-ODS column (10 mm×25 cm) eluted at a flow rate of 3.0 ml/min with methanol/$H_2O$/acetic acid (60:40:0.01, v/v/v). Formation of 15-oxo-ETE by 100,000 g supernatants (cf. Agins, A. P. et al. (1987) Agents Actions 21:397; Xun, C-Q. et al. (1991) Biochem. J. 279:553; and Sok, D-E. et al. (1988) Biochem. Biophys. Res. Commun. 156:524) was quantified after RP-HPLC using an ODS column (4.6 mm×25 cm) eluted with methanol/$H_2O$/acetic acid (70:30:0.01, v/v/v) monitored at 280 nm with a flow rate of 1 ml/min. Monocyte-derived products were also chromatographed using a Hypersil column (5 IL, 4 mm×300 mm) eluted with methanol/$H_2O$/acetic acid (60.40:0.01, v/v/v) and a flow rate of 1 ml/min. On-line spectra were recorded using a diode array detector (Hewlett-Packard 1040M series II) equipped with $HPLC^{3D}$ ChemStation software (DOS series). Spectra were acquired using step 4 nm, $B_w$=10 nm, range=235-360 nm with a sampling interval of 1.28 sec.

GC/MS was performed with a Hewlett-Packard 5971A mass selective detector quadrupole equipped with a HPG1030A workstation and GC 5890. The column was a HPUltra 2 (cross-linked 5% phenyl methyl silicone gum phase; 25 m×0.2 mm×0.33 μm) and injections were made in the splitless mode in bis(TMS)trifluoroacetamide (BSTFA). The temperature program was initiated at 150° C. and reached 250° C. at 10 min and 325° at 20 min. Standard saturated fatty acid methyl esters $C_{16}$-$C_{26}$ gave the following retention times (min:sec; mean of n=6). $C_{16}$, 8.03; $C_{18}$, 9.77; $C_{20}$, 12.22; $C_{22}$, 16.11; $C_{24}$, 20.72; $C_{26}$, 23.62 that were used to calculate respective C values of LX-derived metabolites as in Serhan, C. N. (1990) Meth. Enzymol. 187:167. Diazomethane was prepared and the methyl ester products were treated with BSTFA (Pierce Chemical Co., Rockford, Ill.) to obtain $Me_3Si$ derivatives. Methyl ester O-methoxime derivatives were prepared as in Kelly, R. W. and Abel, M. H. (1983) Biomed. Mass Spectrom. 10:276. Catalytic hydrogenations were performed in methanol (1 ml) with Adams reagent (Aldrich, Milwaukee, Wis.) by saturating the platinum IV oxide (1-2 mg) with a stream of bubbling hydrogen (20 min, RT). After extraction, materials were treated with diazomethane followed by BSTFA (overnight; RT).

Results

Metabolism of $LXA_4$: Intact neutrophils from peripheral blood of healthy donors did not significantly metabolize exogenous $LXA_4$ while cells from the same donors rapidly transformed $LXA_4$ via ω-oxidation. In contrast, PMA-treated UL-60 cells that displayed monocyte/macrophage-like characteristics rapidly transformed $LXA_4$. Within the first 60 s of exposure, >70% of $LXA_4$ was metabolized. In the absence of PMA treatment, neither intact HL60 cells (undifferentiated) nor their cell-free supernatants (100,000×g) ft=orm $LXA_4$ (n=3).

Differentiated HL-60 cells incubated with $LXA_4$ converted this eicosanoid to several products. Labeled $LXA_4$ was transformed to four main products that carried tritium (denoted compounds I-IV), which were collected for further analysis.

Structures of compounds I-IV To obtain quantities of these compounds enabling structural studies, their retention times in RP-HPLC were established using the $^3$H-label elution profile to mark boundaries, and unlabeled samples pooled from several incubations were chromatographed and individually collected from within these regions for GC/MS analysis Selected ion monitoring of the products obtained after treatment with diazomethane and BSTFA revealed that compounds I-IV each displayed prominent ions at m/z 203 [—CH(OSiMe$_3$)—(CH$_2$)$_3$—COOCH$_3$] indicating that carbons 1 through 5 of LXA$_4$ (carboxylic carbon is number 1) were not modified, although each product gave a different retention time than LXA$_4$. The methyl ester, trimethylsilyl derivative of LXA$_4$ displayed prominent ions in its electron impact spectrum at m/z 203 (base peak) and 173, with its molecular ion at 582 (M$^+$4). Other ions of diagnostic value in this derivative of LXA$_4$ are observed at m/z 171 (203-32), 409 (M-173), 379 (M-203), 482 (M-100) and 492 (M-90) (Serhan, C. N. et al. (1984) Proc. Natl. Acad. Sci. USA 81:5335; and Serhan, C. N. (1990) Meth. Enzymol 187:167. It is noteworthy that the LXs in general are known to give extremely weak molecular ion peaks (Serhan, C. N. et al. (1984) Proc. Natl. Acad. Sci. USA 81:5335). Nevertheless, compounds labeled I & II also possess prominent ions at m/z 173 (Me$_3$SiO$^+$=CH—(CH$_2$)$_4$—CH$_3$) indicating that the carbon 15-20 fragment of these LXA$_4$-derived products was intact, while the ion at m/z 173 was not evident in compounds III and IV. Thus, the conclusion that compounds I-IV are metabolites of LXA$_4$ was based upon: their physical properties (HPLC and GC/MS), the finding that they carry tritium label, as well as the absence of these products in incubations with HL60 cells not treated with PMA.

Next, compounds III and IV were focused on since it appeared that they represent metabolites with structural modifications in the carbon 15 through 20 fragment of LXA$_4$. Since ω-oxidation (hydroxylation at carbon 20) was a possibility, ions that could result from the respective 20-OH and 20-COOH forms of LXA$_4$ after derivatization, namely m/z 261 and 217 (Me$_3$SiO$^+$=CH—(CH$_2$)$_4$—CH$_2$OSiMe$_3$ and Me$_3$SiO$^+$=CH—(CH$_2$)$_4$—CO$_2$Me), were scanned in the acquired GC-MS data profiles. Neither III nor IV displayed prominent ions at either m/z 261 or 217 indicating that these products were not likely the result of ω-oxidation.]

The mass spectrum (C value 24.3) of the Me$_3$Si derivative, methyl ester of compound III was obtained. Prominent ions in its spectrum were observed at m/z 203 (base peak, CH(OSiMe$_3$)—(CH$_2$)$_3$—COOCH$_3$), 171 (203-32; elimination of CH$_3$0H), 215 [(M-203)-90, elimination of trimethylsilanol (Me$_3$SiOH)] and 99 (O=C—(CH$_2$)$_4$—CH$_3$). Ions of lower intensity were a m/z 508 (M$^+$) and 418 (M-90; loss of Me$_3$SiOH). The presence of these ions suggested that the material that coeluted with $^3$H-labeled compound III was the 15-oxo-derivative of LXA$_4$. This is supported by several lines of evidence, namely the virtual loss of the prominent ion at m/z 173 (Me$_3$SiO$^+$=CH—(CH$_2$)$_4$—CH$_3$), presence of m/z 99 (O=C—(CH$_2$)$_4$—CH$_3$), the absence of a tetraene chromophore and appearance of a new chromophore at UV $\lambda_{max}$ at 335-340 nm. The tetraenone chromophore was confirmed by treating LXA$_4$ with MnO$_2$ in chloroform as used for prostaglandin conversion (Ānggard, E. and Samuelsson, B. (1964) J. Biol. Chem. 239:4097). Also, the mass spectrum of the catalytic hydrogenation product gave a C value of 25.1 with prominent ions at m/z 203 (base peak), m/z 99 (66%), m/z 313 (M-203 or M-CH(OSiMe$_3$)—(CH$_2$)$_3$—COOCH$_3$; 35%) and m/z 171 (36%) with no prominent ion at m/z 173. Less intense ions were at m/z 516 (M$^+$) and m/z 426 M-90). Thus, the upward shift of 8 amu and fragmentation of this saturated derivative were consistent with the generation of the corresponding 15-oxo-derivative.

To examine this LXA$_4$-derived product further, an aliquot of the material eluting beneath the peak labeled III was treated with diazomethane followed by methoximation (as in Bergholte, J. M. et al. (1987) Arch. Biochem. Biophys. 257:444) and treatment with BSTFA. Its spectrum, C value 25.4, showed prominent ions at m/z 203 (base peak), 171 (203-32; loss of CH$_3$OH) and 229 [M-128 or CH$_3$O—N=C—(CH$_2$)$_4$ CH$_3$-(2×90)]. Ions of lower intensity were at m/z 537 (M$^+$), 466 (M-71, the at cleavage ion M-CH$_2$(CH$_2$)$_3$CH$_3$), 481 (M-56 or M-CH$_2$=CH—CH$_2$—CH$_3$, a McLafferty rearrangement ion), 431 [M-106 (possibly loss of C$_7$H$_5$N$^+$)], 401 [M-136 (elimination of Me$_3$SiOH+CH$_3$+—OCH$_3$) and 460 (M-77, loss of NOCH$_3$ plus MeOH). Again, an ion at m/z 173 that would have originated from an alcohol-containing C-15 fragment (Me$_3$SiO$^+$—CH—(CH$_2$)$_4$—CH$_3$) was virtually absent in its spectrum. Thus, the ions present are consistent with the methyl ester, O-methoxime derivative generated from the 15-oxo-containing derivative of LXA$_4$. Together the prominent ions observed with these different derivatives suggest that material eluting beneath the peak labeled III was the 15-oxo-product of LXA$_4$ (i.e. 15-oxo-LXA$_4$).

The mass spectrum of the methyl ester Me$_3$Si derivative (C value 26.0) of compound IV showed. prominent ions at m/z 203 (base peak, CH(OSiMe$_3$)—(CH$_2$)$_3$COOCH$_3$), 171 (203-32; loss of CH$_{30}$M), 99 (O=C—(CH$_2$)$_4$—CH$_3$) and 307 (M-203 or MCH(OSiMe$_3$)—(CH$_2$)$_3$—COOCH$_3$). Ions of lower intensity were at m/z 510 (M$^+$), 420 (M-90, loss of trimethylsilanol) and 208 (M-99+203)). Its UV spectrum showed a triplet of absorbance with maxima at 259, 269 and 280 nm, consistent for a conjugated triene chromophore. The presence of these ions and UV spectrum suggest that IV was a dihydro-15-oxo-metabolite of LXA$_4$. This basic structure was supported by the presence of the ion at m/z 99 that is consistent with a keto group at position carbon 15, and the presence of m/z 203 as base peak revealed that the alcohol groups at carbons 5 and 6 remain intact. In addition, the absence of a trienone chromophore ($\lambda$cal=310 nm) indicates that loss of a double bond was at Δ13-14 position to give the observed triene chromophore. Together these results indicate that compound IV was 13,14-dihydro-15-oxo-LXA$_4$.

The methyl ester, Me$_3$SiO derivative of compound II (C value –25.4) gave ions at m/z 203 (base peak; CH(OSiMe$_3$)—(CH$_2$)$_3$COOCH$_3$), 173 (Me$_3$SiO+=CH—(CH$_2$)$_4$—CH$_3$), 171 (203-32) and 584 (M$^+$). Its molecular ion was two mass units higher than the LXA$_4$ derivative. These ions and a triplet band of absorbance $\lambda_{max}$ MeOH 259 nm, 269 and 282 nm suggest that compound II was a dihydroderivative of LXA$_4$. The methyl ester, Me$_3$SiO derivative of compound I from HL-60 cells gave two products in GC. The major one (C value=25.0) gave similar ions in its mass spectrum as LXA$_4$, but instead its molecular ion was at m/z 586 with ions also present at m/z 555 (M-31) and 496 (M-90), indicating that two of the four double bonds were reduced (not shown). However, identical products were not observed with peripheral blood monocytes (vide infra), and thus the HL-60 cell-derived materials from peak I were not further characterized in the present experiments. The structures of 1-1V indicate that LXA$_4$ is not metabolized by ω-oxidation by intact leukocytes but instead is both dehydrogenated at carbon alcohol and also transformed from a conjugated tetraene to triene structures Taken together these observations suggested that LXA$_4$ may be attacked by NAD-dependent 15-prostaglandin dehydrogenase (5-PGDH), an enzyme known to carry out similar reactions with prostanoids as substrate (Ānggard, E.

and Samuelsson, B. (1964) J. Biol. Chem. 239:4097, and reviewed in Hansen, H. S. (1976) Prostaglandins 12:647).

15-PGDH activity was recently shown to be induced in HL-60 cells (Xun, C-Q. et al. (1991) Biochem. J. 279:553), and it apparently utilizes 15-HETE as substrate with 92% efficiency compared to $PGE_2$ (Agins, A. P. et al. (1987) Agents Actions 21:397). Indeed, 100,000 g supernatants prepared from PMA-treated HL-60 cells converted 15-HETE to 15-oxo-ETE indicating the presence of a dehydrogenase activity after differentiation. $LXA_4$ competed for catalysis of 15-HETE giving a $K_i=8.2\pm2.6$ µM (S.E.M., n=6) calculated from Lineweaver-Burke plots. At equimolar concentrations of $LXA_4$ and 15-HETE, $LXA_4$ blocked 15-oxo-ETE formation by ≈50%. The relative conversion for LX compared to $PGE_1$ by 100,000 g supernatants indicated that $LXA_4$, 11-trans-$LXA_4$ as well as $LXB_4$ but not 15-methyl-$PGE_1$ were converted Together, these results suggest that $LXA_4$>11-trans-$LXA_4$>$LXB_4$ are substrates for 15-PGDH or an equivalent enzyme system.

Since PMA induces differentiation to monocyte-macrophage-like lineage of HL60 cells (Collins, S. J. (1987) Blood 70:1233), peripheral blood monocytes were incubated to determine if they metabolize LX. LXss display potent actions with monocytes (Stenke, L. et al. (1991b) Biochem. Biophys. Res. Commun. 180:255) and these cells do not ω-oxidize eicosanoids (Goldyne, M. E. et al. (1984) J. Biol. Chem. 259:8815). When suspensions of both intact monocytes (n=5) and permeabilized cells (freeze-thaw or saponin-treated, n=5) were exposed to $LXA_4$, it was converted to 15-oxo-$LXA_4$ and conjugated triene-containing products, 13,14-dihydro-$LXA_4$ and 13,14-dihydro-15-Oxo-$LXA_4$. As with differentiated HL60 cells, monocytes rapidly converted $LXA_4$ (>60%) within 30 s. The temporal relationships for formation of these metabolites in both intact and permeabilized monocytes were similar and suggest that 15-oxo-$LXA_4$ metabolite is a transient intermediate. Also, in each monocyte suspension incubated with $^3H$-$LXA_4$ (d=33), 13,14-dihydro-15-oxo-$LXA_4$ and 13,14-dihydro-$LXA_4$ were major products carrying radiolabel. It is noteworthy that a product eluting before 13,14-dihydro-$LXA_4$ at 15.5-17 nm was observed that also displayed a triene chromophore and was likely the 11-trans isomer of 13,14-dihydro-$LXA_4$ that results from cis-trans isomerization encountered during work-up, The 11-cis double bond of native $LXA_4$ is labile and readily isomerizes to all-trans during extraction and isolation (Romano, M. and Serhan, C. N. (1992) Biochemistry 31:8269).

Example 3

Binding Affinity to Lipoxin Receptors Analogs

Human promyelocytic leukemia cells (HL60) were purchased from the American Type Culture Collection (Rockville, Md.). RPMI medium and cell culture reagents were from GIBCO (Grand Island, N.Y.). Synthetic $LXA_4$, trihydroxyheptanoic acid (methyl ester), $LXB_4$, $LTD_4$, $LTC_4$ and $LTB_4$ were from Biomol (Plymouth Meeting, Pa.), and SKF 104353 was from Smith Kline and French Laboratories. ONO 4057 was from ONO Pharmaceutical Co., Ltd. (Osaka, Japan). [14,15-$^3H$]$LTB_4$ (32.8 mCi/mmole), [1-$^{14}C$]arachidonic acid (50.2 mCi/mmole), $^{32}$PγATP (3,000 Ci/mmole), [9,10-$^3H$(N)]palmitic acid (30.0 mCi/mmole), and [9,10-$^3H$(N)]myristic acid (30.7 Ci/mmole) were purchased from New England Nuclear (DuPont Co., Boston, Mass.). 11,12-acetylenic $LXA_4$ was from Cascade Biochemicals (Oxford, UK). Microcentrifuge tube filters (0.45 µm cellulose acetate) were purchased from PGC Scientific (Gaithersburg, Md.) and silicon oils were from Harwick Chemical Corp. (Akron, Ohio) (d=1.05) and Thomas Scientific (Swedesboro, N.J.) (d=0.963), respectively. Nitroblue tetrazolium, PMA, DMSO, proteases, retinoic acid and Actinomycin D were purchased from Sigma (St. Louis, Mo.) Islet activating protein (IAP) was from LIST Biological Lab., Inc. (Campbell, Calif.). Plasticware, Whatman LK6D TLC plates and solvent (HPLC grade) were from Fisher (Springfield, N.J.).

Preparation of [11,12-$^3H$]$LXA_4$. Tritiation of 11,12-acetylenic $LXA_4$ methyl ester was carried out under a custom tritiation service (NET-259:92-2326) by New England Nuclear (Boston, Mass.). Briefly, 11,12-acetylene methyl ester was characterized by UV absorbance and reverse-phase HPLC as in (Nicolaou, K. C. et al. (1985) J. Am. Chem. Soc. 107:7515) and exposed to tritium atmosphere in methylene chloride at room temperature. This incubation was stirred in the presence of Lindlar catalyst (1.0 mg from Fluka Chemicals) for ~1 h. The resulting mixture was stored in methanol and isolated using RP-HPLC. Tritiated products were chromatographed as methyl esters utilizing a gradient HPLC system equipped with a photodiode array rapid spectral detector (Serhan, C. N., Methods in Enzymology: Arachidonate Related Lipid Mediators, in Murphy R. C., Fitzpatrick, F. (eds.), vol. 187. Orlando, Fla., Academic, (1990), p. 167). This mixture contained both [11,12-$^3H$]$LXA_4$ and [11,12-$^3H$]-11-trans-$LXA_4$ methyl esters (~1:3 ratio) as determined by coelution with synthetic standards. After RP-HPLC, fractions containing [11,12-$^3H$]$LXA_4$ were collected, and extracted into ethyl acetate. The free acid was prepared by LiOH saponification (Fiore, S. et al. (1992) J. Biol. Chem. 267:16168). Material from these fractions, when injected into UV-electrochemical detection HPLC, gave greater than 90% of radioactivity associated with a tetraene-containing product that coeluted with synthetic $LXA_4$. Materials that eluted with the retention time of authentic $LXA_4$ in two HPLC systems were taken for binding experiments. The specific activity calculated for [11,12-$^3H$]$LXA_4$ was 40.5 Ci/mmole.

Cell cultures and differentiation. HL60 cells were seeded in RPMI medium supplemented with 100 U/ml penicillin, 100 µg/ml streptomycin, and 10% fetal calf serum (Hyclone, Logan, Utah), incubated at 37° C. with 5% $CO_2$ atmosphere in 250 ml flasks. Individual flasks containing ~50×10$^6$ cells/ml next received dimethyl sulfoxide (DMSO) (1.12% v/v, 120 h) or retinoic acid (RA) (1 µM, 120 h) or phorbol myristate acetate (PMA) (20 nM, 48 h). Before performing binding assays, cells were washed twice in phosphate buffered saline (PBS), $Ca^{2+}$- and $Mg^{2+}$-free, enumerated and suspended at 20×10$^6$ cells/ml in Tris buffer (10 mM), pH 7.4 (Fiore, S. et al. (1992) J. Biol. Chem. 267:16168). Nitro blue tetrazolium reduction was performed to monitor induction of polymorphonuclear phenotype as in (Imaizumi, M. and Breitman, T. R. (1986) Blood 67:1273), and cell adherence was determined for induction of macrophage-like phenotype (Collins, S. J. (1987) Blood 70:1273). Human umbilical vein endothelial cells (HUVEC) maintained in culture third passage were obtained from Dr. M. Gimbrone (Brigham and Women's Hospital Department of Pathology).

PMN, platelet and RBC isolation from peripheral blood. Human PMN were obtained by the modified Böyum method (Böyum, A. (1968) Scan. J. Clin. Lab. Invest. 21:77) from fresh heparinized blood after venipuncture of healthy normal volunteers. Suspensions in PBS were monitored for cell number and viability by their ability to exclude trypan blue both exceeding 98% Red blood cells were obtained from 10 ml of heparinized blood after three centrifugations in PBS (2,500 rpm, 10 min at 21° C.). Blood drawn in acidic citrate dextrose (9:1, v/v) was used to isolate platelets as previously described (Serhan, C. N. and Sheppard, K.-A. (1990) J. Clin. Invest 85:772).

Ligand binding. $^3$H-LXA$_4$ and $^3$H-LTB$_4$ binding was performed essentially as in Fiore, S. et al. (1992) J. Biol. Chem. 267:16168. After suspending cells in Tris buffer 10 mM (pH 7.4, Ca$^{2+}$ 2.5 mM, Mg$^{2+}$ 1.2 mM), aliquots (0.5 ml) were incubated (20 min at 4° C.) with $^3$H-ligands alone (0.3 nM) or in the presence of increasing concentrations of homoligands or other compounds (3-300 nM). The incubations were rapidly centrifuged (60 sec, 12,000 g) on silicon oil (d=1.028), and cell-associated radioactivity was determined by liquid scintillation counting (Wallac 1409, Pharmacia, Piscataway, N.J.). Binding experiments with HUVEC cells were performed in 12 well plates with $3.5 \times 10^5$ cells/well. After 10 min, wells were washed twice with PBS and cell-associated label was recovered by adding glacial acetic acid (0.5 ml). Results obtained from these assays were submitted for further analysis using the Ligand program (Elsevier-Biosoft, Cambridge, UK).

PLD activity. Human PMN and HL-60 cells ($50 \times 10^6$ cells/ml) prepared as above were incubated with $^3$H-myristic acid or $^3$H-palmitic acid (8 µCi/$50 \times 106$ cells) for 40-60 min at 37° C. in PBS. Cell uptake ranged between 60-80% of added label, 7.1±4.2% (n=10; mean ±S.D.) and 32.6±10.3% (n=6; mean ±S.D.) into total phospholipid classes of PMN and HL-60 cells, respectively. Incubations were carried out at 37° C. ($10 \times 10^6$ cells/ml PBS). Agonists were added in 50 µL PBS or with 1:10 (v/v) EtOH:PBS for phosphatidylethanol (PEt) formation as in Billah, M. M. et al. (1989) J. Biol. Chem. 264:17069. At indicated times, incubations were stopped by adding 3.5 ml of ice cold CHCl$_3$/MeOH (2/5, v/v) containing 1-$^{14}$C-arachidonic acid (5,000 cpm) used here as internal standard to quantitate extraction recoveries. Samples were extracted using a modified Bligh and Dyer extraction as in (Serhan, C. N. and Sheppard, K.-A. (1990) J. Clin. Invest. 85:772). Organic phases, concentrated in 50 µL of CHCl$_3$:MeOH (8/2, v/v), were spotted onto linear K6D TLC plates developed with the organic phase of ethyl acetate/isooctane/acetic acid/water (110/50/20/100, v/v/v/v) for 50 min (Billah, M. M. et al. (1989) J. Biol. Chem. 264:17069). In this system, phosphatidic acid (PA) gave an $R_f$=0.1±0.04 and PEt gave an $R_f$=0.56±0.04; n=38±S.D. that were clearly separated from other phospholipids (that remained at the origin) or neutral lipids ($R_f$=0.75-0.90). Lipids were visualized with iodine vapor and identified by co-elution with authentic standards that were also spotted and chromatographed in each TLC plate. Regions corresponding to PA, PEt, and internal standards were scraped and quantified by liquid scintillation counting. In addition to $^3$H-myristate or $^3$H-palmitate labeling, both [1-$^{14}$C]arachidonate (0.25 µCi/$30 \times 10^6$ PMN) and $^{32}$PγATP (20 µCi/$50 \times 10^6$ PMN) labeled cells were used to monitor LXA$_4$-stimulated formation of PA and PEt generation. In these experiments, PA was resolved using ethyl acetate/isooctane/acetic acid (45/15/10, v/v/v) as solvent system (Bocckino, S. B. et al. (1989) Anal. Biochem. 180:24) and gave an $R_f$=0.46±0.03 (n=15). All values reported for PEt formation in Tables 4 and 5 were calculated by subtracting the dpm obtained in the presence of agonist(s) alone minus those measured in the presence of agonist(s) and 0.5% EtOH.

Impact of IAP and staurosporine on LXA$_4$-induced PLD activity. PLD activity assays, performed as described (vide supra), were preceded by cell exposure to either IAP or staurosporine. IAP treatment of PMN was performed as previously described (Nigam, S. et al. (1990) J. Cell Physiol. 143:512), and HL-60 cells were incubated in the presence or absence of IAP (300 ng/ml) for 2 h at 37° C. (Kanaho, Y. et al. (1992) J. Biol. Chem. 267:23554). Aliquots ($10^7$ cells/0.5 ml) were added to 0.4 ml buffer. Next, incubated cells were exposed to either 100 µl of vehicle (PBS, EtOH 0.04%) or LXA$_4$ ($10^{-7}$ M and $10^{-9}$ M), in the presence or absence of 0.5% EtOH. Staurosporine (100 nM) was added to cell suspensions for 5 min at 37° C. before addition of LXA$_4$.

Results

After preparation of synthetic [11,12-$^3$H]LXA$_4$, its specific binding to promyelocytic cells (HL-60) was characterized and direct comparisons with specific binding of [14,15-$^3$H]LTB$_4$ were performed. When routine phenotypic markers were monitored, untreated HL-60 cells displayed a low level of specific binding for both $^3$H-LXA$_4$ and $^3$H-LTB$_4$ ligands. Differentiation induced by exposure to either DMSO (1.12%) or retinoic acid (1 µM) for 5 days was accompanied with a three to fivefold increase in specific binding for both radioligands. PMA-treated cells (20 nM, 48 h) displaying characteristics of macrophagic-like phenotype, i.e. NBT negative cells that adhere to plastic (see Imaizumi, M. and Breitman, T. R. (1986) Blood 67:1273; Collins, S. J. (1987) Blood 70:1233), also led to the appearance of specific binding with both $^3$H-LXA$_4$ and $^3$H-LTB$_4$. Equilibrium binding with $^3$H-LXA$_4$ at 4° C. was reached at 10 min that remained virtually unchanged for the next 20 min.

To assess whether induction of specific binding for both $^3$H-ligands required de novo synthesis, Actinomycin D (2 µg/ml) was added with PMA incubations. Actinomycin D blocked the PMA-induced increment in specific binding for both labeled eicosanoids, suggesting inhibition of de novo protein biosynthesis also blocked appearance of specific binding sites. The impact of protease and glycosidase treatments was assessed with both differentiated HL60 cells and human PMN for $^3$H-LXA$_4$ specific binding. Protease treatment reduced specific binding and provided additional evidence in support of a protein component of LXA$_4$ specific binding sites.

Results from isotherm binding assays (4° C., 10 min) with differentiated HL-60 cells and [11,12-$^3$H]LXA$_4$ (0.1-30 nM) showed that [11,12-$^3$H]LXA$_4$ specific binding sites gave a $K_d$=0.6±0.3 nM. A nonlinear portion of the Scatchard plot was observed for concentrations observed with LXA$_4$ specific binding with human PMN (Fiore, S. et al. (1992) J. Biol. Chem. 267:16168). Results obtained here with LTB$_4$ specific binding with HL-60 cells, $K_d$=0.12 nM, are essentially in agreement with values recently reported by Harada (Xie, M. et al. (1991) J. Clin. Invest. 88:45), namely $K_d$=0.23 nM.

To further characterize the interactions of $^3$H-LXA$_4$ with its specific binding sites, competition binding experiments were performed with differentiated HL60 cells. LXA$_4$, LXB$_4$, LTB$_4$, LTC$_4$ and the leukotriene receptor antagonists SKF 104353 (LTD$_4$ antagonist; Harada, Y. (1990) Hiroshima J. Med. Sci. 39:89) and ONO-4057 (LTB$_4$ antagonist; Gleason, J. G. et al. (1987) J. Med. Chem. 30:959) were assessed as potential competing ligands. Neither LXB$_4$, LTB$_4$, nor trihydroxyheptanoic acid (methyl ester) (300 nM) were able to displace $^3$H-LXA$_4$ specific binding with differentiated HL60 cells while LTC$_4$ caused ~30% decrease of specific binding when added in 3 log molar excess. The finding that LXA$_4$ (300 nM) was unable to compete with $^3$H-LTB$_4$ (0.3 nM) binding to differentiated HL-60 cells suggests that LXA$_4$ and LTB$_4$ interact with separate classes of specific binding sites. Leukotriene receptor antagonists SKF 104353 and ONO-4057 did not displace $^3$H-LXA$_4$ binding with differentiated HL-60 cells, but SKF 104353 and LTD$_4$ were effective in competing the specific 3H-LXA$_4$ binding with HUVEC. HUVEC displayed a $K_d$ of 11.0±2.6 nM and a $B_{max}$ of 2.5×

$10^{-10}$ M for $^3$H-LXA$_4$, and virtually identical values were calculated for LTD$_4$ competition. In the case of $^3$H-LTB$_4$, HUVEC did not specifically bind LTB$_4$, but non-specific cell association was evident with this $^3$H-ligand (n=3; not shown). Specific association of $^3$H-LXA$_4$ was not evident among several other cell types surveyed. Here, neither washed platelets, RBCs, the β-cell (Raji), nor T-cell (Jurkat) cultured cell lines displayed specific binding for $^3$H-LXA$_4$. Taken together, these results indicate that LXA$_4$ interacts with unique binding sites in differentiated HL-60 cells that is not sensitive to either leukotriene receptor antagonist (SKF 104353 or ONO-4057). In HUVEC, $^3$H-LXA$_4$ specific binding was sensitive to both LTD$_4$ and SKF 104353 but not ONO-4057, suggesting that $^3$H-LXA$_4$ specific binding in this cell type may reflect its interaction with putative LTD$_4$ receptors.

LXA$_4$ rapidly stimulates phosphatidic acid formation in human neutrophils (Nigam, S. et al. (1990) J. Cell Physiol-143:512). To determine if $^3$H-LXA$_4$ binding confers PLD activation, PEt and PA were monitored in both PMN and HL-60 cells. Results indicated that LXA$_4$ stimulates PLD activity in these cell types with similar temporal responses. PMN exposed to LXA$_4$ ($10^{-10}$ M) rapidly generated the ethanol trapping product PEt within 60 s that declined to baseline levels by 5 min. In the absence of added EtOH, PEt was not formed at statistically significant levels. A biphasic concentration dependence was obtained for PEt formation in both PMN and differentiated HL60 cells. An apparent maximal response was noted with the concentration range of ~$10^{-9}$-$10^{-10}$ M LXA$_4$, and a second peak of activity was observed at $10^{-7}$ M LXA$_4$. Below $10^{-8}$ M, both the chemotactic peptide FMLP and LXA$_4$ gave results of similar magnitude with FMLP appearing to be slightly more potent with PMN from some donors. To evaluate the potential contribution of other biosynthetic pathways, LXA$_4$-induced PA formation was also examined in both $^{32}$PγATP and [1-$^{14}$C]-arachidonate-labeled PMN. $^{32}$P-labeled PA was evident in statistically significant levels only after 30 min of exposure to LXA$_4$ ($10^{-7}$ M). Similar results were obtained with $^{14}$C-labeled PA formation derived from $^{14}$C-arachidonate-labeled precursors. These findings indicated that LXA$_4$ can also stimulate other routes of PA formation in PMN but only after 30 min of exposure.

Only differentiated HL60 cells (expressing specific binding sites for $^3$H-LXA$_4$) incubated with LXA$_4$ rapidly generated PEt that was evident within 30 sec. Undifferentiated HL60 cells incubated with LXA$_4$ ($10^{-9}$ M) did not rapidly generate PEt. The concentration dependence with these cells also gave a biphasic response with LXA$_4$ and gave an apparent maximum at $10^{-9}$ M. To investigate possible signal transduction events involved in LXA$_4$-mediated PLD activation, PMN and HL60 cells were next exposed to either IAP or staurosporine. Results indicate that the LXA$_4$-mediated PLD activity evoked within the lower concentration range ($10^{-9}$-$10^{-10}$ M) was sensitive to IAP treatment in both cell types and, similarly, the PLD activity stimulated at higher concentrations of LXA$_4$ ($10^{-7}$ M) was inhibited by staurosporine. Thus, in both cellular systems at concentrations below $10^{-8}$ M, LXA$_4$ rapidly interacts with specific binding sites that trigger PLD activity and hence confers a functional response, while within submicromolar concentrations of LXA$_4$, it may stimulate additional processes that can also lead to activation of PLD.

Example 4

Lipoxin Bioactivity Assays

Several of the preferred LX analogs (shown structurally as compounds 1 through 8 above) were prepared by total synthesis as described in Example 1. Following preparation and isolation of these compounds via HPLC, compounds were first assessed to determine whether they retain biological activity using the neutrophil adhesion assay and epithelial cell transmigration assays (as described in Nash, S et al., (1987) J. Clin. Invest. 80:1104-1113; Nash, S et al., (1991) J. Clin. Invest 87: 1474-1477; Parkos, C. A. et al., (1991) J. Clin. Invest 88:1605-1612; Parkos, C. A. et al. (1992) J. Cell. Biol. 117:757-764; Madara J. L. et al., (1992) J. Tiss. Cult. Meth. 14:209-216).

Compounds 1 through 8 ($10^{-7}$-$10^{-10}$M) were found to inhibit neutrophil adhesion to endothelial cells and their transmigration on epithelial cells. The acetylenic precursors (compound 1, 3, 5 and 7) were found to be physically more stable than their tetraene counterparts. Compound 7, which did not have an alcohol group in the C15 position or other modifications in the series, showed no biological activity in the assays. It would therefore appear that a substituent in the C15 position of LX is necessary for the biological activity of at least LXA$_4$ analogs. 15-methyl-LX A4 (compound 2) also proved to inhibit polymorphonuclear (PMN) adhesion triggered by leukotriene B$_4$ (LTB$_4$) to human endothelial cells with an IC$_{50}$ of ~1 nM LX analogs 1 through 8 were found to block migration at potencies greater than or equal to synthetic LXA$_4$. Compound 7 was found to be essentially inactive within the concentration range for inhibition induced by LXA$_4$ or other analogs. The results in these neutrophil-containing bioassays indicate that LXA$_4$ analogs with modifications in C15-C20 positions retain their biological action and can inhibit PMN transmigration and adhesion events.

The "bio-half-life" of compounds 1-8 was assessed using phorbol ester-treated human promyelocytic leukemia (HL-60) cells as described in Example 2. These cells converted more than 95% of LX A$_4$ within five minutes of its addition to the cell incubation. LXA$_4$ in this system was rapidly transformed to 15-oxo-LXA$_4$. However, in the same assay, 15-methyl-LXA$_4$ (compound 2) and cyclohexyl-LXA$_4$ (compound 4) were quantitatively recovered in the incubation medium at times up to two hours. These results illustrate that modification in the carbon 20 through the carbon 15 positions prevents the further metabolism of LXA$_4$ by leukocytes.

In addition, the stability of the acetylenic methyl ester LXA$_4$ (compound 1) was recovered essentially intact after 60 minutes of incubation in whole blood (37° C.) ex vivo, as assessed after extraction and reverse phase HPLC. When taken together, these results indicate that LX analogs retain biological action and are resistant to further metabolism in vitro.

Example 5

Effect of 15-epi-Lipoxins' on Cell Proliferation

Materials and Methods

Synthetic (5S,6R,15R)-trihydroxy-7,9,13-trans-11-cis-eicosatetraenoate: carboxymethyl ester (15-epi-LXA$_4$-methyl ester) was prepared by total organic synthesis and was a gift of Prof. N. A. Petasis (Department of Chemistry, University of Southern California). 15-epi-LXA$_4$ free acid was obtained by saponification of 15-epi-LXA$_4$-methyl ester in tetrahydrofuran with LiOH (0.1 M) at 4° C. for 24 h. Synthetic eicosanoid reference samples were from Cascade Biochem Limited (Reading, Berkshire, England). Inhibitors of 5-LO (Rev 5901 isomer) and cytochrome P450 (17-octadecaynoic acid, 17-ODYA) activities were from Biomol (Plymouth Meeting, Pa.). Radiolabeled ([$^{32}$P]) dCTP and ([$^3$H]) arachidonic acid and methyl-thymidine were from Dupont NEN (Boston, Mass.). Ionophore (A$_{23187}$), ASA, 3,(4,5-dimethylthiazoyl-2-yl) 2,5 (diphenyl-tetrazolium bromide) (MTT) and guanidinium isothiocyanate were purchased from Sigma Chemical Co (St. Louis, Mo.). Recombinant human interleukin 1$_\beta$ (IL-1$_\beta$) was obtained from R&D systems (Minneapolis, Minn.). Dulbecco's phosphate-buffered saline containing both CaCl$_2$ (0.6 mM) and MgCl$_2$ (1.0 mM) (pH 7.4) (DPBS$^{2+}$), fetal bovine serum (FBS), penicillin and streptomycin were from Bio Whittaker (Walkersville, Md.). Hank's balanced salt solution (HBSS) and F-12K nutrient mixture were from Gibco Laboratories (Grand Island, N.Y.). High-pressure liquid chromatography (HPLC) grade solvents and cesium chloride were purchased from JT Baker (Phillipsburg, N.J.), methyl formate was from Eastman Kodak Co (Rochester, N.Y.) and Sep-Pak C$_{18}$ cartridges were from Waters Associates (Milford, Mass.). Diazomethane was prepared from N-methyl-N'-nitro-N-nitroguanidine purchased from Aldrich Chemical Company (Milwaukee, Wis.). N,O-bis (trimethylsilyl)trifluoroacetamide (BSTFA) was from Pierce (Rockford, Ill.). First strand cDNA synthesis kit and other molecular biology reagents were from Promega (Madison, Wis.). Oligonucleotide primers were purchased to Integrated DNA Technologies (Coralville, Iowa).

Cell Isolation and Culture:

Human type II epithelial A549 cells from human lung carcinoma and normal human skin fibroblast (breast) were obtained from the American Type Culture Collection (Rockville, Md.). The A549 cell line originated from a human alveolar cell carcinoma and was a useful cell line because it was easily assessable and could be maintained in culture without contaminating tissue macrophages. (Lieber, M., et al. (1976) A continuous tumor-cell line from a human lung carcinoma with properties of type II alveolar epithelial-cells. *Int. J. Cancer* Fibroblasts were utilized within their limited window of viability and their passage numbers were recorded (results are reported for cells from 3-5 passages). Epithelial A549 cells were seeded into T-75 cm$^2$ tissue culture flasks and maintained in F-12K medium supplemented with 10% heat-inactivated FBS, penicillin (50 U/mL) and streptomycin (50 (g/mL). Human PMN from healthy donors who had not taken ASA or other medications for at least two weeks were obtained by Ficoll-Hypaque gradient centrifugation and dextran sedimentation, (Böyum A. (1968) Isolation of mononuclear cells and granulocytes from human blood. Isolation of mononuclear cells by one centrifugation, and of granulocytes by combining centrifugation and sedimentation at 1 g. *Scand. J. Clin. Lab. Invest.* 21 (Suppl. 97): 77-89.), and suspended in DPBS$^+$ at pH 7.4. Viability of A549 cells and PMN was determined by their ability to exclude trypan blue and were 95±2 and 97±1%, respectively. These values were not significantly altered during the reported incubations Incubation Conditions:

In incubations involving permeabilized A549 cells (prepared by a rapid freeze-thaw cycle), IL-1$_\beta$ treated (1 ng/ml, 24 h) A549 cells (1.5×10$^6$ cells/ml) were pretreated for 20 main with either vehicle (0.1% EtOH), ASA (500 (M; used throughout), 5 (M 17-ODYA, an inhibitor of cytochrome P450, (Muerhoff A. S., et al. (1989) Prostaglandin and fatty acid ω and (ω-1)-oxidation in rabbit lung: acetylenic fatty acid mechanism-based inactivators as specific inhibitors. *J. Biol. Chem.* 244: 749-756.), or 5 mM Rev 5901 isomer, a 5-LO inhibitor, subjected to two cycles of rapid freezing in a dry ice-acetone bath and thawing to room temperature (full cycle <20 min), and incubated with arachidonic acid (20 (M) for 20 min at 37° C. in 4 ml of DPBS$^{2+}$. In experiments involving radiolabeled arachidonic acid, incubations were initiated with the addition of [$^3$H]-arachidonic acid (0.25 (Ci/ml) plus unlabeled arachidonic acid (20 (M) for 20 min at 37° C.

For time-course experiments involving the generation of 15-HETE from endogenous sources (see FIG. 2B), intact A549 cells were exposed to IL-1$_\beta$ (1 ng/ml) for up to 48 h and then treated with vehicle (containing 0.1% EtOH) or ASA for 20 min followed by addition of ionophore A$_{23187}$ (5 μM) in 4 ml of HBSS for 30 min at 37° C.

In coincubation experiments, confluent A549 cells were exposed to IL-1$_\beta$ (1 ng/ml, 24 h), washed in HBSS and treated with vehicle alone or ASA for 20 min and arachidonic acid (20 (M) for 60 seconds at 37° C. Coincubations were performed by adding PMN to A549 cell monolayers followed by costimulation with ionophore A$_{23187}$ (5 μM) in 4 ml of HBSS for 30 min at 37° C.

Analysis of Eicosanoids:

Incubations were stopped with 2 volumes cold MeOH containing prostaglandin B$_2$ (200 ng) and products were extracted using Sep-Pak C$_{1-8}$ cartridges. Materials which eluted in the methyl formate fractions were concentrated under a stream of N$_2$ and scanned for ultraviolet-absorbing material (in methanol) with a model 8452 spectrophotometer (Hewlett Packard Co, Palo Alto, Calif.) prior to injection into a reversed phase (RP)-HPLC system. This system consisted of a dual pump gradient (LKB, Bromma, Sweden), a diode array detector (Hewlett-Packard 1040M series 1) and a HPLC$^{3D}$ ChemStation software. The collected UV data were recalled at 300 nm to monitor conjugated tetraenes, at 270 nm for trienes and 234 for monoHETEs. All UV spectra were acquired using step=4 nm, Bw=10 nm, and range=220-360 nm with a sampling interval of 0.96 s.

The monohydroxy eicosanoids (i.e. 5-, 12- and 15-HETE) from A549 cells were analyzed using a Ultrasphere-ODS column (5 μm, 4.6 mm×25 cm) (Beckman Instruments, Fullerton, Calif.) was eluted with MeOH/H$_2$O/acetic acid (65:35:0.01; v/v/v) as phase one (t$_0$-20 min), and a linear gradient with MeOH/acetic acid (99.9:0.1, v/v) as phase two (2045 min) at a flow rate of 1.0 ml/min. The R- and S-enantiomers of 15-HETE were resolved and identified using a chiral HPLC system similar to that reported by Hawkins et al. (1988). (Hawkins et al. (1988) Resolution of enantiomers of hydroxyeicosatetraenoate derivatives by chiral phase high-pressure liquid chromatography. *Anal. Biochem.* 173: 456-462.) Briefly, after RP-HPLC material eluting beneath 15-HETE peak was extracted with chloroform and converted into methyl ester by ethereal diazomethane treatment, chiral analysis was performed with a Bakerbond DNBPG (covalent) chiral column (5 μm, 4.6 mm×25 cm) (JT Baker, Phillipsburg, N.J.) eluted with n-hexane/2-propanol (100:0.4; v/v) at a flow rate of 0.8 ml/min. When indicated, generation of 15-HETE from endogenous sources was monitored by radioimmunoassay (RIA). The antibody was raised against 15S-HETE with 0.1% crossreactivity at 50% B/B$_0$ for 5-HETE (PerSeptive Diagnostics, Cambridge, Mass.).

For analysis of LXs (including LXs and 15-epi-LXs) from A549 cell-PMN, coincubations were carried out using either a Waters (Bondapak $C_{18}$ (3.9×300 nm) column eluted with an isocratic mobile phase MeOH/$H_2$O/acetic acid (60:40:0.01; v/v/v) with a flow rate of 0.6 nm ml/min or an Altex Ultrasphere ODS column (5 µm, 10 mm×25 cm) eluted with MeOH/$H_2$O/acetic acid (65:35:0.01; v/v/v) at a flow of 3 ml/min. Peptidoleukotrienes ($LTC_4$ and $LTD_4$) eluted in the MeOH fractions from Sep-Pak cartridge extractions were resolved with a Beckman Ultrasphere-ODS column eluted with MeOH/$H_2$O/acetic acid (65:35:0.01; v/v/v), pH 5.7, at 1 ml/min. Incubations of PMN with 15R-HETE were stopped with MeOH and methyl formate fractions of the Sep-Pak $C_{18}$ extracted products were injected into an Altex Ultrasphere ODS column (5 µm, 10 mm×25 cm) eluted with MeOH/$H_2$O/ acetic acid (65:35:0.01; v/v/v) using a flow of 3 ml/min. The material beneath peaks absorbing at 300 nm were individually collected after RP-HPLC and analyzed by gas chromatography-mass spectrometry (GC-MS) employing a Hewlett-Packard 5890 GC series II equipped with a 5971A mass-selective quadrapole detector as in Clària, J. and Serhan, C. N. (1995) Aspirin triggers previously undescribed bioactive eicosanoids by human endothelial cell-leukocyte interaction *Proc. Natl. Acad. Sci. USA* 92:9475-9479, herein expressly incorporated by reference.

Reverse Transcription (RT) and PCR:

Total RNA was obtained from A549 cells by the guanidinium isothiocyanate-cesium chloride method and cDNA was produced by RT.

Oligonucleotide primers were constructed from published sequences of PGHS-1 and PGHS-2 ((5'-TGC CCA GCT CCT GGC CCG CCG CTT-3' (sense), 5'-GTG CAT CAA CAC AGG CGC CTC TTC-3' (antisense)), and (5'-TTC AAA TGA GAT TGT GGG AAA ATT GCT-3' (sense) and 5'-AGA TCA TCT CTG CCT GAG TAT CTT-3' (antisense)), respectively), 15-LO (5'-ATG GGT CTC TAC CGC ATC CGC GTG TCC ACT-3' (sense) and 5'-CAC CCA GCG GTA ACA AGG GAA CCT GAC CTC-3' (antisense)), 12-LO, (Funk, C. D. and FitzGerald, G. A. (1991) Eicosanoid forming enzyme mRNA in human tissues. *J. Biol. Chem.* 266: 12508-12513), (5'-AGT TCC TCA ATG GTG CCA AC-3' (sense) and 5'-ACA GTG TTG GGG TTG GAG AG-3' (antisense)) and 5-LO (5'-GAA GAC CTG ATG TTT GGC TACC-3' (sense) and 5'-AGG GTT CTC ATC TCC CGG-3' (antisense)). Amplification of the glyceraldehyde-3-phosphate dehydrogenase (GAPDH) primers was performed with 5'-CCA CCC ATG GCA AAT TCC ATG GCA-3' (sense) and 5'-TCT AGA CGG CAG GTC AGG TCC ACC-3' (antisense). PGHS-1, PGHS-2 and GAPDH samples were amplified for 25 cycles of denaturation at 94° C. for 1 min, annealing at 58° C. for 2 min and extension at 72° C. for 3 min. 5-, 12- and 15-LO were amplified at 94° C. (1 min), 55° C. (2 min) and 72° C. (2.5 min) for 35 cycles. PCR products were analyzed by electrophoresis in 2% agarose gel and their identity was monitored by restriction enzyme analysis. For detection of specific PCR-amplified targets, 0.5 (Ci of [$^{32}$P]dCTP (3000 Ci/mmol) was added to the PCR mixture and the products were quantified by phosphorimager using Image-Quant programming (Molecular Dynamics, San Lorenzo, Calif.).

Cell Proliferation:

A microculture 3,(4,5-dimethylthiazoyl-2-yl) 2,5 (diphenyl-tetrazolium bromide) (MTT) assay, (Marshall, N. J., et al. (1995) A critical assessment of the use of microculture tetrazolium assays to measure cell growth and function. *Growth Regul.* 5: 69-84.), was used to examine the actions of LXs and other eicosanoids on cell proliferation. A549 cells and fibroblasts from exponential-phase maintenance cultures were counted and dispensed within replicate 96-well culture plates in 100 µl volumes of medium (~2000 cells/well). Following 24 hours at 37° C., the culture medium was removed, and fresh medium (100 µl) containing either the compounds (5-1000 nM) or vehicle (medium plus 0.15% ethanol) was added to 4 replicates for each condition studied and the culture plates were then incubated for up to 96 hours at 37° C. in a 5% $CO_2$ atmosphere. At the end of this period, 25 µl of freshly prepared MTT in HBSS (5 mg/ml) was added to the wells and the plates were incubated for 4 hours at 37° C. Dye solution was aspirated, wells were washed once with HBSS and dye taken up by the cells was extracted in 100 µl of isopropyl alcohol:1 N HCl (96:4, v/v) and quantitated at 570 nm using a microplate reader (Molecular Devices, Menlo Park, Calif.). In some experiments, cells were grown in 12-well culture plates, treated as above and enumerated using a Neubauer hemocytometer. Viability was assessed routinely using trypan blue exclusion assay. For the A549 cells and fibroblasts, a linear relation was established for the MIT values and cell number within the range of the experiments shown (r=0.995, P<0.005). A549 cells grown for 72 hours in the presence of the compounds (5-1000 nM) or vehicle (0.15% EtOH) were lysed with 0.25 N NaOH and the cellular protein content was determined by applying the Bio-Rad (Richmond, Calif.) microassay method using bovine serum albumin as standard. The mean cellular protein content in resting A549 cells was 46.6±1.5 pg/cell.

Thymidine Incorporation and DNA Synthesis:

A549 cells (~2×10$^4$ cells/ml) were seeded in 96-well plates, allowed to settle for 24 hours and grown for an additional 72 hours in the presence of compounds (5-1000 nM) or vehicle (medium plus 0.15% ethanol). Twenty-four hours before the assay, 2 (Ci/ml of methyl-[$^3$H]thymidine (specific activity 6.7 Ci/mmol) were added to each well. (See Cybulsky et al. (1992) Eicosanoids enhance epidermal growth factor receptor activation and proliferation in glomerular epithelial cells. *Am. J. Physiol.* 262 (*Renal Fluid Electrolyte Physiol.*31): F639-F646.) After pulse-labeling, each well was washed four times with cold DPBS$^{2+}$, and the cells were lysed with NaOH (0.25 N) and radioactivity measured.

The Student's f-test was used for statistical analysis and differences were considered significant at a P value (0.05).

Results

Eicosanoids are formed by initial oxygenation of arachidonic acid by PGHS or LO enzymatic pathways. (Samuelsson B., et al. (1987) Leukotrienes and Lipoxins: structures, biosynthesis, and biological effects. *Science* 237: 1171-1176.) To assess which of the eicosanoid-generating enzymes are present and/or regulated by cytokines in A459 cells, mRNA levels of PGHS-1 and -2 and 5-, 12- and 15-LO from A549 cells grown in the presence or absence of IL-1$_\beta$ were monitored by RT-PCR followed by phosphorimager analysis. As illustrated in FIG. 1A, mRNA levels for PGHS-2 were significantly increased (~twofold) after stimulation of A549 cells with IL-1$_\beta$. In contrast, mRNA levels for PGHS-1 and 5-LO were not significantly altered after exposure of the cells to cytokine (FIG. 1A). A549 cells failed to show either 15- or 12-LO expression before or after cytokine induction (FIG. 1A). The absence of 15-LO mRNA in A549 cells, was further confirmed by performing the RT-PCR in parallel with human lung tissue and peripheral blood monocyte RNA, which are known positive and negative sources, (cf. Funk C. D. and FitzGerald G. A. (1991) Eicosanoid forming enzyme mRNA in human tissues. *J. Biol. Chem.* 266: 12508-12513), of 15-LO mRNA, respectively (see FIG. 1A, inset).

Figure 1B:
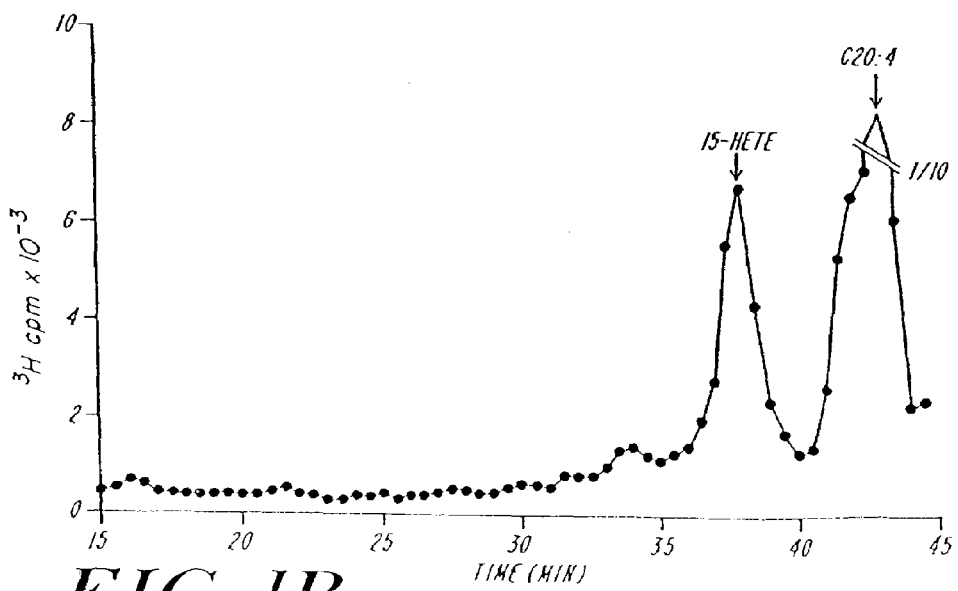
FIG. 1B is a graph showing a RP-HPLC profile of [$^3$H]-labeled mono-hydroxyeicosatetraenoic acids (HETEs) from permeabilized IL-1β-treated A549 cells (1.5×$10^6$ cells/ml) exposed to [$^3$H]-arachidonic acid (20µM) for 20 min at 37° C. Products were extracted and chromatographed using a linear gradient of methanol:$H_2$0:acetic acid (65:35:0.01; v/v/v) and methanol:acetic acid (99.9:0.1, v/v) at a flow rate of 1.0 ml/min. Arrows denote co-chromatography of synthetic standards.
Figure 2A:
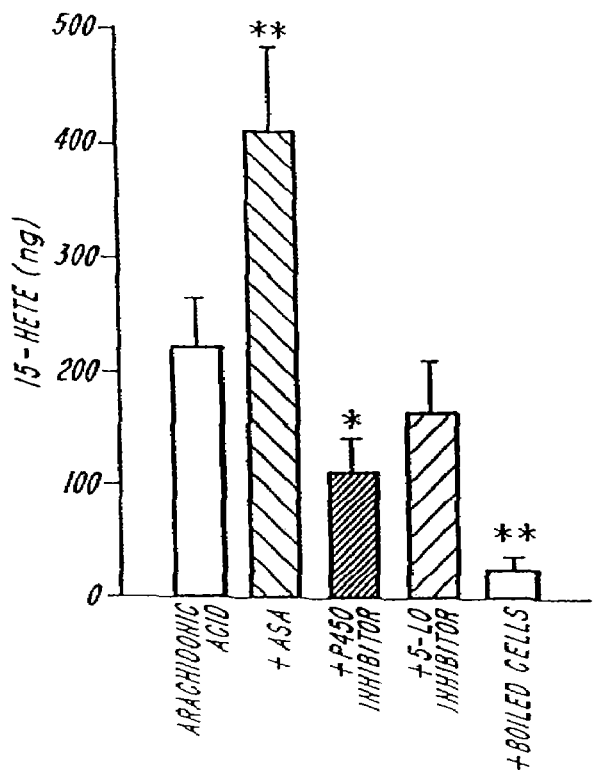
FIG. 2A is a graph showing the generation of 15-HETE A549 cells (6×$10^6$ cells/flask) were treated with IL-$1_β$ (1 ng/ml) for 24 h, subjected to freeze-thaw (two cycles), exposed for 20 min to either vehicle (0.1% vol/vol ethanol (EtOH)), acetylsalicylic acid (ASA), the cytochrome P450 inhibitor (17-octadecaynoic acid (17-ODYA), 5 µM) or the 5-LO inhibitor (Rev-5901 isomer, 5 µM) and incubated with arachidonic acid (20 µM) for 20 min at 37° C. In some experiments, cells were heat-denatured (100° C., 60 min) before incubation. Incubations were stopped with addition of methanol (2 v), and products were extracted for reversed phase (RP)-high-pressure liquid chromatography (HPLC). Data are means ±SEM from four to six separate flasks. *, P<0-05 and **, P<0.01 for treatments versus control are shown.

To characterize the profile of monohydroxy products produced by airway epithelial cells, IL-$1_\beta$-stimulated A549 cells (1.5×10$^6$ cells/ml) were permeabilized and incubated with arachidonic acid, and the products formed were extracted and analyzed by RP-HPLC. The chromatographic profile revealed the presence of a major-product with strong UV absorbance at 234 nm which coeluted with synthetic 15-HETE. Also, when [$^3$H]-arachidonic acid was added to IL-$1_\beta$-treated A549 cells, radiolabeled material was recovered beneath the peak coeluting with 15-HETE (FIG. 1B). In these experiments, the formation of either 5- or 12-H was not consistently observed. ASA treatment of A549 cells led to a marked increase in the formation of 15-HETE, while incubation of permeabilized A549 cells with 17-ODYA, a reported inhibitor of P450 eicosanoid metabolism, (Muerhoff, A. S. et al. (1989) Prostaglandin and fatty acid ω and (ω-1)-oxidation in rabbit lung: acetylenic fatty acid mechanism-based inactivators as specific inhibitors, *J. Biol. Chem.* 244:749-756), resulted in ~50% reduction in 15-HETE (FIG. 2A). 17-ODYA is a potent inhibitor of P450 eicosanoid metabolism and does not selectively inhibit either cyclooxygenase or LO activity. (See Muerhoff et al. and supplier's supporting materials.) The 5-LO inhibitor (Rev-5901 isomer) did not alter the amount of 15-HETE produced by A549 cells in a statistically significant fashion. Heat-denatured A549 cells reduced the quantities of 15-HETE by ~90%, suggesting an enzymatic component in its formation. Production of 15-HETE from endogenous sources of arachidonate was also obtained from intact A549 cells (25.0±10.0 ng/10$^7$ cells) treated with IL-$1_\beta$ (1 ng/ml) for 24 hours. Taken together these results indicate that 15-HETE is the main monohydroxy product generated by A549 cells and suggest that acetylated PGHS-2 and cytochrome P450 each contributes to its biosynthesis.

Figure 2B:
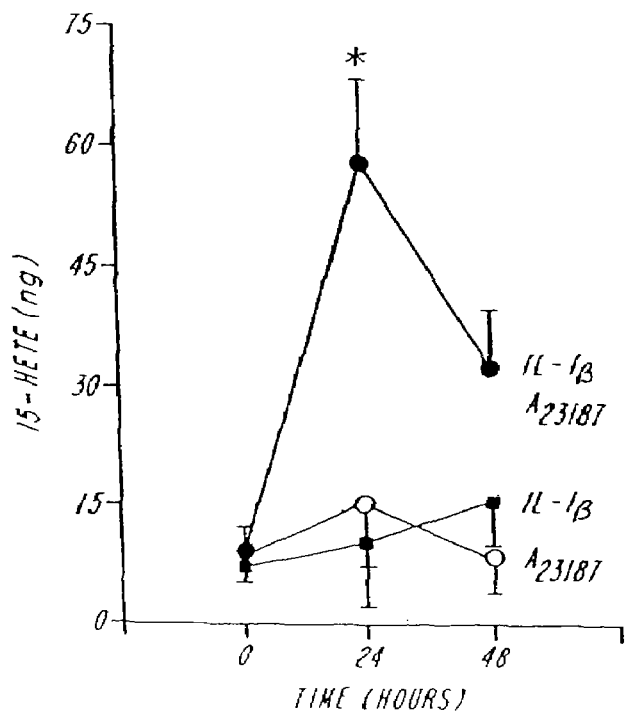
FIG. 2B is a graph showing the time course of 15-HETE formation from endogenous sources. A549 cells (1.5×$10^6$ cells per ml) were grown for 48 h in the absence or presence of IL-$1_β$ (1 ng/ml) and incubated (30 min at 37° C.) in 4 ml HBSS with or without $A_{23187}$ (5 µM). 15-HERE levels were determined by RIA Results represent the mean ±SEM of three different experiments determined by duplicate. *, P<0.05 for treatments versus vehicle are shown.

To investigate the time-course for generation of 15-HETE from endogenous sources of arachidonate, intact A549 cells were exposed to IL-$1_\beta$ (1 ng/ml) for up to 48 h and the amount of immunoreactive 15-HETE present in the cell supernatant was monitored by means of a specific RIA. In resting conditions, A549 cells produced significant levels of immunoreactive 15-HETE (19.1±10.5 ng/10$^7$ cells, n=3, d=2). These values were unchanged by addition of ionophore $A_{23187}$ (5 (M) in the absence of IL-$1_\beta$ (FIG. 2B). Also, in the absence of ionophore stimulation, addition of IL-$1_\beta$ to A549 cells for up to 48 h did not result in an augmented generation of 15-HETE (FIG. 2B). In sharp contrast, addition of IL-$1_\beta$ plus $A_{23187}$ stimulation of A549 cells led to a marked increase in the production of 15-HETE (FIG. 2B). The maximal levels were found at 24 h of exposure to the cytokine with the levels of 15-HETE declining thereafter.

Figure 3:
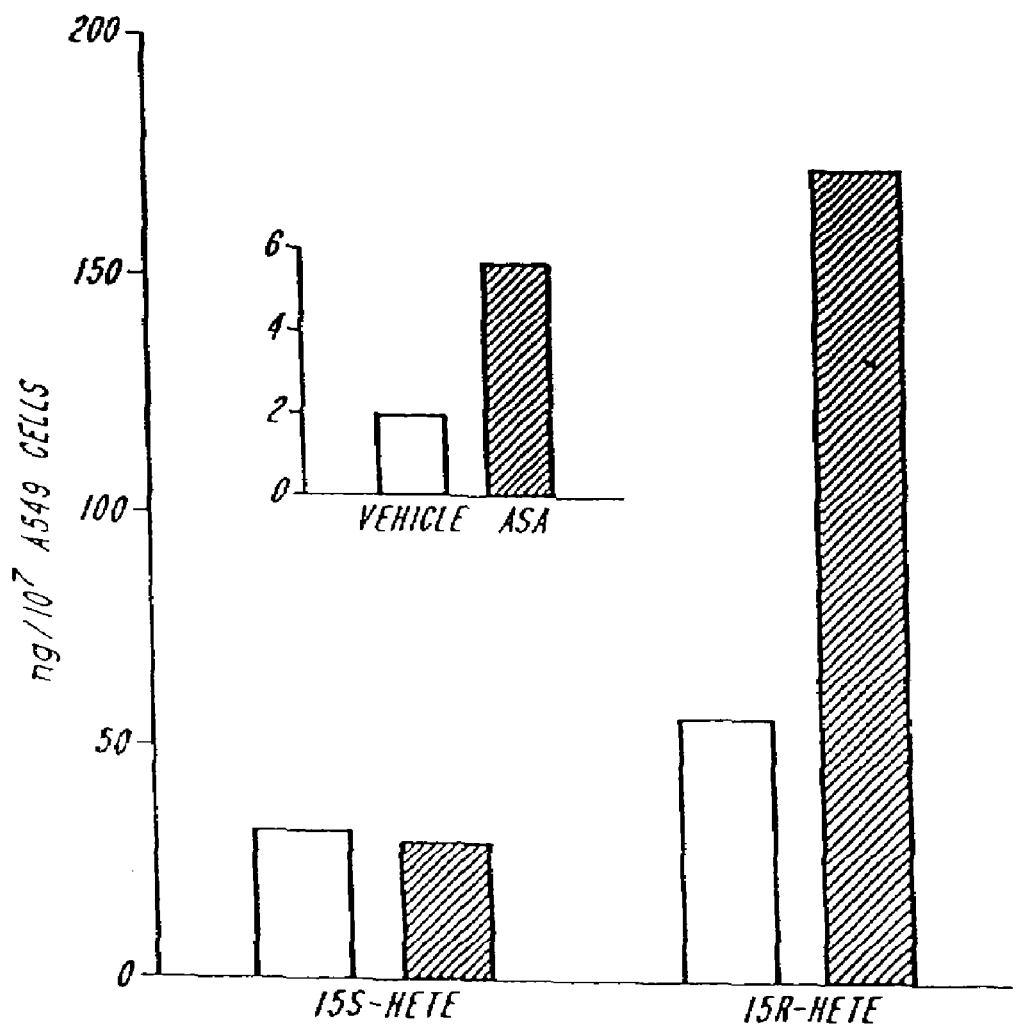
FIG. 3 is a graph showing the relative chiralities of 15-HETE triggered by ASA. A549 cells ($10^7$ cells per flask) were exposed to IL-$1_β$ (1 ng/ml) for 24 11, treated with vehicle (0.1% vol/vol ethanol) (□) or ASA (■) for 20 min and then incubated (30 min. 37° C.) in HBSS containing arachidonic acid (20 µM) and $A_{23187}$ (5 µM). Products were chromatographed by RP-HPLC (as in FIG. 1B) and the region containing 15-HETE was collected, extracted with chloroform and treated with diazomethane. Chiral analysis was performed with a Bakerbond DNBPG (see Methods for details). Results are representative of two separate experiments showing similar results. The inset of FIG. 3 shows the ratio between A549-derived 15R and 15S-HETE in the absence or presence (filled bars) of ASA.

Because the stereochemistry of the alcohol in 15-HETE produced by A549 cells was of interest, the relative amounts of individual R and S enantiomers of 15-HETE generated by IL-$1_\beta$-treated A549 cells were examined using a chiral phase HPLC analysis. (See Methods.) PGHS-2 as well as cytochrome P450 are enzymes other than 15-LO that can each convert arachidonic acid to 15-HETE. ASA-acetylated PGHS-2-derived 15-HETE carries its carbon (C)-15 alcohol group mainly in the R configuration. (Holtzman, M. J., et al., (1992) Identification of a pharmacologically distinct prostaglandin H synthase in cultured epithelial cells, *J. Biol. Chem.* 267:21438-21445). Here, 15-HETE produced by IL-$1_\beta$-primed A549 cells was converted to its methyl ester and subjected to SP-HPLC chiral analysis. The 15-HETE from activated A549 cells was 65% in the R and 35% in the S configuration (FIG. 3). Pretreatment of A549 cells with ASA (20 min, 37° C.) resulted in a 3-fold increase in the amounts of 15R-HETE whereas formation of 15S-HETE remained unaltered (FIG. 3). In the presence of ASA, 15R-HETE accounted for 85% of the total amount of 15-HETE produced by A549 cells. These results indicate that the majority of 15-HETE generated by IL-$1_\beta$-primed A549 cells in presence of ASA was in the R configuration.

Transcellular eicosanoid biosynthesis is an important means of amplifying lipid mediators as well as generating new mediators. (Marcus, A. J. (1995) Aspirin as prophylaxis against colorectal cancer, *N. Engl. J. Med.* 333:656-658.) Costimulation of human endothelial cells and PMN after ASA treatment results in the formation of a new class of bioactive eicosanoids. (Claria, J. and Serhan, C. N. (1995) Aspirin triggers previously undescribed bioactive eicosanoids by human endothelial cell-leukocyte interactions, *Proc. Natl. Acad. Sci. USA* 92:9475-9479.) These novel eicosanoids were identified as 15-epi-LXs and their biosynthesis involve leukocyte transformation of ASA-triggered endothelial-derived 15R-HETE. In view of these results, it is possible that formation of new eicosanoids by transcellular biosynthesis also occurs during epithelial cell-PMN interactions. To test this hypothesis, confluent A549 cells were exposed to IL-$1_\beta$ (1 ng/ml, 24 h), treated with ASA and costimulated with PMN. FIG. 4A shows a representative HPLC profile of material obtained from stimulated cells exposed to ASA, which revealed the presence of four major products with strong UV absorbance when plotted at 300 nm. On-line spectral analysis of these products showed that they each displayed a triplet of absorbing bands characteristic of conjugated tetraene-containing chromophores indicative of the LX basic structure (maxima at 301 nm and shoulders at 288 and 316±2 nm) (FIGS. 4B and 4C).

LXA$_4$ and 15-epi-LXA$_4$ were identified in the chromatographic profiles on the basis of coelution with synthetic standards and the presence of the characteristic chromophore. In these coincubations, 15-epi-LXA$_4$ accounted for ~88% of the total amount of LXA$_4$ detected which is in agreement with the observation that the majority of 15-HETE generated by IL-$1_\beta$-primed A549 cells exposed to ASA is predominantly in the R configuration. (Cf. FIGS. 3 and 4A, 4B and 4C). In this RP-HPLC system, 15-epi-11-trans-LXA$_4$ and LXB$_4$ coeluted, as did II-trans-LXA$_4$ and 15-epi-LXB$_4$ (not shown). These LX isomers were not further resolved by HPLC and are denoted in the profile beneath peaks labeled as peaks A and B, respectively (FIG. 4A). The compounds beneath peaks A and B did resolve as OTMS, methyl ester derivatives in GC-MS (vide infra). The products were present in ~8:2 ratio in favor of their 15R epimers (n=3). Compound C (FIG. 4A) did not coelute with any of the previously identified LXs and was also present in the RP-HPLC profile from activated PMN incubated with 15R-HETE (data not shown, n=5). Material eluting beneath Compound C matched the physical properties of Compound III that was recently isolated from endothelial cell-PMN interactions (Cf. Clària, J. and Serhan, C. N. (1995) Aspirin triggers previously undescribed bioactive eicosanoids by human endothelial cell-leukocyte interactions, *Proc. Natl. Acad. Sci. USA* 92:9475-9479.) Although the complete stereochemistry of compound C remains to be determined, the UV spectral data and chromatographic mobilities suggest that it may be the 15-epimer form of 7-cis-11-trans-LXA$_4$. (Nicolaou, K. C., et al. (1989) Identification of a novel 7-cis-11-translipoxin A$_4$, generated by human neutrophils: total synthesis, spasmogenic activities and comparison with other geometric isomers of LXs A$_4$ and B$_4$, *Biochim. Biophys. Acta* 1003:44-53.) Thus, the LXs generated during epithelial (A549 cell)-PMN costimulation after ASA treatment were predominantly 15-epi-LX (FIG. 4A).

Figure 5A:
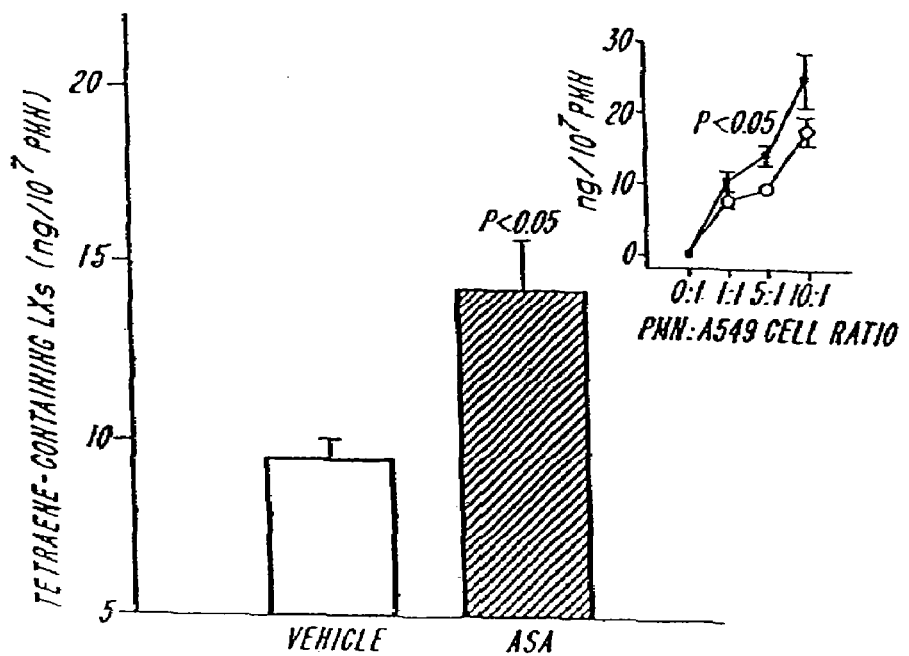
FIG. 5A is a graph showing ASA modulating the formation of tetraene-containing lipoxins (lipoxins plus 15-epi-lipoxins) during epithelial cell-PMN costimulation. A549 cells were exposed to IL-$1_β$ (1 ng/ml, 24 h) and treated (20 min, 37° C.) with either vehicle (0.1% vol/vol) or ASA, before the addition of arachidonic acid (20 µM, 1 min) and freshly isolated PMN (A549/PMN cell ratio of 1:5). Costimulations were carried out as in FIG. 4A. Results represent the mean ±SEM from 3-5 separate donors. The inset of FIG. 5A shows the effect of cell ratio on generation of tetraene-containing lipoxins (lipoxins plus 15-epi-lipoxins) during co-incubations of A549 cells with PMN in the absence (○) or presence (■) of ASA.
Figure 5B:
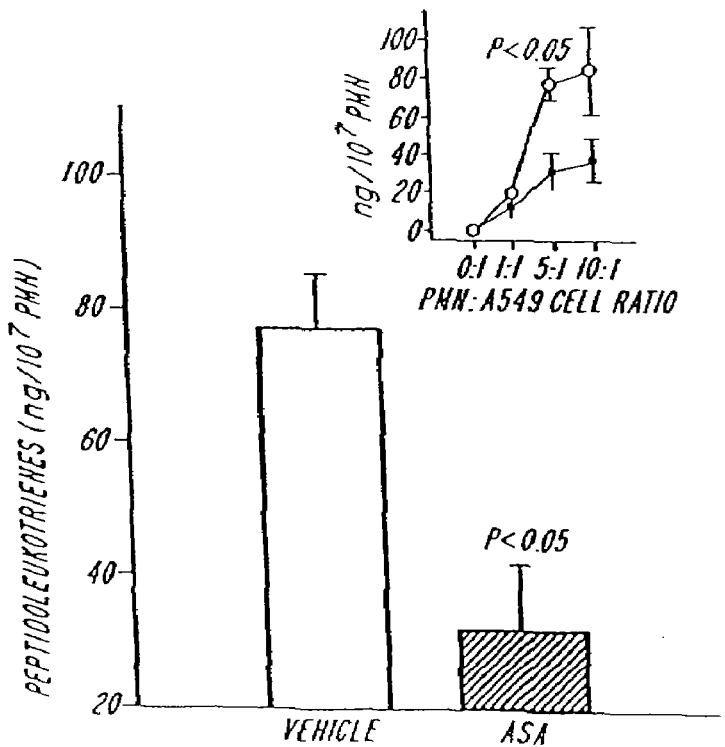
FIG. 5B is a graph showing ASA modulating the formation of peptidoleukotrienes ($LTC_4$ plus $LTD_4$) during epithelial cell-PMN costimulation according to the conditions outlined in FIG. 5A The inset of FIG. 5B shows the effect of cell ratio on generation of peptidoleukotrienes ($LTC_4$ plus $LTD_4$) during co-incubations of A549 cells with PMN in the absence (○) or presence (■) of ASA.

In addition to the ability to produce LXs, coincubations of activated PMN with A549 cells also generate significant amounts (~8 times more than tetraene-containing LXs) of peptidoleukotrienes (pLTs; $LTC_4$, and $LTD_4$) in the absence of ASA (FIGS. 5A and 5B). The amounts of both LXs and pLTs produced in these coincubations were dependent upon individual cell ratios (FIGS. 5A and 5B, insets). Exposure of airway epithelial A549 cells to ASA (20 min) before addition of PMN led to an increase in the formation of LXs and a decrease in pLTs (FIGS. 5A and 5B). Neither PMN nor A549 cells incubated separately, in the absence or presence of ASA, generate detectable levels of LXs or pLTs (FIGS. 5A and 5B and data not shown). Taken together, these results indicate that, during A549 cell-PMN interactions, both LXs and pLTs originate from transcellular routes.

Figure 6A:
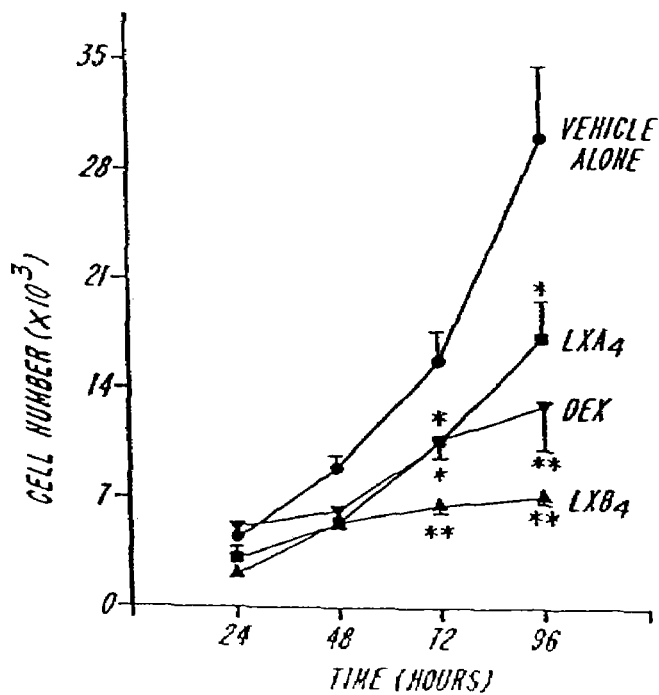
FIG. 6A is a graph showing the effect of Lipoxin $A_4$ ($LXA_4$), Lipoxin $B_4$ ($LXB_4$), Dexamethasone (DEX) and vehicle alone treatment on A549 cell number over time. A549 cells in 96-well plates were treated with either vehicle (0.15% EtOH) or equimolar concentrations ($10^{-6}$ M) of $LXA_4$, $LXB_4$ or DEX for up to 96 hours at 37° C. At the indicated intervals, cells were harvested for the 3,(4,5-dimethylthiazoyl-2-yl) 2,5 (diphenyl-tetrazolium bromide) MTT assay. Data are means ±SEM of 3-7 experiments performed in quadruplicate. *P<0.05 and **, P<0.005 for compounds versus vehicle are shown.
Figure 6B:
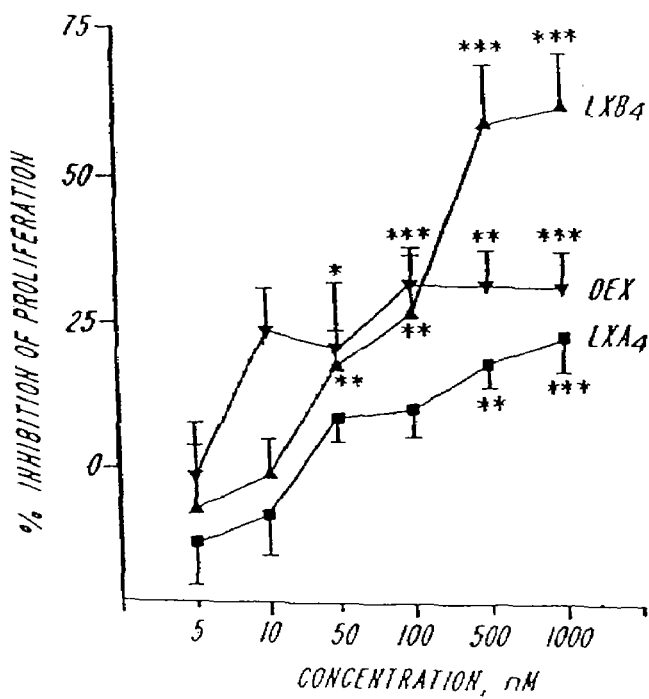
FIG. 6B is a graph showing the effect of $LXA_4$, $LXB_4$, and DEX treatment on the percent inhibition of A549 cell proliferation at varying A549 cell concentrations. A549 cells were exposed to $LXA_4$, $LXB_4$ or DEX at the indicated concentrations for 72 hours at 37° C. Results are means ±SEM of 5-8 experiments performed in quadruplicate. Results are expressed as the percent inhibition of proliferation relative to vehicle. *, P<0.05, , P<0.025 and *P<0.005 for compounds versus vehicle are shown.
Figure 7A:
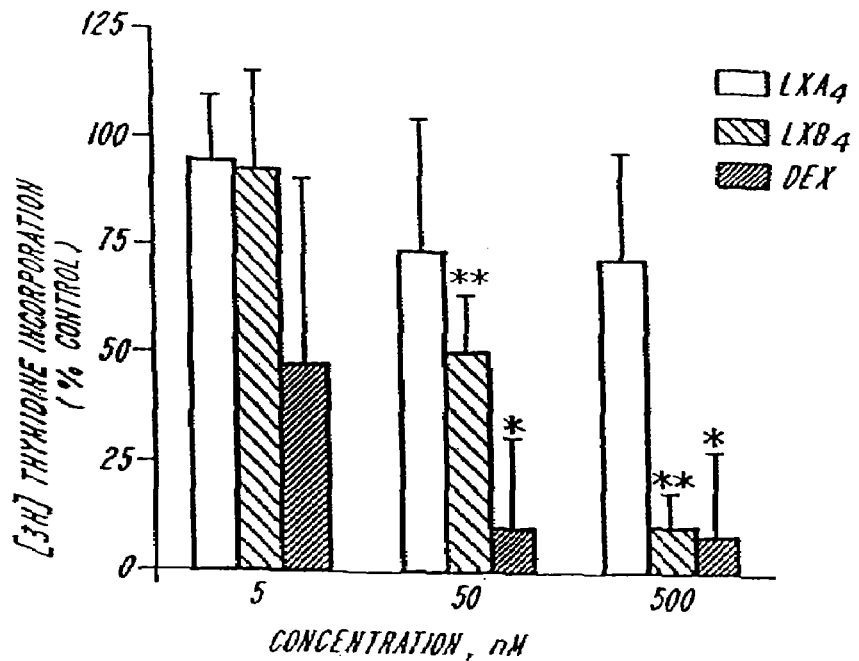
FIG. 7A is a graph showing the effect of $LXA_4$, $LXB_4$ and DEX on A549 cell DNA synthesis, as indicated by 31-thymidine incorporation, where A549 cells were grown for 72 hours in the presence of $LXA_4$, $LXB_4$ and DEX at varying concentrations ranging between 5 nM to 500 nM. Twenty-four hours before the assay, methyl-[$^3$H]thymidine (2 μCi/ml) was added to each well. Cells were subsequently washed four times with $DPBS^{2+}$ (4° C.), lysed with 0.25 N Sodium Hydroxide (NaOH), and radioactivity incorporation was monitored. Values represent mean ±SEM of 3 different experiments performed in quadruplicate. Results are expressed as the percent of [$^3$H]thymidine incorporation relative to vehicle alone. *, P<0.05 and **, P<0.005 for compounds versus vehicle are shown.
Figure 7B:
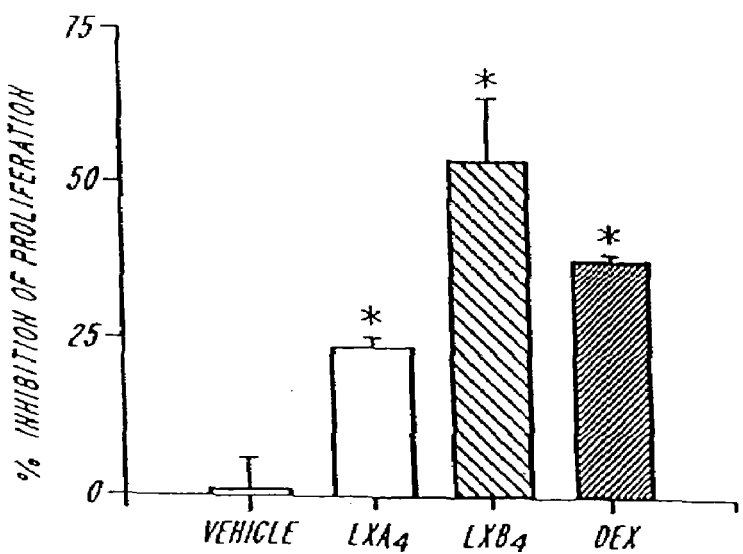
FIG. 7B is a graph showing the effect of $LXA_4$, $LXB_4$ and DEX on the inhibition of A549 cells, where A 549 cells were seeded in 12-well culture plates in the presence of $LXA_4$, $LXB_4$ and DEX (1 μM) and cell counts were obtained at 72 hours by enumerating the trypan-excluding cells. Values represent mean ±SEM of 3 different experiments. Results are expressed as the percent inhibition of proliferation relative to buffer. *, P<0.05 for compounds versus vehicle are shown.

LXs are vasodilators and potent regulators of leukocyte responses, such as inhibition of chemotaxis, adhesion to endothelial cells and transmigration across epithelium. (See Serhan, C. N. (1994) Lipoxin biosynthesis and its impact in inflammatory and vascular events. *biochim. Biophys. Acta* 1212:1-25.) In contrast, pLTs possess both vasoconstrictor and proinflammatory actions as well as stimulate the growth of several cell types including fibroblasts, smooth-muscle and glomerular epithelial cells. (Baud, L., et al. (1985) Leukotriene $C_4$ binds to human glomerular epithelial cells and promotes their proliferation in vitro. *J. Clin. Invest.* 76:374-377.) LXs reverse the vasoconstrictor action of $LTD_4$ in rat renal hemodynamics and block $LTC_4$-stimulated hematopoiesis. (Serhan, C. N. (1994) Lipoxin biosynthesis and its impact in inflammatory and vascular events. *Biochim. Biophys. Acta* 1212:1-25.) Because ASA enhances 15-epi-LX formation and inhibits pLT biosynthesis (FIGS. 5A and 5B), these eicosanoids may play counterregulatory actions on cell proliferation and contribute to ASA's protective mechanisms in human cancer. To this end, the effect of these LO products on epithelial cell proliferation (FIGS. 6A and 6B) was tested and their actions was compared to that of dexamethasone, a well-established inhibitor, employing a soluble microculture tetrazolium (MTT) assay. (Alley, M. C., et al. (1988) Feasiblity of drug screening with panels of human tumor cell lines using a microculture tetrazolium assay. *Cancer Res.* 48:589-601.) These experiments were performed with synthetic $LXA_4$ and $LXB_4$, which were available in sufficient quantities for bioassay, rather than the 15-epi-LX, which are the major LX produced by these cells. As shown in FIGS. 6A and 6B, $LXA_4$ and $LXB_4$ inhibited A549 cell proliferation in a time. (A) and dose-dependent (B) fashion. $LXA_4$ and $LXB_4$ as well as dexamethasone [1 μM] inhibited A549 cell proliferation after 72 and 96 hours of treatment (FIG. 6A) After 72 hours, $LXA_4$ shared the anti-proliferative properties (FIG. 6A) observed for dexamethasone with these cells. (Cf. Croxtall, J. D., and Flower R. J. (1992) Lipocortin 1 mediates dexanethasone-induced growth arrest of the A549 lung adenocarcinoma cell line. *Proc. Natl. Sci. USA* 89:3571-3575.) The half maximum inhibition ($IC_{50}$) for $LXA_4$ was ~80 nM compared to that of dexamethasone, which was ~7 nM. $LXB_4$ at concentrations of 0.5 and 1 μM was (3 times more active than either $LXA_4$ or dexamethasone (FIG. 6B). Of interest, both $LXA_4$ and $LXB_4$ showed essentially equal potency for blocking A549 cell growth when each was added repeatedly (i.e., 24 hour intervals) to the cells for 3 consecutive days (data not shown, n=3, d=4), suggesting that LX may be inactivated by these epithelial cells. Results from additional experiments employing direct cell enumeration (FIG. 7B) and measurement of total cellular protein content (data not shown, n=3, d=4) paralleled those obtained with MTT assay, thus confirming the anti-proliferative actions of LXs in A549 cells. Furthermore, a blockage of DNA synthesis, as determined by $^3$H-thymidine incorporation, occurred when A549 cells were exposed for 72 hours to concentrations of 50 nM or higher of $LXB_4$ or dexamethasone (FIG. 7A). After incubation of A549 cells with the compounds, the viability of the cells, as determined by trypan blue exclusion assay, was found to be ~98%, indicating that these compounds were not cytotoxic within the range of concentrations used in these experiments.

The 15-hydroxy epimeric forms of $LXA_4$ and $LXB_4$ (15-epi-$LXA_4$ and 15-epi-$LXB_4$, respectively), which were the dominant forms of LX isolated from these cells, proved to also be potent inhibitors of epithelial cell proliferation, as shown in the following Table 1.

TABLE 1

LX and 15-epi-LX actions on cell proliferation

| Compound [$10^{-7}$] | % inhibition | P value* |
| --- | --- | --- |
| Vehicle | 1.6 ± 10.3 | NS |
| $LXA_4$ | 16.3 ± 5.2 | NS |
| 15-epi-$LXA_4$ | 20.1 ± 1.9 | <0.025 |
| $LXB_4$ | 30.0 ± 8.5 | <0.005 |
| 15-epi-$LXB_4$ | 79.3 ± 0.3 | <0.001$^\&$ |
| Dexamethasone | 42.1 ± 5.4 | <0.005 |

Cells (2000 A549 cells/well) were grown in 96-well plates and exposed to vehicle (0.15% vol/vol in EtOH/F-12K media) or equimolar concentrations ($10^{-7}$ M) of $LXA_4$, 15-epi-$LXA_4$, $LXB_4$, 15-epi-$LXB_4$, or dexamethasone for 72 hours at 37° C. Values represent ±SEM from 3 to 7 experiments performed in quadruplicate and are expressed as percent inhibition of cell growth.
*P values denot statical differences as compared to cells alone.
$^\&$P < 0.001 for 15-epi-$LXB_4$.

At equimolar levels (100 nM), 15-epi-$LXA_4$ inhibited A549 cell growth to a similar extent as $LXA_4$. On the other hand, 15-epi-$LXB_4$ isolated from conversion of 15R-HETE by activated PMN and added back to the A549 cells gave a more potent anti-proliferative activity than $LXB_4$ (~80% vs. ~34% inhibition proliferation, P<0-001; Table 1). This compound was characterized by UV, HPLC and GC-MS (C value: 23.3). Diagnostic ions for the OTMS methyl ester were m/z 173 (base peak), 203, 289, 379 and less prominent ions at 482 ($M^+$-100) [It was not possible to obtain its molecular ion because of its low abundance]. Thus, the predominant material beneath the peak labeled B in FIG. 4B was consistent with that of 15-epi-$LXB_4$, which gave a shorter C value and separated from $LXB_4$ as OTMS, methyl ester derivative in GC-MS analysis. The mass spectra of 15-epi-$LXB_4$ and $LXB_4$ were essentially identical (not shown) but their C values were distinct. Material eluting beneath the peak denoted as C (isolated from activated PMN incubated with 15R-HETE) also showed a mild inhibitory action on epithelial cell growth (18±2% inhibition proliferation, n=3, d=4). In sharp contrast, 15-epi-trans-$LXA_4$, 11-trans-$LXB_4$, 8,9-acetylenic-$LXB_4$, peptidoleukotrienes ($LTC_4$ and $LTD_4$) and the LX precursors (15S- and 15R-HETE) each tested at $10^{-6}$-$10^{-9}$ M were not able to significantly inhibit A549 cell proliferation (data not shown, n=3-5, d=4). These results indicate that LX and 15-epi-LX gave a stereoselective action in blocking cell proliferation in A549 cells. $LXA_4$ and $LXB_4$ was tested with human skin fibroblasts to determine if they were antiproliferative for this cell type. At 100 nM, both $LXA_4$ and $LXB_4$ inhibited proliferation of fibroblasts $LXB_4$ gave 38.0 (7.5% inhibition and $LXA_4$ 10.7 (1.8% compared to dexamethasone (29.7 (0.4%) as positive control (n=3).

Figure 8:
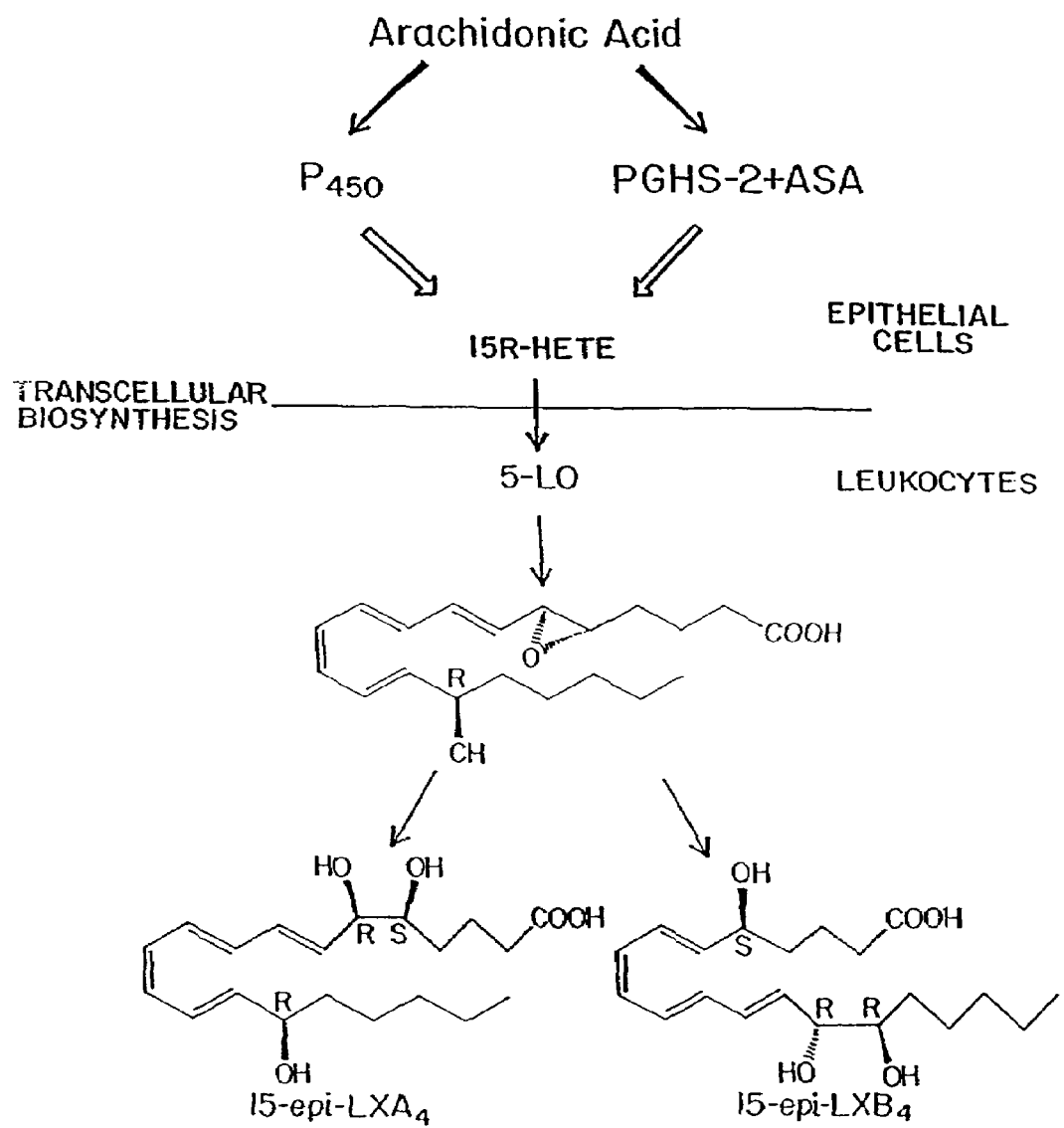
FIG. 8 is a diagram showing the proposed biochemical pathway for generating 15-epi-lipoxins. ASA-acetylated PGHS-2 and/or P450 activities contribute to 15R-HETE. Epithelial 15R-HETE undergoes transcellular conversion by Leukocyte 5-LO to a 15-epi-5(6)-epoxytetraene intermediate, which is common to both 15-epi-$LXA_4$ and 15-epi-$LXB_4$.

The presence of an active cytochrome P450 enzyme system in human airway A549 cells, (Vogel, et al. (1994) Transforming growth factor-β1 inhibits TCDD-induced cytochrome P4501AI expressions in human lung cancer A549 cells. *Arch. Toxicol.* 68: 303-307.), together with the results that inhibition of P450 as well as heat denaturing blocks 15-HETE generation in these cells (FIG. 2A) suggests that this enzyme system in epithelial cells also contributes to 15-HETE biosynthesis and the generation of 15-epi-lipoxin by transcellular routes (FIG. 8). Taken together, these observations (FIGS. 1-4) establish the existence of two separate enzymatic pathways (i.e. ASA-acetylated PGHS-2 and cytochrome P450), which can initiate the formation of 15-epi-lipoxin during airway epithelial cell-PMN interactions (FIG. 8). Also, it should be noted that, in view of ASA's ability to induce P450 enzymes, Pankow, D. et al. (1994) Acetylsalicylic acid—inducer of cytochrome P-450 2E1? *Arch. Toxicol.* 68: 261-265, it is possible that these two independent routes may act in concert to generate 15-epi-lipoxin.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

I claim:

1. A method of inducing vasodilation to treat or prevent a vasocontractive response or condition, comprising: administering to a subject a pharmaceutical composition that includes a substantially purified 15-epi-lipoxin compound in which the absolute configuration at the 15 carbon is R and a pharmaceutically acceptable carrier.

2. A method of claim 1, wherein the substantially purified 15-epi-lipoxin compound in which the absolute configuration at the 15 carbon is R is 15R-5,6, 15-trihydroxy-7,9, 13-trans-11-cis-eicsoatetraenoic acid.

3. A method of claim 2, wherein the 15R-5,6, 15-trihydroxy-7,9, 13-trans-11-cis-eicsoatetraenoic acid has a 5S, 6R configuration.

4. A method of claim 1, wherein the substantially purified 15-epi-lipoxin compound in which the absolute configuration at the 15 carbon is R is 15R-5,14,15-trihydroxy-6,10,12-trans-8-ciseicosatetraenoic acid.

5. A method of claim 4, wherein the 15R-5,14,15-trihydroxy-6,10,12-trans-8-ciseicosatetraenoic acid has a 5S, 14R configuration.

6. A method of claim 1, wherein the vasocontractive response or condition is selected from the group consisting of a renal hemodynamic disease, including glomerular disease, and a cardiovascular disease, including hypertension, myocardial infarction, and myocardial ischemia.

7. A method of claim 6, wherein the substantially purified 15-epi-lipoxin compound in which the absolute configuration at the 15 carbon is R is 15R-5,6, 15-trihydroxy-7,9, 13-trans-11-cis-eicsoatetraenoic acid.

8. A method of claim 7, wherein the 15R-5,6, 15-trihydroxy-7,9, 13-trans-11-cis-eicsoatetraenoic acid has a 5S, 6R configuration.

9. A method of claim 6, wherein the substantially purified 15-epi-lipoxin compound in which the absolute configuration at the 15 carbon is R is 15R-5,14,15-trihydroxy-6,10,12-trans-8-ciseicosatetraenoic acid.

10. A method of claim 9, wherein the 15R-5,14,15-trihydroxy-6,10,12-trans-8-ciseicosatetraenoic acid has a 5S, 14R configuration.

* * * * *